United States Patent [19]

Chirgadze et al.

[11] Patent Number: 5,599,793
[45] Date of Patent: Feb. 4, 1997

[54] ANTITHROMOBOTIC AGENTS

[75] Inventors: Nickolay Y. Chirgadze, Carmel; Aaron L. Schacht, Indianapolis; Gerald F. Smith, Indianapolis; Michael R. Wiley, Indianapolis, all of Ind.

[73] Assignee: Eli Lilly and Company, Indianapolis, Ind.

[21] Appl. No.: 397,449

[22] Filed: Mar. 2, 1995

Related U.S. Application Data

[63] Continuation-in-part of Ser. No. 207,491, Mar. 4, 1994, abandoned.

[51] Int. Cl.$^6$ .............................. A61K 38/00; C07K 5/00; C07K 7/00; C07K 17/00
[52] U.S. Cl. .......................... 514/18; 514/19; 530/331; 540/593; 540/594; 540/595; 544/323; 546/199; 546/246; 548/122; 548/123; 548/124; 548/125; 548/128; 548/131; 548/190; 548/214
[58] Field of Search .................. 530/331; 514/18–19; 540/593–595; 544/323; 546/199, 246; 548/122–125, 950, 128, 131, 190, 214, 233, 566, 518, 558, 326.5, 453, 535

[56] References Cited

U.S. PATENT DOCUMENTS

| | | | |
|---|---|---|---|
| 4,316,889 | 2/1982 | Bajusz et al. | 424/177 |
| 4,346,078 | 8/1982 | Bajusz et al. | 424/177 |
| 4,399,065 | 8/1983 | Bajusz et al. . | |
| 4,478,745 | 10/1984 | Bajusz et al. . | |
| 4,703,036 | 10/1987 | Bajusz et al. | 514/18 |
| 5,053,392 | 10/1991 | Klein et al. | 514/18 |
| 5,153,176 | 10/1992 | Abe et al. | 514/18 |
| 5,202,416 | 4/1993 | Steuber et al. | 530/322 |
| 5,204,323 | 4/1993 | Findlay et al. | 514/2 |
| 5,250,660 | 10/1993 | Shuman et al. | 530/344 |
| 5,252,566 | 10/1993 | Shuman et al. | 514/210 |
| 5,380,713 | 1/1995 | Balasubramanian et al. | 514/18 |
| 5,416,093 | 5/1995 | Shuman | 514/307 |
| 5,430,023 | 7/1995 | Gesellchen et al. | 514/18 |
| 5,436,229 | 7/1995 | Ruterbories et al. | 514/18 |
| 5,439,888 | 8/1995 | Shuman et al. | 514/18 |
| 5,484,772 | 1/1996 | Sall et al. | 514/18 |
| 5,488,037 | 1/1996 | Sall et al. | 514/19 |

FOREIGN PATENT DOCUMENTS

| | | |
|---|---|---|
| 16380/95 | 4/1995 | Australia . |
| 21801/95 | 6/1995 | Australia . |
| 293881 | 12/1988 | European Pat. Off. . |
| 410411 | 1/1991 | European Pat. Off. . |
| 479489 | 4/1992 | European Pat. Off. . |
| 526877 | 8/1992 | European Pat. Off. . |
| 503203 | 9/1992 | European Pat. Off. . |
| 504064 | 9/1992 | European Pat. Off. . |
| 529568 | 3/1993 | European Pat. Off. . |
| 530167 | 3/1993 | European Pat. Off. . |
| 542525 | 5/1993 | European Pat. Off. . |
| 648780 | 8/1994 | European Pat. Off. . |
| WO93/08211 | 4/1993 | WIPO . |
| WO93/11152 | 6/1993 | WIPO . |
| WO93/15756 | 8/1993 | WIPO . |
| WO94/29335 | 12/1994 | WIPO . |
| WO94/29336 | 12/1994 | WIPO . |
| WO95/09634 | 4/1995 | WIPO . |
| WO95/09858 | 4/1995 | WIPO . |
| WO95/09859 | 4/1995 | WIPO . |

OTHER PUBLICATIONS

Bajusz, S., et al., *J. Med. Chem.*, 1990, 33, 1729–1735.
Fareed, J., et al., *Annals N.Y. Academy of Sciences*, 1981, 765–784.
Shuman, et al., Proceedings of the Twelfth American Peptide Symposium, Jun. 16–21, 1991, pp. 799–802.
Wilson, et al., American Heart Association, Nov. 11–14, 1991, Anaheim Convention Center, Anaheim, CA, Abstract.
Bajusz, et al., *Int. J. Peptide Res.*, 12, 1978, 217–221.
Gesellchen, et al., Tenth American Peptide Symposium, May 23–28, 1987, St. Louis, MO.
Claeson, et al., Proceedings of the Twelfth American Peptide symposium, Jun. 16–21, 1991, Cambridge, MA, pp. 824–825.
Smith, G. F., Shuman, R. T. Gesellchen, P. D., Craft, T. J., Gifford, P., Kurz, K. D., Jackson, C. V., Sandusky, G. E., and P. D. Williams, A New Family of Thrombin Inhibitors with Improved Specificity and Therapeutic Index. (Submitted to the American Heart Association, Oct., 1991, Circulation Oct., 1991, vol. 84, II–579, 1991), Abstract.
Jackson, V., Wilson, H., Frank, J., Crowe, V., Craft, T., and G. Smith. The Thrombin Inhibitor, Methyl–D–Phe–P-ro–Arginal—An Effective Adjunct to Coronary Artery Thrombolysis in the Anesthetized Dog. FASEB J. 5(4)A520 (1991).
Crowe, V., Frank, J., Wilson, H., Coffman, B., Smith, G., and V. Jackson. Anticoagulant and Antithrombotic Efficacy of the Novel Thrombin Inhibitor Methyl–D–Phg–Pro–Arginal in a Canine Model of Coronary Thrombosis. FASEB J. 5(4)A520 (1991).
Wilson, H., Frank J., Crowe, V., Coffman, B., Smith, G., Shuman, R., and V. Jackson. Anticoagulant and Antithrombotic Efficacy of the Novel Thrombin Inhibitor, Methyl–D–Phg–Pro–Arginal, in a Canine Model of Coronary Thrombosis (Arteriosclerosis and Thrombosis, 11(5), Oct., 1991) p. 1586a.

(List continued on next page.)

*Primary Examiner*—Toni R. Scheiner
*Assistant Examiner*—Sheela J. Huff
*Attorney, Agent, or Firm*—Thomas E. Jackson; David E. Boone

[57] ABSTRACT

This invention relates to L-arginine aldehyde derivatives, having the Formula I

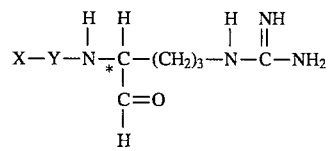

where X and Y have the values defined in the description, as well as pharmaceutical formulations containing those compounds and methods of their use as thrombin inhibitors, coagulation inhibitors, and thromboembolic disorder agents.

24 Claims, No Drawings

OTHER PUBLICATIONS

Jackson, V., Wilson, H., Frank, J., Crowe, V., Coffman, B., Shuman, R., and G. Smith. The Novel Thrombin Inhibitor Methyl–D–Phg–Pro–Arginal: An Effective Conjunctive Agent to Coronary Artery Thrombolysis in the Anesthetized Dog. (Arteriosclerosis and Thrombosis, 11(5), Oct., 1991) p. 1586a.

Shuman, R. T., Rothenberger, R. B., Campbell, C. S., Smith, G. F., Jackson, C. V., Kurz, K. D., and P. D. Gesellchen. Prevention of Reocclusion by a Thrombin Inhibitor. (American Peptide Symposium, Jun., 1991, pp. 799–800).

Shuman, R. T., Rothenberger, R. B., Campbell, C. S., Smith, G. F., Jackson, C. V., Kurz, K. D., and P. D. Gesellchen. A Series of Highly Active Serine Proteinase Inhibitors. (American Peptide Symposium, Jun. 1991, pp. 801–802).

Jackson, C. V., Frank, J. D., Crowe, V. G., Craft, T. J., and G. F. Smith. Assessment of the Anticoagulant and Antithrombotic Efficacy of the Thrombin Inhibitor, BOC–Phe–Pro–Arginal, in a Canine Model of Coronary Thrombosis. *Arteriosclerosis*, 10 922A (1990).

Jackson, C. V., Frank, J. D., Crowe, V. G., Craft, T. J., and G. F. Smith. The Thrombin Inhibitor, BOC–D–Phe–Pro–Arginal. An Effective Adjunct to Coronary Artery Thrombolysis in the Anesthetized Dog. *Arteriosclerosis*, 10 923a (1990).

Shackelford, K. A., Tanzer, R. L., Shuman, R., Gesellchen, P. D., Grindey, G. B., Sundboom, J. L., Smith, G. F., and R. L. Merriman. Inhibition of Spontaneous Metastasis by Boc–D–Phe–Pro–Arginal. Ameican Association for Cancer Research, San Francisco, 1989. *Proc. Am. Assn. Cancer Res.*, 30 86, 1989.

Neubauer, B. L., Clemens, J. A., Gesellchen, P. D., Hirsch, K. S., Hoover, D. M., Merriman, R. L., and G. F. Smith. Endocrine Characterization and Sensitivity of the PAIII Prostatic Adenocarcinoma in Male Lobund–Wistar (LW) Rats to Anti–Fibrin Agents. American Association for Cancer Research. New Orleans, May 1988, *Proc. Am. Assn. Cancer Res.*, 29 240 (1988).

Neubauer, B. L., Best, K. L., Gesellchen, P. D., Goode, R. L., Merriman, R. L., Tanzer, L. R., Shaar, C. J., Shuman, R., Sundboom, Pro–Arginal on the Metastasis of the PAIII Prostatic Adenocarcinoma in Male Lobund Wistar (LW) Rats. American Urological Assocation. Boston, May 1988, *J. Urol.*, 139 175A (1988).

Gesellchen, P. D., Smith, G. F., et al., Anticoagulant, Antithrombotic, and Antimetastatic Effects of a Serine Proteinase Inhibitor. 10th American Peptide Symposium, Washington University, St. Louis, MO (1987), Abstract.

Smith, G. F., Sundboom, J. L., Best, K., Gesellchen, P. D., Merriman, R. L., Shuman, R., and Neubauer, B. L. Heparin Boc–D–Phe–Pro–Arginal, and Warfarin (Fibrin Antagonists) Inhibit Metastasis in an In Vivo Model. American Chemical Society National Meeting. Abstract BIOL 70 Biochemistry (1987).

K. D. Kurz, T. Smith, R. A. Moore, and B. W. Main. Comparison of Thrombin Inhibitors in Rat Models of Thrombosis and Thrombolysis. FASEB Journal, vol. 5 (No. 4), 1991, Abstract #886.

Tomori, et al., *Chromatographia*, vol. 19, 437–442 (1984).

Dayhoff, *Atlas of Protein Sequence and Structure*, 5, pp. 85–89 (1972).

Shuman, et al., *J. Med. Chem.*, 36(3), 314–319 (1993).

Jackson, et al., *J. Cardiovasc. Pharmacol.*, 21(4), 587–594 (1993).

Cheng, et al., *Tetrahedron Lett.*, 32 (49), 7333–7336 (1991).

Bagdy, et al., *Thrombosis and Haemostasis*, 68(2), 125–129 (1992).

*Thrombosis and Haemostasis*, 65, 1289, Nos. 2150–2151 and 2152 (1991).

Bagdy, et al., *Thrombosis and Haemostasis*, 67(3), 325–330 (1992).

Bagdy, et al., *Thrombosis and Haemostasis*, 67(3), 357–365 (1992).

Balasubramanian, et al., *J. Med. Chem.*, 36, 300–303 (1993).

Shuman et al., Oral Activity of Tripeptide Aldehyde Thrombin Inhibitors, Thirteenth American Peptide Symposium, Jun. 20–25, 1993, Abstract.

Kurz et al., Antithrombotic Efficacy in the Rat After Intravenous and Oral Administration of a Direct Inhibitor of Thrombin FASEB, Mar. 28–Apr. 1, 1993.

Iwanowicz, et al., *Bioorg. Med. Chem. Lett.*, 2(12), 1607–1612 (1992).

Barabas, et al., *Blood Coagul. Fibrin.*, 4, 243–248 (1993).

Jackson, et al., Conjunctive Therapy with the Thrombin Inhibitor, LY 294468, and Aspirin Produced Enhanced Antireocclusive Activity When Used in a Canine Model of Streptokinase–Induced Coronary Thrombolysis, *The Pharmcologist*, 35(3), 207 (1993), Abstract #407.

Pozagay, et al., Study of the Specificity of Thrombin with Tripeptidyl–p–Nitroanilide Substrates, *Eur. J. Biochem.*, 115, 491–495 (1981).

Jackson, et al., *The Journal of Pharmacology and Experimental Therapy*, 261(2), 546–552 (1992).

Stueber, et al., Proc. of the 13th American Peptide Symposium, Jun. 20–25, 1993.

Stürzebecher, et al., XIVth Congress of the International Society on Thrombosis and Hemostasis, Jul. 4–9, 1993.

Simoons et al., *Circulation*, 90, I–231, Abstr. 1241 (1994).

ANTITHROMOBOTIC AGENTS

This is a continuation-in-part of application Ser. No. 08/202,491, filed Mar. 4, 1994, and now abandoned.

This invention relates to thrombin inhibitors which are useful anticoagulants in mammals. In particular it relates to peptide derivatives having high antithrombotic activity, anticoagulant activity, and oral bioavailability.

The process of blood coagulation, thrombosis, is triggered by a complex proteolytic cascade leading to the formation of thrombin. Thrombin proteolytically removes activation peptides from the Aα-chains and Bβ-chains of fibrinogen, which is soluble in blood plasma, initiating insoluble fibrin formation.

Anticoagulation is currently achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest in small synthetic peptides that are recognized by proteolytic enzymes in a manner similar to that of natural substrates has grown. Tripeptide aldehydes such as D-Phe-Pro-Arg-H, Boc-D-Phe-Pro-Arg-H, and D-MePhe-Pro-Arg-H, Bajusz et al., *J. Med. Chem.*, 33, 1729–1735 (1990) demonstrate potent direct inhibition of thrombin. Many investigators have synthesized analogs in an effort to develop pharmaceutical agents, for example Shuman et al., *J. Med. Chem.*, 36, 314–319 (1993), as well as European patent applications, publication numbers 479489 amd 530167. Early clinical studies which demonstrate that D-MePhe-Pro-Arg-H sulfate is an anticoagulant in man have been reported, see Simoons et al., *Circulation*, 90, I-231, Abstr. 1241 (1994).

Although the heparins and coumarins are effective anticoagulants, and no drug has yet emerged from the known tripeptide aldydes, and despite the continuing promise for this class of compounds, there exists a need for anticoagulants that act selectively on thrombin, and independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

Accordingly, it is a primary object of the present invention to provide novel peptide derivatives that are potent thrombin inhibitors useful as anticoagulants.

Other objects features and advantages will be apparent to those skilled in the art from the following description and claims.

The present invention provides a thrombin inhibiting compound having the Formula I

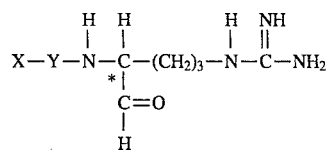

wherein

X is prolinyl, homoprolinyl,

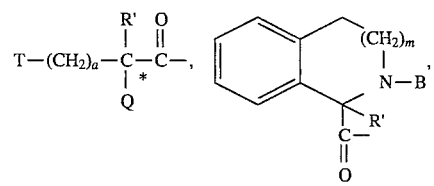

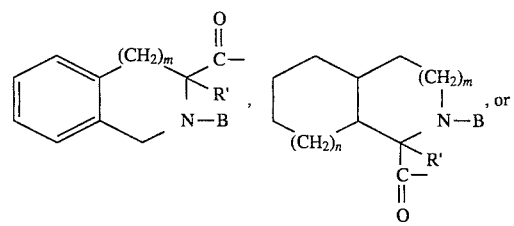

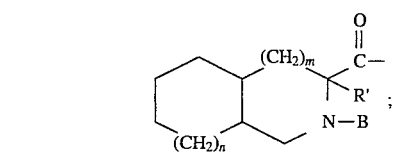

T is $C_3$–$C_8$ cycloalkyl, $C_1$–$C_8$ alkyl,

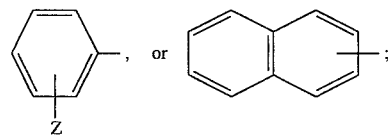

a is 0 or 1;

Q is —OH, $C_1$–$C_4$ alkoxy, or —NH—A;

A is $C_1$–$C_4$ alkyl, R"SO$_2$—, R"OC(O)—, R"C(O)—, HOOCSO$_2$—, HOOCC(O)—, or —(CH$_2$)$_g$—COOH;

g is 1, 2, or 3;

B is hydrogen or $C_1$–$C_4$ alkyl;

R' is hydrogen or $C_1$–$C_4$ alkyl;

R" is $C_1$–$C_4$ alkyl, $C_1$–$C_4$ perfluoroalkyl, —(CH$_2$)$_d$—COOH, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

d is 1, 2, or 3;

m is 0, 1, or 2;

n is 0, 1, or 2;

Y is

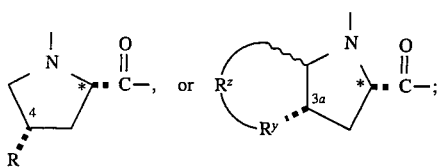

R is $C_1$–$C_6$ alkyl, $C_3$–$C_8$ cycloalkyl, or —$(CH_2)_p$—L—$(CH_2)_q$—T'; where p is 0, 1, 2, 3, or 4, L is a bond, —O—, —S—, or —NH—, q is 0, 1, 2 or 3, and T' is hydrogen, $C_1$–$C_4$ alkyl, $C_3$–$C_8$ cycloalkyl, —COOH, —$CONH_2$, or Ar, where Ar is unsubstituted or substituted aryl as defined above for R";

$R^y$ is —$CH_2$—, —O—, —S—, or —NH—;

$R^z$ is a bond or, when taken with $R^y$ and the three adjoining carbon atoms, forms a saturated carbocyclic ring of 5–8 atoms, one atom of which may be —O—, —S—, or —NH—; and Z is hydrogen, $C_1$–$C_4$ alkyl, $C_1$–$C_4$ alkoxy, hydroxy, halo, or $R_aSO_2NH$—, where $R_a$ is $C_1$–$C_4$ alkyl;

provided that when p and q are each 0 and L is a bond, T' is not hydrogen;

or a pharmaceutically acceptable salt thereof; or a pharmaceutically acceptable solvate of said compound or salt thereof.

In addition to the compounds of Formula I, the present invention provides pharmaceutical formulations comprising a compound of Formula I in association with a pharmaceutically acceptable carrier, diluent or excipient.

The present invention also provides a method of inhibiting thrombosis in mammals comprising administering to a mammal in need of treatment, an antithrombotic dose of a compound of Formula I.

The present invention further provides a method of inhibiting thrombin comprising administering to a mammal in need of treatment, a thrombin inhibiting dose of a compound of Formula I.

This invention relates to new inhibitors of thrombin, pharmaceutical compositions containing the compounds as active ingredients, and the use of the compounds as anticoagulants for prophylaxis and treatment of thromboembolic diseases such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

The term "alkyl" by itself or as part of another substituent means a straight or branched chain alkyl radical having the stated number of carbon atoms such as methyl, ethyl, n-propyl, isopropyl, n-butyl, t-butyl, isobutyl and sec-butyl. The term "perfluoroalkyl" by itself or as part of another substituent means a straight or branched chain alkyl radical having the stated number of carbon atoms in which each hydrogen atom is replaced with a fluorine atom such as trifluoromethyl, perfluoroethyl, perfluoro-n-propyl, perfluoroisopropyl, perfluoro-n-butyl, perfluoro-t-butyl, perfluoroisobutyl and perfluoro-sec-butyl.

The term "$C_3$–$C_8$ cycloalkyl" refers to the saturated alicyclic rings of three to eight carbon atoms such as cyclopropyl, methylcyclopropyl, cyclobutyl, cyclopentyl, cyclohexyl, 4-methylcyclohexyl, cyclooctyl, and the like.

The term "alkoxy" means a straight or branched chain alkyl radical having the stated number of carbon atoms bonded to the parent moiety by an oxygen atom. The term "halo" means chloro, fluoro, bromo or iodo. The term "acetyl" means $CH_3$—C(O)—. The term "t-butyloxycarbonyl" means $(CH_3)_3C$—O—C(O)— and is abbreviated "Boc". The term "benzyloxycarbonyl" means $C_6H_5CH_2$—O—C(O)— and is abbreviated "Cbz".

The term "5- or 6-membered heterocyclic ring" means any 5- or 6-membered ring that will afford a stable structure containing one or two nitrogen atoms; one sulfur atom; one oxygen atom; one nitrogen and one sulfur atom; or one nitrogen and one oxygen atom. The 5-membered ring has one or two double bonds and the 6-membered ring has two or three double bonds. Such heterocyclic systems include furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl and thiazinyl.

The term "9- or 10-membered heterocyclic ring" means any bicyclic group in which any of the above 5- or 6-membered rings is fused to a benzene ring or another 6-membered heterocyclic ring as defined above that will afford a stable structure. These heterocyclic systems include indolyl, benzothienyl, benzofuryl, benzoxazolyl, benzoisoxazolyl, benzopyrazolyl, quinolinyl, isoquinolinyl, benzimidazolyl and benzothiazolyl.

It will be appreciated that many of the above heterocycles may exist in tautomeric forms. All such forms are included within the scope of this invention.

All of the aryl groups listed for the definition of R" or Ar independently are unsubstituted or substituted with one or two substituents that will afford a stable structure independently selected from halo, hydroxyl, $C_1$–$C_4$ alkyl, $C_1$–$C_4$ alkoxy, amino (—$NH_2$), mono($C_1$–$C_4$ alkyl)amino, —$(CH_2)_k$COOH, mercapto, —$S(O)_h(C_1$–$C_4$ alkyl), —$NHS(O)_h(C_1$–$C_4$ alkyl), —$NHC(O)(C_1$–$C_4$ alkyl), —$S(O)_hNH_2$, —$S(O)_hNH(C_1$–$C_4$ alkyl), or —$S(O)_hN(C_1$–$C_4$ alkyl)_2$, h is 0, 1 or 2, and k is 0, 1, 2, 3, or 4. One particularly preferred value for the substituent R"C(O)— is 1-methylindol-2-oyl.

In the representation of Formula I, the carbonyl functionality of group X is attached to the amine functionality of the Y group. The carbonyl functionality of Y is then attached to the amino group drawn in Formula I.

The group

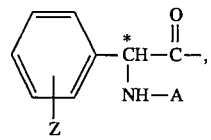

where Z and A are both hydrogen, is referred to at times herein as phenylglycyl and abbreviated Phg. Compounds wherein A is, e.g., methyl, are referred to as the $N^\alpha$methyl-phenylglycyl group and abbreviated MePhg. Substituted compounds wherein Z is other than hydrogen are referred to by the type and position of the substituent group, e.g., 3'-chlorophenylglycyl or Phg(3-Cl).

The group

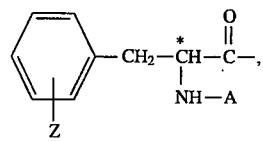

where Z and A are both hydrogen, is referred to at times herein as phenylalanyl and abbreviated Phe. Compounds wherein A is, e.g., methyl, are referred to as the N^α methyl-phenylalanyl group and abbreviated MePhe. Substituted compounds wherein Z is other than hydrogen are referred to by the type and position of the substituent group, e.g., 3'-chlorophenylalanyl or Phe(3-Cl).

The groups

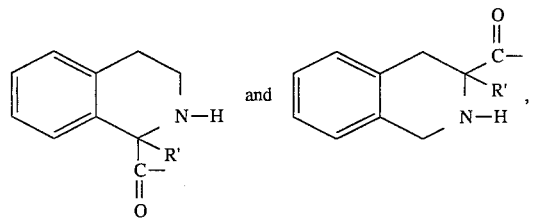

when R' is hydrogen, are referred to at times herein as 1- and 3-tetrahydro-isoquinolinecarbonyl, respectively, and are respectively abbreviated 1-Tiq and 3-Tiq.

The groups

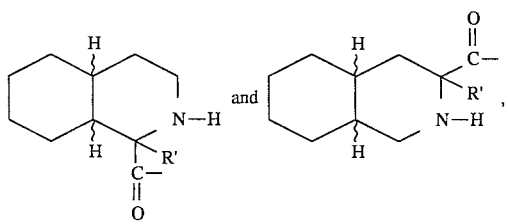

when R' is hydrogen, are referred to at times herein as 1- and 3-perhydro-isoquinolinecarbonyl, respectively, and are respectively abbreviated 1-Piq and 3-Piq. As indicated by the crooked lines, various ring fusion isomers of these substituents exist-this invention contemplates any individual isomer and combinations thereof.

The group

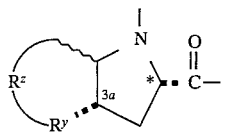

represents a saturated bicyclic system of the 4,5; 5,5; 6,5; 7,5; or 8,5 type. The stereochemistry at 3a is cis to the carbonyl; the other bridgehead bond may be either cis or trans except for the 4,5 and 5,5 systems must be cis at the bridgehead. The definitions of $R^y$ and $R^z$ provide that the variable ring, which includes the three carbon atoms shown, is a saturated carbocyclic system of 4–8 atoms. All of the ring atoms may be carbon, or one of the ring atoms may be a hetero atom selected from —O—, —S—, and —NH—. This definition includes the preferred moiety derived from octahydroindole-2-carboxylic acid, abbreviated "Ohi", as represented by

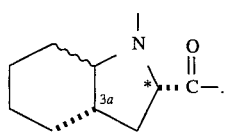

The various cis and trans forms of this moiety are contemplated by this invention.

The group

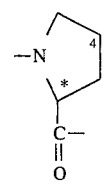

is referred to as prolinyl and is abbreviated Pro.

The asterisks in Formula I and substituent Y denote a chiral center that is (L). The asterisk in substituent X denotes a chiral center that is (D) or (DL).

In addition, diastereomers may exist depending upon branching of alkyl substituents. The compounds of the present invention include mixtures of two or more diastereomers as well as each individual isomer.

Preferred compounds of the present invention include those compounds of Formula I where X is

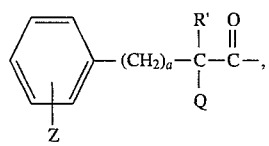

homoprolinyl, 1- or 3-Tiq, or 1- or 3-Piq, and Y is substituted prolinyl or Ohi, and pharmaceutically acceptable salts and solvates thereof. In particular, compounds wherein Q is NHA and A is a sulfonamide (e.g., A=R"SO$_2$—), R' is hydrogen, and B is hydrogen are all preferred. Also, those compounds wherein R is $C_1$-$C_6$ alkyl or Ar—O— are preferred.

Particularly preferred compounds of the present invention include those compounds of Formula I where X is N-ethylsulfonyl-D-phenylglycyl, N-ethylsulfonyl-D-phenylalanyl, N-(carboxymethyl)-D-phenylalanyl, D-homoprolinyl or D-cis[4aS,8aS]-perhydroisoquinoline-1-carbonyl. Also particularly preferred compounds include those compounds of Formula I where Y is (S)-cis-octahydroindole-2-carbonyl.

Preferred compounds of the invention include those described herein as Examples 1, 2, 7, 15 and 17, as well as 20, 22, 23 and 24.

As mentioned above, the invention includes pharmaceutically acceptable salts of the compounds defined by the above Formula I. A particular compound of this invention can possess one or more sufficiently basic functional groups, and accordingly react with any of a number of inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and sulfuric acid.

The compounds of the present invention are known to form hydrates and solvates with appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, A Guidebook to Mechanism in Organic Chemistry, 6th Ed (1986, John Wiley & Sons, New York). As used herein, the term "solvate" includes hydrate forms, such as monohydrates and dihydrates.

A compound of Formula I is prepared by removing simultaneously or sequentially the protecting group(s) P of a corresponding compound of Formula II $$(P)X-(P)Y-\underset{|}{\overset{H}{N}}-\underset{\underset{H}{|}}{\overset{H}{C}}-(CH_2)_3-\underset{|}{\overset{H}{N}}-\overset{NH}{\overset{||}{C}}-NHP \qquad II$$
$$\underset{|}{\overset{|}{C=O}}$$
$$H$$

wherein P on the guanidino group represents an amino protecting group and each of (P)X and (P)Y represents a radical X or Y, respectively, which may bear an independently selected amino protecting group P for a compound of Formula I in which X or Y includes a basic NH moiety and may bear an independently selected carboxy protecting group P for a compound of Formula I in which X or Y includes a carboxy residue; whereafter, when a salt of the compound of Formula I is required, forming the salt with a pharmaceutically acceptable acid. For example, a compound of Formula II in which the amino protecting group(s) is(are) benzyloxycarbonyl and the acid protecting group(s), if present, is(are) benzyl, may be converted into the hydrochloride of the corresponding compound of Formula I by hydrogenolysis at atmospheric pressure over palladium on carbon catalyst in dilute ethanolic hydrochloric acid.

The compounds of Formula I are prepared by known methods of peptide coupling. According to one such method, the acid P—X'—COOH, where —X'—C(O)— has the same meaning as —X— as defined in Formula I, and P is an amino protecting group, if necessary, is coupled with a carboxy protected substituted proline to form the dipeptide (a). For a compound of Formula I in which X includes a carboxy group, P also denotes a carboxy protecting group, which may be in addition to an amino protecting group. The carboxy protecting ester group of the proline moiety is then removed (deblocked or de-esterified) and the free acid form of the dipeptide (b) is coupled with the lactam form of arginine (d). The above reaction sequence is illustrated by the following Scheme 1:

P—X'—COOH + HN—SPro—COO—alk ⎯⎯→

$$\underset{(a)}{P-X'-\overset{\overset{O}{||}}{C}-N-SPro-COO-alk}$$

(a) $\xrightarrow{\text{deesterify}}$ P—X'—$\overset{\overset{O}{||}}{C}$—N—SPro—COOH  (b)

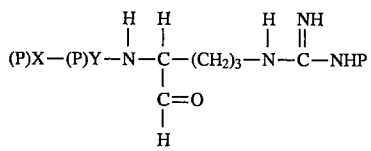

$$\underset{P-X-Y-Arg(P)lactam}{P-X'-\overset{\overset{O}{||}}{C}-N-SPro-CONH-\underset{H}{\overset{\underset{|}{\overset{NHP}{|}}}{\underset{|}{\overset{C=NH}{|}}}}}$$

wherein P represents an amino protecting group, alk is lower alkyl or some similar carboxylic acid protecting group, and SPro is a substituted prolinyl which is the same as Y with the amino and carboxy functionalities visible, i.e., —Y— is the same as —N-SPro-C(O)—. For a compound of Formula I in which Y includes a basic NH moiety or a carboxy group, -SPro- may include a corresponding amino or carboxy protecting group.

The coupled Arg(P) lactam product (c) is reacted with a hydride reducing agent, preferably lithium aluminum hydride or lithium tri-tert-butoxyaluminohydride, in an inert solvent or mixture of solvents to reduce the lactam ring and provide the tripeptide in the arginine aldehyde form represented by the formula P—X¹—C(O)—N-SPro-Arg(p)-H wherein (P) represents amino and carboxy protecting groups.

The protecting groups are removed by procedures known to those skilled in the art such as hydrogenation over a metal catalyst. The protecting groups may be removed from the X-group, from the Y-group and from the arginal group simultaneously or sequentially, depending upon the protecting groups utilized.

The lactam form of arginine is obtained by intramolecular coupling of amino protected arginine. For example, Boc-Arg(Cbz)OH, represented by the formula

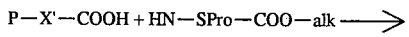

where Boc is t-butyloxycarbonyl and Cbz is benzyloxycarbonyl, is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of further or another tertiary amine base, such as triethylamine or diisopropylethylamine, effects the internal acylation to provide the lactam form of the di-amino protected arginine as shown below

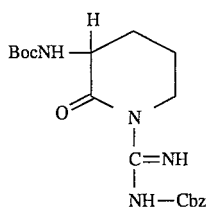

(f)

Prior to use in the coupling with the P—X'(C=O)—NH-SPro-OH as shown in the above scheme, the Boc or other amine protecting group is selectively removed with trifluoroacetic acid or anhydrous HCl to provide the requisite free amino group.

The coupling of an P—X'—COOH compound with a substituted proline carboxylic ester, is carried out by first protecting the amino group of the amino acid, if necessary. Conventional amino protecting groups commonly used for temporary protection or blocking of the amino group are employed.

The amino-protecting group refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, t-butoxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 2,4-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluoroenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group, and the like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the benzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In carrying out the coupling reaction, an ester protecting group for proline is employed which is removable by conditions under which the amino protecting group remains intact. The amino protecting group of the acylating acid P—X'—COOH, if any, thus remains in place for protection of the amino group during the subsequent coupling with the arginine lactam compound to form (c).

The carboxy protecting ester group as used in the specification refers to one of the ester derivatives of the carboxylic acid group commonly employed to block or protect the carboxylic acid group while reactions are carried out on other functional groups on the compound. Examples of such carboxylic acid protecting groups include $C_1$–$C_4$ alkyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below.) Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of Formula I can also be prepared by first synthesizing an SPro-Arg dipeptide precursor and then reacting with a protected X-reactant. According to one such method, the cyclic lactam form of arginine (d) is prepared and coupled with an amino protected substituted proline (g) as shown below to afford the dipeptide (h).

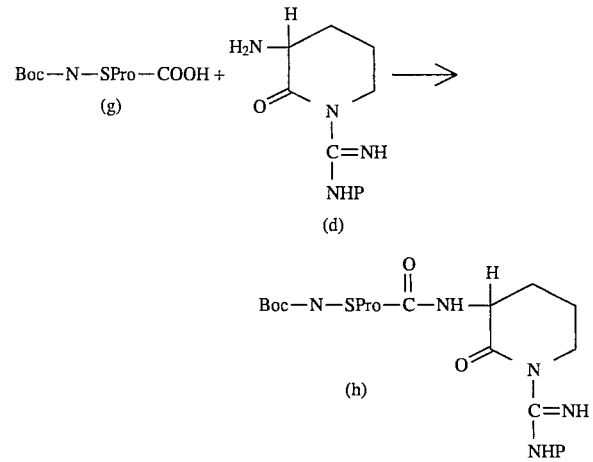

where P represents an amino protecting group such as the benzyloxycarbonyl (Cbz) group, t-butoxycarbonyl (Boc), p-toluenesulfonyl, and the like. Preferably the amino protecting group used is removable by hydrogenation or treatment with mild acid (e.g. trifluoroacetic acid) or a strong acid (e.g. HCl). Examples of other suitable amino protecting groups are provided in "Protective Groups in Organic Synthesis", Second Edition, by T. W. Greene and Peter G. M. Wuts, Chapter 7, page 309–405 (1991), John Wiley & Sons, Inc., publishers. The Boc, or other suitable protecting group, is removed from the proline ring nitrogen which is then acylated with the desired amino acid acyl group to afford the tripeptide shown below.

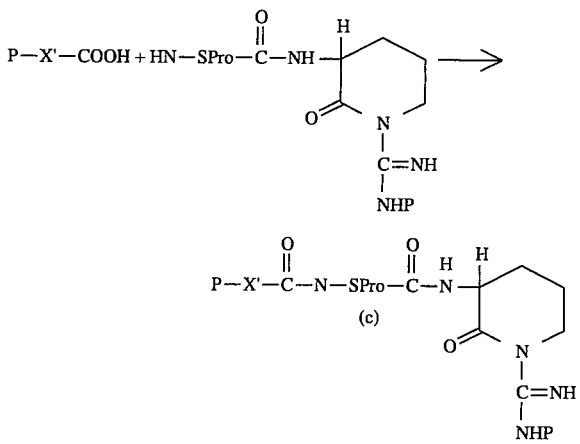

The coupled Arg(P) lactam product (c) is reduced and the protecting groups are removed as described earlier.

The coupling of an P—X'—COOH compound is carried out by first protecting the amino group of the amino acid, if any. Conventional amino protecting groups commonly used for temporary protection or blocking of the amino group are employed. Examples of such protecting groups are described above.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents or a mixture of such solvents. Generally anhydrous conditions are used when, in the coupling reaction, an active ester of the acylating acid is used.

The compounds of the invention are isolated best in the form of acid addition salts. Salts of the compounds of Formula I formed with acids such as those mentioned above are useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalenesulfonic acid may be so used.

The preferred method for purifying the compounds of Formula I, while at the same time preparing a desired stable salt form, is that described in U.S. Pat. No. 5,250,660. According to the method, stable sulfates or hydrochlorides are provided by preparative purification over $C_{18}$ reversed-phase chromatography in which the aqueous component comprises sulfuric acid or hydrochloric acid at pH 2.5 and acetonitrile as the organic component. The pH of the acidic eluant is adjusted to between about pH 4 and about 6 with an anion exchange resin in the hydroxyl form, e.g. Bio-Rad AG-1X8. After adjustment of the pH, the solution of tripeptide sulfate or hydrochloride salt is lyophilized to provide the pure salt in dry powder form. In an example of the process, crude D-hPro(4-cis-phenoxy)Pro-Arg-H sulfate is dissolved in water and the solution is loaded on a Vydac $C_{18}$ RP-HPLC 5 cm×50 cm column. A gradient of 2–30% B (A=0.01% $H_2SO_4$; B=acetonitrile) over 4 hours is used. Multiple fractions are collected and those containing product as determined by analytical RPHPLC are pooled. The pH of the pooled fractions is adjusted to pH 4.0–4.5 with AG-1X8 resin in hydroxide form (Bio-Rad, 3300 Ragatta Blvd., Richmond, Calif. 94804). The solution is filtered and the filtrate is lyophilized to provide the pure D-,L-,L-tripeptide in the form of the sulfate salt.

The optically active isomers of the diastereomers of the X moiety are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The 4-substituted proline derivatives (Y=—N-SPro-CO—) used for making the compounds of this invention are all of the cis configuration of the 4-substituent relative to the carbonyl moiety. Intermediates for introducing this functionality into the compounds of Formula I are made by standard techniques.

For example, 4-substituted proline derivatives in which the R group contains a methylene group at the point of attachment to the proline ring can be prepared in the following manner:

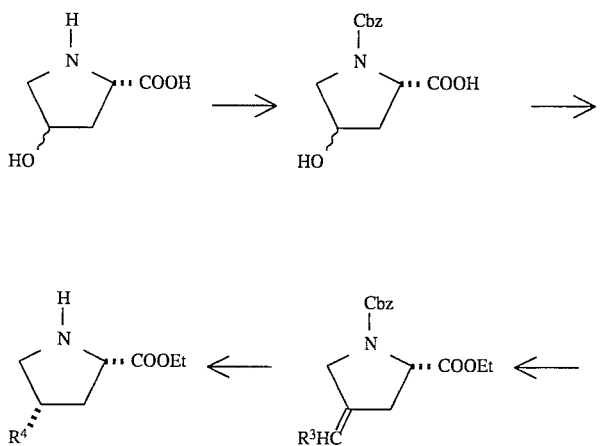
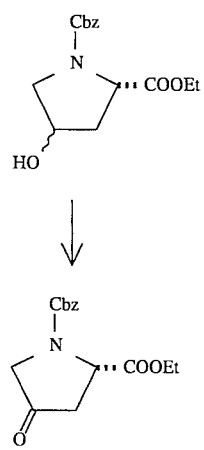

where $R^4=R^3CH_2=$an R group containing a methylene group at the point of attachment to the proline ring.

A 4-hydroxyproline (both the cis and trans forms are commercially available) is first protected with an amino-protecting group—the Cbz group is particularly useful in this sequence. The resulting intermediate is then esterified (the methyl or especially ethyl esters are especially convenient) and then oxidized to give the corresponding ketone. This oxidation is accomplished under any of a number of oxidation conditions such as Jones oxidation or pyridinium chlorochromate; especially useful for this transformation is the use of pyridinium chlorochromate in a dry, non-reactive solvent such as dichloromethane. When allowed to react for 8–16 hours, this reaction is generally complete when performed at ambient temperature. This versatile ketone intermediate is then allowed to react with an appropriate Wittig reagent to give the desired olefin. Typically the appropriate R-substituted triphenylphosphonium halide is added to a dry inert solvent (e.g., tetrahydrofuran) which contains a strong base (e.g., potassium t-butoxide). The ketone is introduced and after approximately three hours at ambient temperature the desired olefin intermediate can be isolated. In order to obtain good yields of the olefin, it is preferred that a 0.4–0.6 molar excess of the Wittig reagent be employed relative to the ketone. The olefin is then reduced to the desired R-substituted proline by standard reduction techniques. Catalytic hydrogenation is the most facile method for accomplishing this transformation in the laboratory. Hydrogenation of the olefin in the presence of a catalyst (e.g., 5% palladium on carbon) in an inert solvent such as ethanol will be effective at atmospheric pressure. In the case of those intermediates in which the amino-protecting group is Cbz, hydrogenation also removes the protecting group which provides a compound which can be used for coupling to P—X'—COOH. As will be appreciated by those skilled in this art, this process will not be effective for preparing compounds where the R group is attached to the proline ring through a hetero atom or are an aromatic ring. Thus, in the above scheme, $R^4$ will be alkyl, aralkyl (e.g., benzyl), (cycloalkyl)alkyl, etc.

A related method for preparing these intermediates is summarized by the following scheme:

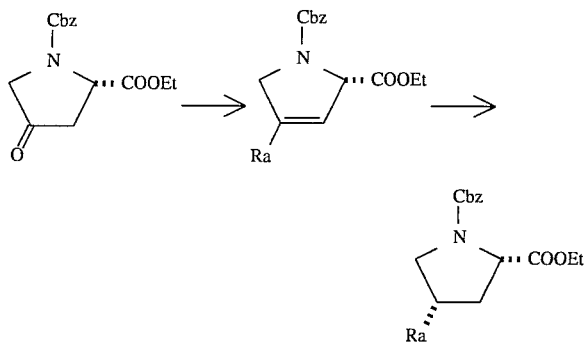

The above reaction scheme is an alternative to the Wittig reaction described earlier and is useful for preparing compounds for which Wittig reagents cannot be prepared. Thus, for preparing intermediates wherein Ra is alkyl, phenyl, and the like, the pyrrolidinone intermediate is allowed to react with an appropriate Grignard reagent. Typically a slight molar excess of the Grignard reagent is employed, usually at low temperatures (e.g., −80° to −60° C.) and a low freezing inert solvent such as tetrahydrofuran. After addition of the reagents, the reaction mixture can be permitted to warm to room temperature, after which time the reaction is usually complete within several hours. The resulting intermediate is dehydrated, for example, by treatment with trifluoroacetic acid (see, e.g., Example 6A). The 3,4-dehydro intermediate is then reduced to the desired cis intermediate using the same reductive conditions as described above for reduction of the olefin intermediate.

Intermediates wherein the hetero "L"-group is oxygen and is attached directly to the proline ring (i.e., p=0) can be prepared employing the Mitsunobu reaction (Mitsunobu, *Synthesis*, 1 (1981)):

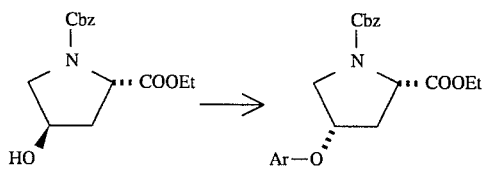

In this reaction, the trans hydroxypyrrolidinecarboxylic ester is treated with triphenylphosphine in a solvent such as tetrahydrofuran in the presence of Ar—O—H. The mixture is cooled to approximately 0° C. and diethylazodicarboxylate is added. After warming to room temperature, the reaction is worked up to provide the desired cis intermediate. While the scheme above depicts the reaction for compounds where L=—O—, p=q=0, and T'=Ar, this sequence is useful for preparing other compounds where p=0 and L is —O—.

Intermediates wherein L is sulfur and is attached directly to the ring can be prepared by first converting the hydroxy group to a tosylate or other similar leaving group and then displacing with a thiolate anion (see, e.g., Krapcho, et al., *J. Med. Chem.*, 31, 1148–1160 (1988); Smith, et al., *J. Med. Chem.*, 31, 875–855 (1988)).

Intermediates wherein L is nitrogen and is attached directly to the ring can be prepared by first converting the hydroxy group to a tosylate or other similar leaving group and then displacing with azide. The azide can be reduced using known methods and then alkylated to provide the desired functionality (see, e.g., Smith, et al., *J. Med. Chem.*, 31, 875–855 (1988)).

The compounds of this invention containing a cis-Ohi functionality are prepared by preparing (S)-indoline carboxylic acid ethyl ester from the corresponding acid (see, Vincent, et al., *Drug Design and Discovery*, Vol. 9, pp 11–28 (1992)), and reducing this intermediate by hydrogenation over 5% Pd/C in ethanol (see Example 7B) to give the octahydroindole-2-carboxylic acid ester, generally referred to as Ohi-ester as summarized below.

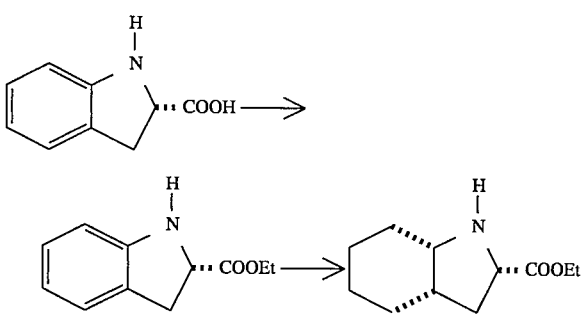

The compounds of this invention containing a trans-Ohi functionality are prepared by the method of Vincent, et al., *Drug Design and Discovery*, Vol. 9, pp 11–28 (1992)). This is summarized in the scheme shown below:

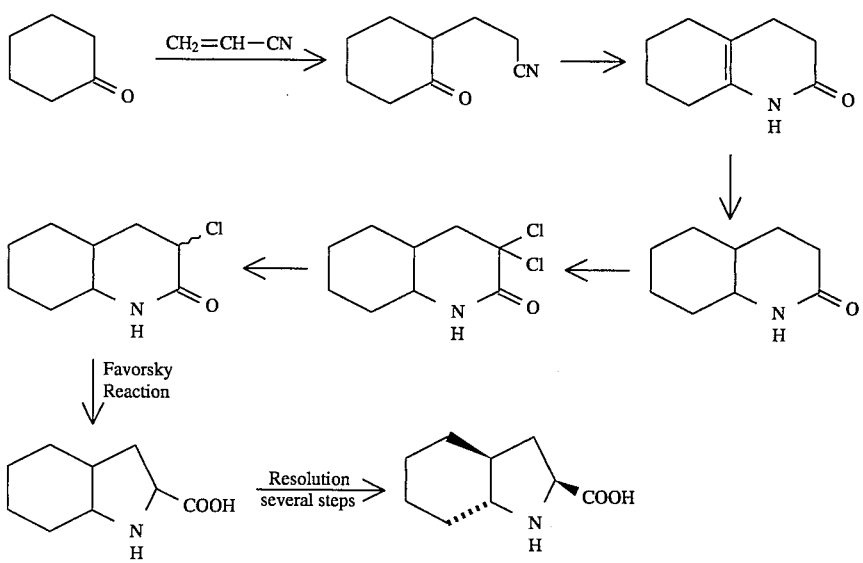

The compound of this invention containing a bicyclic system (with or without heteroatom) can be prepared by the method of Teetz, et al., *Tetrahedron Letters*, 25, 4479 (1984). Generally:

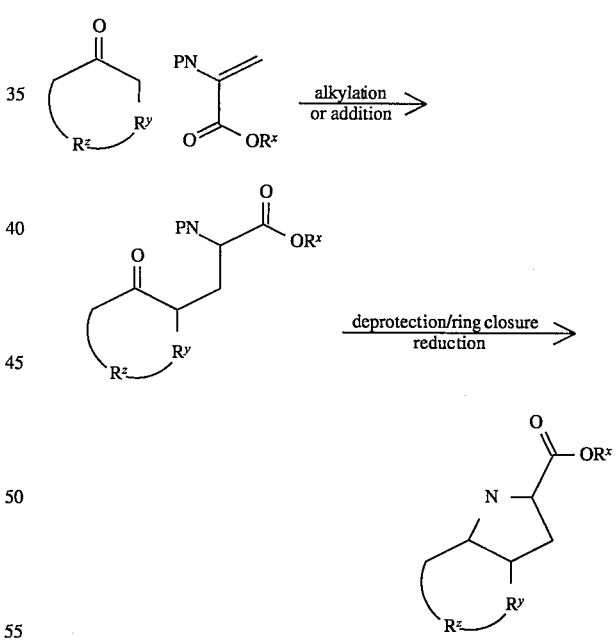

where P is a protecting group and $R^x$ is alkyl.

Many of the final compounds of this invention or intermediates thereto can be interconverted by standard techniques. For example, aryl compounds which are substituted with nitro can be reduced (e.g., in the presence of sodium hydrosulfite in a non-reactive solvent, such as ethanol, water, or a mixture thereof). When the nitro compound is heated at reflux in a water/ethanol mixture in the presence of sodium hydrosulfite, reduction is usually complete within several hours. The resulting amine may be present in the final product; if the amine is present in an intermediate, it may be desirable to convert it to its final desired form (e.g., acylation to provide the acylated amine) or protected to avoid side reactions during the subsequent chemistry. If the free amine is the desired compound, the Cbz protecting group is particularly useful in this regard. Other transformations and intraconversions of this type will be apparent to skilled organic chemists.

The following Examples are provided to further describe the invention and are not to be construed as limitations thereof.

The abbreviations used in this specification have the following meanings.

Amino acid residues: Arg=arginyl, Pro=prolinyl, hPro=homoprolinyl, Phg=phenylglycinyl, Phe=phenylalanyl, Cha=β-cyclohexylalaninyl, Chg=cyclohexylglycinyl, Abo=2-azabicyclo[3.3.0]octane-3-carbonyl, 1-Piq=perhydroisoquinoline-1-carbonyl, 3-Piq=perhydro-isoquinoline-3-carbonyl.

Boc=t-butyloxycarbonyl
Bn=benzyl
Cbz=benzyloxycarbonyl
DCC=dicyclohexylcarbodiimide
DMF=dimethylformamide
DMSO=dimethylsulfoxide
EtOAc=ethyl acetate
Et$_2$O=diethyl ether
EtOH=ethanol
FAB-MS=fast atom bombardment mass spectrum
FD-MS=field desorption mass spectrum
HOBT=1-hydroxybenzotriazole hydrate
Ph=phenyl
RPHPLC=Reversed Phase High Performance Liquid Chromatography
TFA=trifluoroacetic acid
THF=tetrahydrofuran
TLC=thin layer chromatography The following parameters for RPHPLC were employed: Solvent A: 0.05% aqueous hydrochloric acid (1.5 mL concentrated hydrochloric acid in 3 L water); Solvent B: acetonitrile; Column: Vydac C$_{18}$-5 cm×25 cm; Flow rate: 10 mL/minute; Method A: 98:2 (A/B), linear ramp to 70:30 (A/B) over 4 hours; Method B: 98:2 (A/B), linear ramp to 90:10 (A/B) over 4 hours.

Unless otherwise stated, pH adjustments and work up are with aqueous acid or base solutions.

EXAMPLE 1

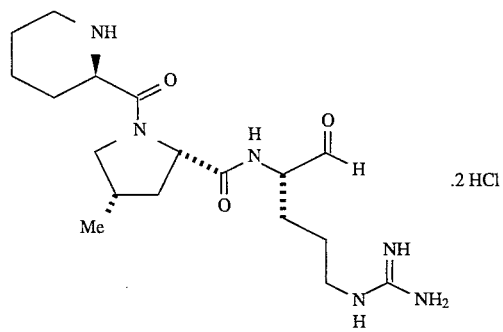

Synthesis of D-hPro-Pro(4-cis-methyl)-ArgH.2 HCl
(D-homoprolyl-L-cis-4-methyl-prolyl-L-argininal dihydrochloride)

A) Preparation of Cbz-Pro(4-trans-OH)-OEt.

To a solution of Cbz-Pro(4-trans-OH)-OH (33 g, 124 mmol) in ethanol (500 mL) was added p-toluenesulfonic acid (1 g) and the solution was heated to reflux (16 hours). After cooling to room temperature, the solvent was removed in vacuo. The residue was dissolved in ethyl acetate (400 mL) and washed twice with saturated aqueous NaHCO$_3$, and twice with a saturated aqueous sodium chloride solution. The ethyl acetate solution was dried with MgSO$_4$, filtered and concentrated in vacuo to give 34.5 g (95%) of a colorless oil.

$^1$H NMR
FD-MS m/e 293 (M$^+$)
Analysis for C$_{15}$H$_{19}$NO$_5$: Calc: C, 61.42; H, 6.53; N, 4.77; Found: C, 61.20; H, 6.65; N, 4.73.

B) Preparation of Cbz-Pro(4-oxo)-OEt.

Cbz-Pro(4-trans-OH)—OEt (32.7 g, 111 mmol) was dissolved in dichloromethane (500 mL) with mechanical stirring in a 1 L round bottom flask. To this solution was added 3 Å molecular sieves (100 g) and pyridinium chlorochromate (60 g, 278 mmol), in portions small enough to maintain efficient stirring. After stirring for 12 hours at room temperature, diethyl ether (200 mL) was added and the black slurry was decanted from a tarry residue and flushed through a column of silica gel (200 g). The residue was washed twice with dichloromethane (200 mL) and the combined washings were also passed through the silica plug. The filtrate was flushed through a silica gel column with 1:1 ethyl acetate/hexanes (4 L) and 500 mL fractions were collected. All fractions containing product, as judged by TLC, were combined and concentrated in vacuo to give 23.8 g (74%) of a colorless oil.

$^1$H NMR
FD-MS m/e 291 (M$^+$)
Analysis for C$_{15}$H$_{17}$NO$_5$: Calc: C, 61.85; H, 5.88; N, 4.81; Found: C, 61.57; H, 5.82; N, 4.71.

C) Preparation of Cbz-Pro(4-methylene)-OEt.

Potassium t-butoxide (12.6 g, 112.5 mmol) was suspended in tetrahydrofuran (400 mL) in an oven dried 2-neck 1 L round bottom flask equipped with a nitrogen inlet, magnetic stir bar, and addition funnel. To this suspension was added, in several portions, methyl triphenylphosphonium bromide (40.2 g, 112.5 mmol). After stirring for 15 minutes, a solution of Cbz-Pro(4-oxo)-OEt (23.4 g, 80.3 mmol) in tetrahydrofuran (150 mL) was added dropwise via an addition funnel over a 1 hour period. After stirring for an additional 2 hours, saturated aqueous NH$_4$Cl (100 mL) was added. This solution was diluted with ethyl acetate (750 mL) and the layers were separated. The organic layer was washed two times with 1N citric acid, twice with saturated aqueous NaHCO$_3$, and twice with a saturated aqueous sodium chloride solution. The organic solution was dried with MgSO$_4$, filtered and concentrated to give a yellow oil. This oil was purified by flash chromatography over silica gel, eluting with 2:1 hexanes/ethyl acetate. Fractions containing product (as judged by TLC) were combined and concentrated in vacuo to give 9.8 g (42%) of a colorless oil.

$^1$H NMR
FD-MS m/e 289 (M$^+$)
Analysis for C$_{16}$H$_{19}$NO$_4$: Calc: C, 66.42; H, 6.62; N, 4.84; Found: C, 66.48; H, 6.66; N, 4.85.

D) Preparation of Pro(4-cis-methyl)-OEt.HCl.

To a solution of Cbz-Pro(4-methylidene)-OEt (9.6 g, 33.2 mmol) in ethanol (500 mL) was added 5% Pd/C (2 g). Nitrogen gas was bubbled through this solution for 5 minutes and then hydrogen gas was bubbled through for 3 hours. The solution was filtered off over a pad of diatomaceous earth. Hydrogen chloride gas was then bubbled through the solution until saturation, and then the solution was concentrated in vacuo to give 5.8 g (91%) of a white solid.

$^1$H NMR

FD-MS m/e 158 (MH$^+$)

Analysis for C$_8$H$_{16}$NO$_2$Cl: Calc: C, 49.61; H, 8.33; N, 7.23; Found: C, 49.36; H, 8.45; N, 7.25.

E) Preparation of Cbz-D-hPro-OH.

D-hPro-OH (5.0 g, 38.7 mmol) was dissolved in tetrahydrofuran (100 mL) and water (30 mL). The pH of the solution was adjusted to 9.5 with 2N NaOH and benzyl chloroformate (5.5 mL, 38.7 mmol) was added dropwise while maintaining the pH at 9.5 with 2N NaOH. The reaction was stirred for an additional 1 hour at room temperature. The organic solvent was evaporated in vacuo, diethyl ether (100 mL) and water (50 mL) was added to the residue. The aqueous layer was separated, the pH of the solution was adjusted to 2.8 with 3N HCl, and ethyl acetate (150 mL) was added. The organic layer was separated and dried (MgSO$_4$); the filtrate was concentrated in vacuo to give 9.6 g (95%) of a clear oil.

$^1$H NMR

FD-MS m/e 264 (MH$^+$)

F) Preparation of Cbz-D-hPro-Pro(4-cis-methyl)-OEt.

To a solution of Cbz-D-hPro-OH (8.23 g, 31.2 mmol), Pro(4-cis-methyl)-OEt.HCl (5.5 g, 28.4 mmol), 1-hydroxybenzotriazole (4.2 g, 31.2 mmol), and N,N-diisopropylethylamine (12.4 mL, 71 mmol) in dichloromethane (300 mL) was added 1-(3-dimethylaminopropyl)-3-ethylcarbodiimide hydrochloride (6.8 g, 35.5 mmol). After stirring for 14 hours, the solvent was removed by rotary evaporation, and the residue was dissolved in ethyl acetate (500 mL), and washed twice with 1N citric acid (200 mL), twice with saturated aqueous NaHCO$_3$, and twice with a saturated aqueous sodium chloride solution. The combined ethyl acetate extracts were dried with MgSO$_4$, filtered, and concentrated in vacuo to give a yellow oil which was purified by chromatography over silica gel, eluting with 2:1 hexanes/ethyl acetate. The product containing fractions as judged by TLC were combined and concentrated in vacuo to give 11.08 g (97%) of a thick oil.

$^1$H NMR

FD-MS m/e 402 (M$^+$)

Analysis for C$_{22}$H$_{30}$N$_2$O$_5$: Calc: C, 65.65; H, 7.51; N, 6.96; Found: C, 65.40; H, 7.52; N, 7.19.

G) Preparation of Cbz-D-hPro-Pro(4-cis-methyl)-OH.

To a solution of Cbz-D-hPro-Pro(4-cis-methyl)-OEt (8.05 g, 20 mmol) in p-dioxane (200 mL) was added a solution of LiOH.H$_2$O (3.4 g, 80 mmol) in water (100 mL) with vigorous stirring. After stirring for 3 hours, the solution was concentrated to a volume of 50 mL, diluted with water (100 mL), and extracted twice with diethyl ether (200 mL). The aqueous phase was adjusted to pH 2 with 5N aqueous HCl and extracted three times with ethyl acetate (150 mL). The combined ethyl acetate extracts were dried with MgSO$_4$, filtered, and concentrated to give 7.8 g (104%) of a white solid.

$^1$H NMR

FD-MS m/e 375 (MH$^+$)

Analysis for C$_{20}$H$_{26}$N$_2$O$_5$: Calc: C, 64.16; H, 7.00; N, 7.48; Found: C, 63.95; H, 7.27; N, 7.47.

H) Preparation of Boc-Arg(Cbz)-OH.

Boc-Arg-OH.HCl (82.1 g, 250 mmol) was dissolved in 5N NaOH (240 mL) in a 3 necked flask. The reaction mixture was chilled to –5° C. and the pH was maintained at 13.2–13.5 using 5N NaOH (250 mL) while adding benzyl chloroformate (143 mL, 1.0 mol) dropwise (55 minutes). The reaction mixture was stirred for an additional 1 hour at –5° C. and diluted with water (100 mL) and diethyl ether (500 mL). The aqueous layer was separated and extracted twice with diethyl ether (500 mL). The aqueous layer was then acidified to pH 3.0 with 3N H$_2$SO$_4$ (560 mL) and extracted with ethyl acetate (550 mL). The aqueous layer was separated and extracted once with ethyl acetate. The combined ethyl acetate layers were washed with water, dried (MgSO$_4$) and concentrated in vacuo to give 66.1 g (65%) of a white solid.

$^1$H NMR

FD-MS 408 (M$^+$)

I) Preparation of Boc-Arg(Cbz)-Lactam.

Boc-Arg(Cbz)-OH (66.0 g, 0.162 mol) was dissolved in tetrahydrofuran (230 mL) and cooled to –10° C. To this solution was added N-methylmorpholine (18.7 mL, 0.17 mol) followed by isobutyl chloroformate (22.5 mL, 0.17 mol). After stirring 5 minutes at –10° C., triethylamine (23.5 mL, 0.17 mol) was added. After an additional 1 hour at –10° C., the mixture was allowed to warm to room temperature and stirring continued for 1 hour at room temperature. The reaction mixture was then poured into 1 L of ice-water and the resulting precipitate was filtered, washed with cold water, and dried in vacuo. The product was crystallized from ethyl acetate to give 38 g (60%) of a white solid.

$^1$H NMR

FD-MS 391 (MH$^+$)

J) Preparation of Arg(Cbz)-Lactam.2 HCl.

A solution of HCl(g) saturated ethyl acetate (7.2 L) was added dropwise over 30 minutes to a solution of Boc-Arg(Cbz)-Lactam (641 g, 1.64 mol) dissolved in dichloromethane (3 L) at –10° C. After 1 hour at –10° C. the cold bath was removed and the solution was allowed to warm to room temperature over 3 hours. Diethyl ether (12 L) was added and the resulting precipitate was filtered, washed with diethyl ether, and dried in vacuo to give 580 g (97%).

FD-MS 291 (MH$^+$)

K) Preparation of Cbz-D-hPro-Pro(4-cis-methyl)Arg(Cbz)lactam.

In flask 1, Cbz-D-hPro-Pro(4-cis-methyl)-OH (6 g, 16 mmol) was dissolved in tetrahydrofuran (100 mL), cooled to –15° C. and N-methylmorpholine (1.8 mL, 16 mmol) was added, followed by isobutyl chloroformate (2.1 mL, 16 mmol). The reaction mixture was allowed to stir at –15° C. for 2 minutes.

In flask 2, Arg(Cbz)-Lactam.2HCl (7.3 g, 20 mmol) was dissolved in dimethylformamide (100 mL), cooled to 0° C., and N,N-diisopropylethylamine (8.4 mL, 48 mmol) was added. The reaction mixture was allowed to stir at 0° C. for 2 minutes.

The contents of flask 2 were added to flask 1 in one portion and the reaction mixture was allowed to stir for 4 hours at –15° C. The cold bath was then removed and the reaction mixture was allowed to slowly warm to room temperature (24 hours). Then 1N NaHCO$_3$ (5 mL) was added and the solvent was removed in vacuo. The residue was partitioned between ethyl acetate (300 mL) and water (150 mL). The organic layer was separated, and washed sequentially with 1N NaHCO$_3$, water, 1N citric acid, and water. The organic layer was dried (MgSO$_4$), and the filtrate was concentrated in vacuo. The residue was chromatographed over silica gel, eluting with a step gradient of 50% ethyl acetate/hexanes through ethyl acetate. The product containing fractions, as determined by TLC, were combined and concentrated to give 5.9 g (57%) of a white foam.

$^1$H NMR

FD-MS m/e 647 (MH$^+$)

Analysis for C$_{34}$H$_{42}$N$_6$O$_7$: Calc: C, 63.14; H, 6.55; N, 12.99; Found: C, 63.08; H, 6.68; N, 12.94.

L) Preparation of D-hPro-Pro(4-cis-methyl)-ArgH.2 HCl.

To a stirring solution of Cbz-D-hPro-Pro(4-cis-methyl)-Arg(Cbz)lactam (4.5 g, 7 mmol) in tetrahydrofuran (100 mL) at −23° C., was slowly added a solution of 1N LiAl(O-t-Bu)$_3$H (8.7 mL, 8.7 mmol) in tetrahydrofuran. After 2.5 hours, the reaction mixture was poured into a stirring solution of cold 1N H$_2$SO$_4$ (50 mL). The solution was then diluted with water (100 mL), hexanes (100 mL), and tetrahydrofuran (25 mL). The layers were separated and the aqueous phase was saturated with solid NaCl, and extracted three times with ethyl acetate (200 mL). The combined ethyl acetate extracts were washed with saturated aqueous NaCl (50 mL), dried (MgSO$_4$), and concentrated in vacuo to give 4.4 g of white foam.

The foam was then dissolved in ethanol (200 mL) and water (80 mL) and 1N HCl (20 mL) was added. To this stirring solution was then added 5% Pd-on-carbon (1.4 g). Hydrogen gas was then bubbled through the solution for 4 hours, and then the reaction was flushed with nitrogen and filtered over a pad of diatomaceous earth. The ethanol was removed in vacuo at 30° C. and then the residue was redissolved in water (50 mL). The pH of the aqueous solution was adjusted to 4 with Bio Rad ion exchange resin (basic form), filtered and lyophilized to give 2.6 g (83%) of a white solid. RPHPLC method A was used to purify 2.0 g of this material and 1.56 g (78%) of pure D-hPro-Pro-(4-cis-methyl)-ArgH.2 HCl were isolated.

$^1$H NMR

FAB-MS m/e 381 (MH$^+$)

Analysis for $C_{18}H_{32}N_6O_3$.2 HCl.H$_2$O: Calc: C, 45.86; H, 7.70; N, 17.83; Found: C, 45.86; H, 7.99; N, 17.88.

EXAMPLE 2

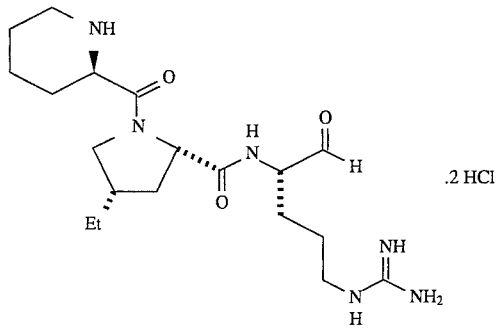

Synthesis of D-hPro-Pro(4-cis-ethyl)-ArgH.2 HCl
(D-homoprolyl-L-cis-4-ethyl-prolyl-L-argininal dihydrochloride)

A) Preparation of Cbz-Pro(4-methyl-methylidene)-OEt.

By a method substantially equivalent to that described in Example 1-C, 10.3 g (40%) of Cbz-Pro(4-methyl-methylidene)-OEt were prepared from Cbz-Pro(4-oxo)-OEt and ethyl triphenylphosphonium bromide.

$^1$H NMR

FD-MS m/e 303 (M$^+$)

Analysis for $C_{17}H_{21}NO_4$: Calc: C, 67.31; H, 6.98; N, 4.62; Found: C, 67.56; H, 7.23; N, 4.91.

B) Preparation of Pro(4-cis-ethyl)-OEt.HCl.

By a method substantially equivalent to that described in Example 1-D, 5.5 g (80%) of Pro(4-cis-ethyl)-OEt.HCl were prepared from Cbz-Pro(4-methyl-methylidene)-OEt.

$^1$H NMR

FD-MS m/e 172 (MH$^+$)

Analysis for $C_9H_{18}NO_2Cl$: Calc: C, 52.05; H, 8.73; N, 6.74; Found: C, 51.93; H, 8.82; N, 6.66.

C) Preparation of Cbz-D-hPro-Pro(4-cis-ethyl)-OEt.

By a method substantially equivalent to that described in Example 1-F, 10.4 g (95%) of Cbz-D-hPro-Pro(4-cis-ethyl)-OEt were prepared from Cbz-D-hPro-OH and Pro(4-cis-ethyl)-OEt.HCl.

$^1$H NMR

FD-MS m/e 416 (M$^+$)

Analysis for $C_{23}H_{32}N_2O_5$: Calc: C, 66.32; H, 7.74; N, 6.73; Found: C, 66.07; H, 7.75; N, 7.00.

D) Preparation of Cbz-D-hPro-Pro(4-cis-ethyl)-OH.

By a method substantially equivalent to that described in Example 1-G, 6.9 g (92%) of Cbz-D-hPro-Pro(4-cis-ethyl)-OH were prepared.

$^1$H NMR

FD-MS m/e 389 (MH$^+$)

Analysis for $C_{21}H_{28}N_2O_5$: Calc: C, 64.93; H, 7.26; N, 7.21; Found: C, 64.71; H, 7.44; N, 7.31.

E) Preparation of Cbz-D-hPro-Pro(4-cis-ethyl)Arg(Cbz)lactam.

By a method substantially equivalent to that described in Example 1-K, 6.6 g (70%) of Cbz-D-hPro-Pro(4-cis-ethyl)Arg(Cbz)lactam were prepared from Cbz-D-hPro-Pro(4-cis-ethyl)-OH and Arg(Cbz)lactam.2 HCl.

$^1$H NMR

FD-MS m/e 661 (M$^+$)

Analysis for $C_{35}H_{44}N_6O_7$: Calc: C, 63.62; H, 6.71; N, 12.72; Found: C, 63.88; H, 6.69; N, 12.43.

F) Preparation of D-hPro-Pro(4-cis-ethyl)-ArgH.2 HCl.

By a method substantially equivalent to that described in Example 1-L, 3 g (85%) of crude D-hPro-Pro(4-cis-ethyl)-ArgH.2 HCl were prepared from Cbz-D-hPro-Pro(4-cis-ethyl)-Arg(Cbz)lactam. RPHPLC method A was used to purify 2.0 g of this material and 1.7 g (85%) of pure D-hPro-Pro(4-cis-ethyl)-ArgH.2 HCl were isolated.

$^1$H NMR

FAB-MS m/e 395 (MH$^+$)

Analysis for $C_{19}H_{34}N_6O_3$.2 HCl.H$_2$O: Calc: C, 47.01; H, 7.89; N, 17.31; Found: C, 47.29; H, 8.05; N, 17.53.

EXAMPLE 3

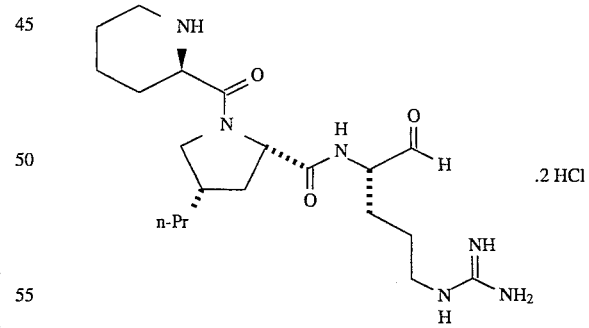

Synthesis of D-hPro-Pro(4-cis-n-propyl)-ArgH.2 HCl

A) Preparation of Cbz-Pro(4-ethyl-methylidene)-OEt.

By a method substantially equivalent to that described in Example 1-C, 9.6 g (35%) of Cbz-Pro(4-ethyl-methylidene)-OEt were prepared from Cbz-Pro(4-oxo)-OEt and n-propyl triphenylphosphonium bromide.

$^1$H NMR

FD-MS m/e 317 (M$^+$)

Analysis for $C_{18}H_{23}NO_4$: Calc: C, 68.12; H, 7.30; N, 4.41; Found: C, 68.05; H, 7.29; N, 4.51.

B) Preparation of Pro(4-cis-n-propyl)-OEt.HCl.

By a method substantially equivalent to that described in Example 1-D, 6.2 g (94%) of Pro(4-cis-n-propyl)-OEt.HCl were prepared from Cbz-Pro(4-ethyl-methylidene)-OEt.

$^1$H NMR

FD-MS m/e 185 (M$^+$)

Analysis for $C_{10}H_{20}NO_2Cl$: Calc: C, 54.17; H, 9.09; N, 6.32; Found: C, 54.10; H, 9.05; N, 6.36.

C) Preparation of Cbz-D-hPro-Pro(4-cis-n-propyl)-OEt.

By a method substantially equivalent to that described in Example 1-F, 10.3 g (87%) of Cbz-D-hPro-Pro(4-cis-n-propyl)-OEt were prepared from Cbz-D-hPro-OH and Pro(4-cis-n-propyl)-OEt.HCl.

$^1$H NMR

FD-MS m/e 430 (M$^+$)

Analysis for $C_{24}H_{34}N_2O_5$: Calc: C, 66.95; H, 7.96; N, 6.51; Found: C, 66.73; H, 8.05; N, 6.55.

D) Preparation of Cbz-D-hPro-Pro(4-cis-n-propyl)-OH.

By a method substantially equivalent to that described in Example 1-G, 6.5 g (81%) of Cbz-D-hPro-Pro(4-cis-n-propyl)-OH were prepared.

$^1$H NMR

FD-MS m/e 403 (MH$^+$)

Analysis for $C_{22}H_{30}N_2O_5$: Calc: C, 65.65; H, 7.51; N, 6.96; Found: C, 65.02; H, 7.49; N, 6.81.

E) Preparation of Cbz-D-hPro-Pro(4-cis-n-propyl)-Arg(Cbz)lactam.

By a method substantially equivalent to that described in Example 1-K, 7 g (76%) of Cbz-D-hPro-Pro(4-cis-n-propyl)Arg(Cbz)lactam were prepared from Cbz-D-hPro-Pro(4-cis-n-propyl)-OH and Arg(Cbz)lactam.2 HCl.

$^1$H NMR

FD-MS m/e 675 (MH$^+$)

Analysis for $C_{36}H_{46}N_6O_7$: Calc: C, 64.08; H, 6.87; N, 12.45; Found: C, 63.82; H, 6.96; N, 12.39.

F) Preparation of D-hPro-Pro(4-cis-n-propyl)-ArgH.2 HCl.

By a method substantially equivalent to that described in Example 1-L, 3.1 g (87%) of crude D-hPro-Pro(4-cis-n-propyl)-ArgH.2 HCl were prepared from Cbz-D-hPro-Pro(4-cis-n-propyl)-Arg(Cbz)lactam. RPHPLC method A was used to purify 2.0 g of this material and 1.9 g (94%) of pure D-hPro-Pro(4-cis-n-propyl)-ArgH.2 HCl were isolated.

$^1$H NMR

FAB-MS m/e 409 (MH$^+$)

Analysis for $C_{20}H_{36}N_6O_3$.3 HCl.H$_2$O: Calc: C, 44.82; H, 7.71; N, 15.68; Found: C, 44.86; H, 7.72; N, 15.67.

EXAMPLE 4

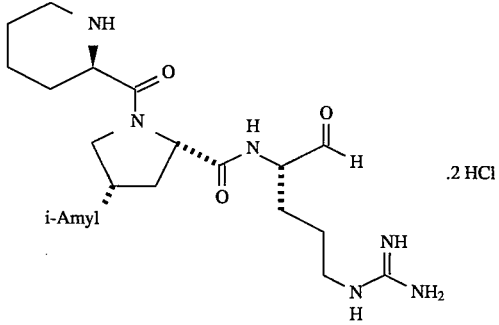

Synthesis of D-hPro-Pro(4-cis-isoamyl)-ArgH.2 HCl
(D-homoprolyl-L-cis-4-isoamyl-prolyl-L-argininal dihydrochloride)

A) Preparation of Cbz-Pro(4-isobutyl-methylidene)-OEt.

By a method substantially equivalent to that described in Example 1-C, 12.8 g (43%) of Cbz-Pro(4-isobutyl-methylidene)-OEt were prepared from Cbz-Pro(4-oxo)-OEt and isoamyl triphenylphosphonium bromide.

$^1$H NMR

FD-MS m/e 345 (M$^+$)

Analysis for $C_{20}H_{27}NO_4$: Calc: C, 69.54; H, 7.88; N, 4.05; Found: C, 69.74; H, 7.85; N, 3.99.

B) Preparation of Pro(4-cis-isoamyl)-OEt.

By a method substantially equivalent to that described in Example 1-D, 9.2 g (84%) of Pro(4-cis-isoamyl)-OEt were prepared from Cbz-Pro(4-isobutyl-methylidene)-OEt. In this case, HCl precipitation produced an oil, so the compound was isolated as the free base.

$^1$H NMR

FD-MS m/e 214 (M$^+$)

Analysis for $C_{12}H_{23}NO_2$: Calc: C, 67.57; H, 10.87; N, 6.57; Found: C, 67.38; H, 10.76; N, 6.73.

C) Preparation of Cbz-D-hPro-Pro(4-cis-isoamyl)-OEt.

By a method substantially equivalent to that described in Example 1-F, 11.3 g (82%) of Cbz-D-hPro-Pro(4-cis-isoamyl)-OEt were prepared from Cbz-D-hPro-OH and Pro(4-cis-isoamyl)-OEt.

$^1$H NMR

FD-MS m/e 459 (M$^+$)

Analysis for $C_{26}H_{38}N_2O_5$: Calc: C, 68.10; H, 8.35; N, 6.11; Found: C, 68.09; H, 8.11; N, 6.37.

D) Preparation of Cbz-D-hPro-Pro(4-cis-isoamyl)-OH.

By a method substantially equivalent to that described in Example 1-G, 7.9 g (91%) of Cbz-D-hPro-Pro(4-cis-isoamyl)-OH were prepared.

$^1$H NMR

FD-MS m/e 431 (MH$^+$)

Analysis for $C_{24}H_{34}N_2O_5$: Calc: C, 66.95; H, 7.96; N, 6.51; Found: C, 67.17; H, 8.19; N, 6.33.

E) Preparation of Cbz-D-hPro-Pro(4-cis-isoamyl)-Arg(Cbz)lactam.

By a method substantially equivalent to that described in Example 1-K, 4.8 g (49%) of Cbz-D-hPro-Pro(4-cis-isoamyl)-Arg(Cbz)lactam were prepared from Cbz-D-hPro-Pro(4-cis-isoamyl)-OH and Arg(Cbz)lactam.2 HCl.

$^1$H NMR

FD-MS m/e 703 (M$^+$)

Analysis for $C_{38}H_{50}N_6O_7$: Calc: C, 64.94; H, 7.17; N, 11.96; Found: C, 64.83; H, 7.41; N, 11.67.

F) Preparation of D-hPro-Pro(4-cis-isoamyl)-ArgH.2 HCl.

By a method substantially equivalent to that described in Example 1-L, 1.9 g (85%) of crude D-hPro-Pro(4-cis-isoamyl)-ArgH.2 HCl were prepared from Cbz-D-hPro-Pro(4-cis-isoamyl)Arg(Cbz)lactam. RPHPLC method A was used to purify 1.0 g of this material and 0.22 g (22%) of pure D-hPro-Pro(4-cis-isoamyl)-ArgH.2 HCl were isolated.

$^1$H NMR

FAB-MS m/e 437 (MH$^+$)

Analysis for $C_{22}H_{40}N_6O_3$.2 HCl.1.5 H$_2$O: Calc: C, 49.25; H, 8.45; N, 15.66; Found: C, 49.09; H, 8.17; N, 15.62.

EXAMPLE 5

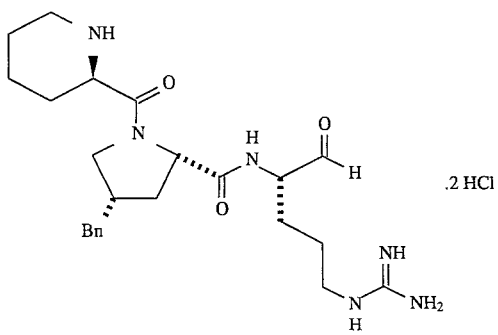

Synthesis of D-hPro-Pro(4-cis-benzyl)-ArgH.2 HCl

A) Preparation of Cbz-Pro(4-phenyl-methylidene)-OEt.

By a method substantially equivalent to that described in Example 1-C, 24.3 g (77%) of Cbz-Pro(4-phenyl-methylidene)-OEt were prepared from Cbz-Pro(4-oxo)-OEt and benzylidene triphenylphosphine.

$^1$H NMR

FD-MS m/e 365 (M$^+$)

Analysis for $C_{22}H_{23}NO_4$: Calc: C, 72.31; H, 6.34; N, 3.83; Found: C, 72.05; H, 6.33; N, 3.80.

B) Preparation of Pro(4-cis-benzyl)-OEt.

By a method substantially equivalent to that described in Example 4-B, 10.9 g (87%) of Pro(4-cis-benzyl)-OEt were prepared from Cbz-Pro(4-phenyl-methylidene)-OEt.

$^1$H NMR

FD-MS m/e 234 (M$^+$)

Analysis for $C_{14}H_{19}NO_2$: Calc: C, 72.07; H, 8.21; N, 6.00; Found: C, 72.02; H, 8.25; N, 6.14.

C) Preparation of Cbz-D-hPro-Pro(4-cis-benzyl)-OEt.

By a method substantially equivalent to that described in Example 1-F, 12.6 g (99%) of Cbz-D-hPro-Pro(4-cis-benzyl)-OEt were prepared from Cbz-D-hPro-OH and Pro(4-cis-benzyl)-OEt.

$^1$H NMR

FD-MS m/e 478 (M$^+$)

D) Preparation of Cbz-D-hPro-Pro(4-cis-benzyl)-OH.

By a method substantially equivalent to that described in Example 1-G, 8.2 g (87%) of Cbz-D-hPro-Pro(4-cis-benzyl)-OH were prepared.

$^1$H NMR

FD-MS m/e 451 (M$^+$)

Analysis for $C_{26}H_{30}N_2O_5$: Calc: C, 69.31; H, 6.71; N, 6.22; Found: C, 69.61; H, 6.85; N, 6.33.

E) Preparation of Cbz-D-hPro-Pro(4-cis-benzyl)-Arg(Cbz)lactam.

By a method substantially equivalent to that described in Example 1-K, 6.6 g (65%) of Cbz-D-hPro-Pro(4-cis-benzyl)-Arg(Cbz)lactam were prepared from Cbz-D-hPro-Pro(4-cis-benzyl)-OH and 2 HCl.Arg(Cbz)lactam.

$^1$H NMR

FD-MS m/e 723 (M$^+$)

Analysis for $C_{40}H_{46}N_6O_7$: Calc: C, 66.47, H, 6.41, N, 11.63; Found: C, 66.28, H, 6.54, N, 11.43.

F) Preparation of D-hPro-Pro(4-cis-benzyl)-ArgH.2 HCl.

By a method substantially equivalent to that described in Example 1-L, 2.9 g (80%) of crude D-hPro-Pro(4-cis-benzyl)-ArgH.2 HCl were prepared from Cbz-D-hPro-Pro(4-cis-benzyl)-Arg(Cbz)lactam. RPHPLC method A was used to purify 2.0 g of this material and 1.4 g (71%) of pure D-hPro-Pro(4-cis-isoamyl)-ArgH.2 HCl were isolated.

$^1$H NMR

FAB-MS m/e 457 (MH$^+$)

Analysis for $C_{24}H_{36}N_6O_3$.2 HCl.H$_2$O:

Calc: C, 52.65; H, 7.36; N, 15.35; Found: C, 52.99; H, 7.66; N, 15.53.

EXAMPLE 6

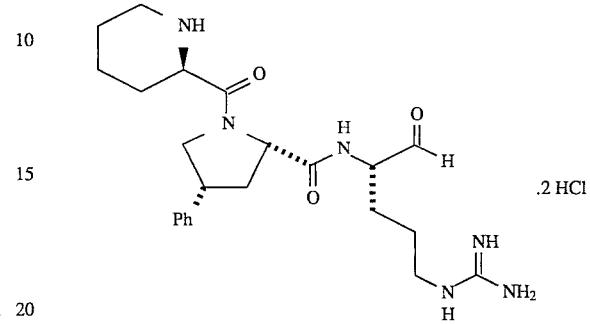

Synthesis of D-hPro-Pro(4-cis-phenyl)-ArgH.2 HCl

A) Preparation of Cbz-Pro(4-phenyl-3,4-dehydro)-OEt.

To a solution of Cbz-Pro(4-oxo)-OEt (24.6 g, 84.4 mmol) in tetrahydrofuran (150 mL) at −78° C. was added dropwise a solution of phenyl magnesium bromide (3N, 31 mL, 93 mmol). The solution was warmed to 0° C. and after an additional 3 hours, saturated aqueous NH$_4$Cl (300 mL) was added. The mixture was diluted with ethyl acetate (350 mL) and the layers were separated. The organic phase was washed twice with saturated aqueous NH$_4$Cl, twice with brine, and then dried (MgSO$_4$), filtered and concentrated in vacuo. The residue was dissolved in dichloromethane (100 mL) and trifluoroacetic acid (100 mL) was added with stirring. After 2 hours, the solvents were removed in vacuo and the resulting syrup was dissolved in ethyl acetate (500 mL) and washed twice with 1N citric acid, twice with saturated aqueous NaHCO$_3$, and twice with brine. The organic solution was then dried with MgSO$_4$, filtered and concentrated to give a yellow oil. This oil was purified by flash chromatography over silica gel, eluting with a step gradient of hexanes through 1:1 ethyl acetate/hexanes. The fractions containing pure product (as judged by TLC) were combined and concentrated in vacuo to give 16.2 g (55%) of Cbz-Pro(4-phenyl-3,4-dehydro)-OEt.

$^1$H NMR

FD-MS m/e 351 (M$^+$)

B) Preparation of Pro(4-cis-phenyl)-OEt.

By a method substantially equivalent to that described in Example 4-B, 6 g (60%) of Pro(4-cis-phenyl)-OEt were prepared from Cbz-Pro(4-phenyl-3,4-dehydro)-OEt.

$^1$H NMR

FD-MS m/e 219 (M$^+$)

Analysis for $C_{13}H_{17}NO_2$: Calc: C, 71.21; H, 7.81; N, 6.39; Found: C, 70.98; H, 7.71; N, 6.43.

C) Preparation of Cbz-D-hPro-Pro(4-cis-phenyl)-OEt.

By a method substantially equivalent to that described in Example 1-F, 10.3 g (88%) of Cbz-D-hPro-Pro(4-cis-phenyl)-OEt were prepared from Cbz-D-hPro-OH and Pro(4-cis-phenyl)-OEt.

$^1$H NMR

FD-MS m/e 464 (M$^+$)

Analysis for $C_{27}H_{32}N_2O_5$: Calc: C, 69.81; H, 6.94; N, 6.03; Found: C, 69.51; H, 7.12; N, 5.88.

D) Preparation of Cbz-D-hPro-Pro(4-cis-phenyl)-OH.

By a method substantially equivalent to that described in Example 1-G, 8.1 g (86%) of Cbz-D-hPro-Pro(4-cis-phenyl)-OH were prepared.

¹H NMR

FD-MS m/e 437 (MH⁺)

Analysis for $C_{25}H_{28}N_2O_5$: Calc: C, 68.79; H, 6.47; N, 6.42; Found: C, 68.58; H, 6.45; N, 6.43.

E) Preparation of Cbz-D-hPro-Pro(4-cis-phenyl)-Arg(Cbz)lactam.

By a method substantially equivalent to that described in Example 1-K, 6.7 g (61%) of Cbz-D-hPro-Pro(4-cis-phenyl)-Arg(Cbz)lactam were prepared from Cbz-D-hPro-Pro(4-cis-phenyl)-OH and Arg(Cbz)lactam.2 HCl.

¹H NMR

FD-MS m/e 709 (M⁺)

Analysis for $C_{39}H_{44}N_6O_7$: Calc: C, 66.09; H, 6.26; N, 11.86; Found: C, 66.35; H, 6.39; N, 11.82.

F) Preparation of D-hPro-Pro(4-cis-phenyl)-ArgH.2 HCl.

To a stirring solution of D-hPro-Pro(4-cis-phenyl)-Arg(Cbz)lactam (4 g, 5.6 mmol) in anhydrous tetrahydrofuran (200 mL) at −78° C. was added via syringe a solution of lithium aluminum hydride 1N in tetrahydrofuran (5.6 mL, 5.6 mmol) over 5 minutes. After 30 minutes, the reaction mixture was poured into a solution of cold, 1N $H_2SO_4$ (100 mL). The solution was then diluted with water (100 mL) and washed with hexanes (100 mL). The aqueous phase was then washed three times with 1:1 tetrahydrofuran/hexanes (200 mL), saturated with solid NaCl, and extracted four times with ethyl acetate (150 mL). The combined ethyl acetate extracts were washed with saturated aqueous NaCl (50 mL), dried ($MgSO_4$), and concentrated in vacuo to give a white foam.

The foam was then dissolved in ethanol (200 mL) and water (100 mL) and 1N HCl (20 mL) was added. To this stirring solution was then added 5% Pd-on-carbon (2.5 g). Hydrogen gas was then bubbled through the solution for 4 hours, and then the reaction was flushed with nitrogen and filtered over a pad of diatomaceous earth. The ethanol was removed in vacuo at 30° C. and then the residue was redissolved in water (50 mL). The pH of the aqueous solution was adjusted to 4 with Bio Rad ion exchange resin (basic form), filtered and lyophilized to give 2.5 g (87%) of a white powder. Purification of this compound by RPHPLC was unnecessary.

¹H NMR

FAB MS m/e 443 (MH⁺)

Analysis for $C_{23}H_{34}N_6O_3\cdot 3\ HCl\cdot H_2O$: Calc: C, 48.47; H, 6.89; N, 14.74; Found: C, 48.52; H, 6.84; N, 14.67.

EXAMPLE 7

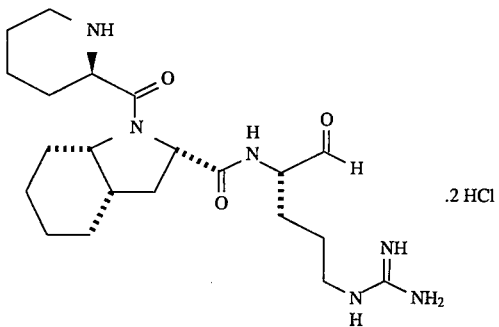

Synthesis of D-hPro-cis-Ohi-ArgH.2 HCl
(N-[(1-D-homoprolyl-cis-octahydro-1H-indol-2(S)-yl)carbonyl]-L-argininal dihydrochloride)

A) Preparation of (S)-cis-octahydroindole-2-carboxylic acid ethyl ester.HCl.

HCl gas was bubbled through a stirring suspension of (S)-indoline-2-carboxylic acid (20 g, 110 mmol) in ethanol (400 mL). When the acid was completely dissolved, the solution was brought to reflux. After 16 hours, the solution was cooled and the solvent removed in vacuo. The residue was triturated with diethyl ether and the resulting off-white solid was collected by filtration, washed with hexanes and dried overnight in a vacuum oven at 30° C. (25.5 g, 100%). This solid, (S)-indoline-2-carboxylic acid ethyl ester hydrochloride, was dissolved in ethanol (455 mL). To this was added 5% Pd/C (25.5 g) and the resulting suspension was hydrogenated on a Parr shaker for 8 hours (4.1 bar, 60 psi). The solution was filtered to remove catalyst and the filtrate was concentrated in vacuo. The residue was triturated with diethyl ether and the resulting solid was isolated by filtration to give 18.8 g (73%) of a white powder.

¹H NMR

FD-MS m/e 197 (M⁺)

Analysis for $C_{11}H_{19}NO_2\cdot HCl$: Calc: C, 56.53; H, 8.63; N, 5.99; Found: C, 56.24; H, 8.44; N, 6.00.

B) Preparation of Cbz-D-hPro-cis-Ohi-OEt.

By a method substantially equivalent to that described in Example 1-F, 13.5 g (93%) of Cbz-D-hPro-cis-Ohi-OEt were prepared from Cbz-D-hPro-OH and cis-Ohi-OEt.HCl.

¹H NMR

FD-MS m/e 442 (M⁺)

Analysis for $C_{25}H_{34}N_2O_5$: Calc: C, 67.85; H, 7.74; N, 6.33; Found: C, 67.59; H, 7.72; N, 6.48.

C) Preparation of Cbz-D-hPro-cis-Ohi-OH.

By a method substantially equivalent to that described in Example 1-G, 12.5 g (102%) of Cbz-D-hPro-cis-Ohi-OH were prepared.

¹H NMR

FD-MS m/e 414 (M⁺)

Analysis for $C_{23}H_{30}N_2O_5$: Calc: C, 66.65; H, 7.29; N, 6.76; Found: C, 66.46; H, 7.30; N, 6.86.

D) Preparation of Cbz-D-hPro-cis-Ohi-Arg(Cbz)lactam.

By a method substantially equivalent to that described in Example 1-K, 5.9 g (50%) of Cbz-D-hPro-cis-Ohi-Arg(Cbz)lactam were prepared from Cbz-D-hPro-cis-Ohi-OH and Arg(Cbz)lactam.2 HCl.

¹H NMR

FD-MS m/e 687 (M⁺)

Analysis for $C_{37}H_{46}N_6O_7$: Calc: C, 64.71; H, 6.75; N, 12.24; Found: C, 64.72; H, 6.60; N, 12.01.

E) Preparation of D-hPro-cis-Ohi-ArgH.2 HCl.

By a method substantially equivalent to that described in Example 1-L, 2.0 g (62%) of D-hPro-cis-Ohi-ArgH.2 HCl were prepared from Cbz-D-hPro-cis-Ohi-Arg(Cbz)lactam.

¹H NMR

FAB-MS m/e 421 (MH⁺)

Analysis for $C_{21}H_{36}N_6O_3\cdot 2\ HCl\cdot 1.5\ H_2O$: Calc: C, 48.46; H, 7.94; N, 16.15; Found: C, 48.72; H, 7.82; N, 15.98.

EXAMPLE 8

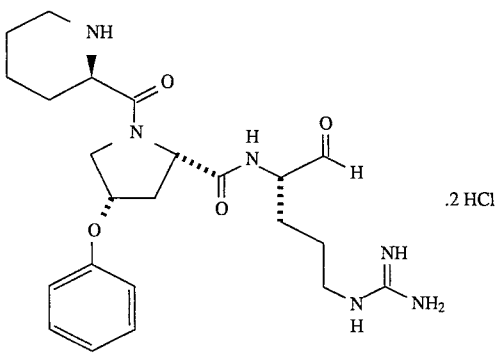

Synthesis of D-hPro-Pro(4-cis-phenoxy)-ArgH.2 HCl
(D-homoprolyl-L-cis-4-phenoxy-L-prolyl-D-argininal
dihydrochloride)

A) Preparation of Cbz-Pro(4-cis-phenoxy)-OEt.

To a solution of Cbz-Pro(4-trans-OH)-OEt (58.8 g, 200 mmol), triphenylphosphine (65.6 g, 250 mmol), and phenol (23.5 g, 250 mmol) in tetrahydrofuran (500 mL) at 0° C., was added (dropwise over 1 hour) a solution of diethylazodicarboxylate (40 mL, 250 mmol) in tetrahydrofuran (50 mL). The cold bath was then removed and the solution was allowed to warm to room temperature (16 hours). The solvent was then removed in vacuo and the remaining amber syrup was triturated with diethyl ether. The white solid was removed by filtration and the filtrate was concentrated. The residue was then chromatographed over silica gel (1 Kg), eluting with a step gradient from hexanes through 1:1 ethyl acetate/hexanes. The fractions containing pure product (as judged by TLC) were combined and concentrated in vacuo to give 36.3 g (50%) of a colorless syrup.

$^1$H NMR

FD-MS m/e 369 (M$^+$)

Analysis for $C_{21}H_{23}NO_5$: Calc: C, 68.28; H, 6.28; N, 3.79; Found: C, 68.38; H, 6.30; N, 3.89.

B) Preparation of Pro(4-cis-phenoxy)-OEt.HCl.

By a method substantially equivalent to that described in Example 1-D, 14.2 g (77%) of Pro(4-cis-phenoxy)-OEt.HCl were prepared from Cbz-Pro(4-phenoxy)-OEt.

$^1$H NMR

FD-MS m/e 235 (M$^+$)

Analysis for $C_{13}H_{18}NO_3Cl$: Calc: C, 57.46; H, 6.68; N, 5.15; Found: C, 57.68; H, 6.78; N, 5.18.

C) Preparation of Cbz-D-hPro-Pro(4-cis-phenoxy)-OEt.

By a method substantially equivalent to that described in Example 1-F, 19.4 g (100%) of Cbz-D-hPro-Pro(4-cis-phenoxy)-OEt were prepared from Cbz-D-hPro-OH and Pro(4-cis-phenoxy)-OEt.HCl.

$^1$H NMR

FD-MS m/e 480 (M$^+$)

Analysis for $C_{27}H_{32}NO_6$: Calc: C, 67.48; H, 6.71; N, 5.83; Found: C, 67.71; H, 6.79; N, 5.89.

D) Preparation of Cbz-D-hPro-Pro(4-cis-phenoxy)-OH.

By a method substantially equivalent to that described in Example 1-G, 16 g (100%) of Cbz-D-hPro-Pro(4-cis-phenoxy)-OH were prepared.

$^1$H NMR

FD-MS m/e 452 (M$^+$)

Analysis for $C_{25}H_{28}N_2O_6$: Calc: C, 66.36; H, 6.24; N, 6.19; Found: C, 66.22; H, 6.18; N, 6.17.

E) Preparation of Cbz-D-hPro-Pro(4-cis-phenoxy)-Arg(Cbz)lactam.

By a method substantially equivalent to that described in Example 1-K, 6.7 g (62%) of Cbz-D-hPro-Pro(4-cis-phenoxy)-Arg(Cbz)lactam were prepared from Cbz-D-hPro-Pro(4-cis-phenoxy)-OH and Arg(Cbz)lactam.2 HCl.

$^1$H NMR

FD-MS m/e 726 (MH$^+$)

Analysis for $C_{39}H_{44}N_6O_8$: Calc: C, 64.63; H, 6.12; N, 11.59; Found: C, 64.52; H, 5.96; N, 11.48.

F) Preparation of D-hPro-Pro(4-cis-phenoxy)-ArgH.2 HCl.

By a method substantially equivalent to that described in Example 6-F, 2.5 g (77%) of crude D-hPro-Pro(4-cis-phenoxy)-ArgH.2 HCl were prepared from Cbz-D-hPro-Pro(4-cis-phenoxy)-Arg(Cbz)lactam. RPHPLC method A was used to purify 1.0 g of this material and 0.77 g (77%) of pure D-hPro-Pro(4-cis-phenoxy)-ArgH.2 HCl were isolated.

$^1$H NMR

FAB-MS m/e 459 (MH$^+$)

Analysis for $C_{23}H_{34}N_6O.2$ HCl: Calc: C, 51.98; H, 6.83; N, 15.81; Found: C, 51.77; H, 6.53; N, 15.81.

EXAMPLE 9

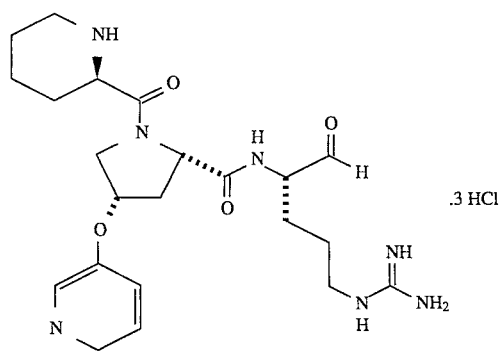

Synthesis of D-hPro-Pro(4-cis-(3-pyridyloxy))-ArgH.3 HCl

A) Preparation of Pro(4-trans-OH)-OEt.HCl.

Pro(4-trans-OH)-OH (100 g, 763 mmol) was suspended with stirring in absolute EtOH (1 L) and HCl gas was bubbled through the suspension until all solid had dissolved (15 minutes). The solution was then brought to reflux. After 24 hours, the solution was cooled to room temperature and the solvent was removed in vacuo. The resulting white solid was washed with diethyl ether and dried to give 117 g (79%) of white needles.

$^1$H NMR

FD-MS m/e 160 (MH$^+$)

Analysis for $C_7H_{13}NO_3$.HCl: Calc: C, 42.97; H, 7.21; N, 7.16; Found: C, 42.75; H, 7.04; N, 7.28.

B) Preparation of Cbz-D-hPro-Pro(4-trans-OH)-OEt.

By a method substantially equivalent to that described in Example 1-F, 37 g (91%) of Cbz-D-hPro-Pro(4-trans-OH)-OEt were prepared from Cbz-D-hPro-OH and Pro(4-trans-OH)-OEt.HCl.

$^1$H NMR

FD-MS m/e 404 (M$^+$)

Analysis for $C_{21}H_{28}N_2O_6$: Calc: C, 62.36; H, 6.98; N, 6.93; Found: C, 62.60; H, 6.86; N, 7.10.

C) Preparation of Cbz-D-hPro-Pro(4-cis-(3-pyridyloxy))-OEt.

By a method substantially equivalent to that described in Example 8-A, 10 g (50%) of Cbz-D-hPro-Pro(4-trans-(3-pyridyloxy))-OEt were prepared from Cbz-D-hPro-Pro(4-trans-OH)-OEt.

¹H NMR
FD-MS m/e 481 (M⁺)

D) Preparation of Cbz-D-hPro-Pro(4-cis-(3-pyridyloxy))-OH.

By a method substantially equivalent to that described in Example 1-G, 8.3 g (92%) of Cbz-D-hPro-Pro(4-cis-(3-pyridyloxy))-OH were prepared.

¹H NMR
FD-MS m/e 454 (MH⁺)
Analysis for $C_{24}H_{27}N_3O_6$: Calc: C, 63.56; H, 6.00; N, 9.27; Found: C, 63.65; H, 6.05; N, 9.25.

E) Preparation of Cbz-D-hPro-Pro(4-cis-(3-pyridyloxy))-Arg(Cbz)lactam.

By a method substantially equivalent to that described in Example 1-K, 4.8 g (83%) of Cbz-D-hPro-Pro(4-cis-(3-pyridyloxy))-Arg(Cbz)lactam were prepared from Cbz-D-hPro-Pro(4-cis-(3-pyridyloxy))-OH and Arg(Cbz)lactam.2 HCl.

¹H NMR
FD-MS m/e 726 (M⁺)

F) Preparation of D-hPro-Pro(4-cis-(3-pyridyloxy))-ArgH.3 HCl.

By a method substantially equivalent to that described in Example 6-F, 2.4 g (82%) of crude D-hPro-Pro(4-cis-(3-pyridyloxy))-ArgH.3 HCl were prepared from Cbz-D-hPro-Pro(4-cis-(3-pyridyloxy))-Arg(Cbz)lactam. RPHPLC method B was used to purify 1.2 g of this material and 1.1 g (92%) of pure D-hPro-Pro-(4-cis-(3-pyridyloxy))-ArgH.3 HCl were isolated.

¹H NMR
FAB-MS m/e 460 (MH⁺)
Analysis for $C_{22}H_{33}N_7O_4$.3 HCl.H₂O: Calc: C, 43.07; H, 6.66; N, 16.21; Found: C, 43.02; H, 6.63; N, 16.51.

EXAMPLE 10

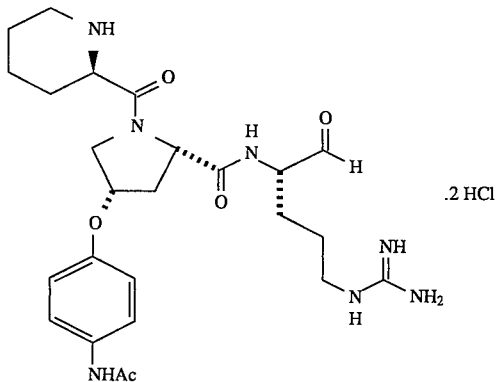

Synthesis of
D-hPro-Pro(4-cis-(4-AcNH-phenoxy))-ArgH.2 HCl

A) Preparation of Cbz-D-hPro-Pro(4-cis-(4-NO₂phenoxy))-OEt.

By a method substantially equivalent to that described in Example 8-A, 15.9 g (63%) of Cbz-D-hPro-Pro(4-cis-(4-NO₂-phenoxy))-OEt were prepared from Cbz-D-hPro-Pro(4-trans-OH)-OEt.

¹H NMR
FD-MS m/e 525 (M⁺)

B) Preparation of Cbz-D-hPro-Pro(4 -cis-(4-NH₂-phenoxy))-OEt.

To a solution of Cbz-D-hPro-Pro(4-cis-(4-NO₂-phenoxy))-OEt (15.7 g, 30 mmol) in ethanol (200 mL) was added water (100 mL), followed by Na₂S₂O₄ (10.5 g, 60 mmol), and the mixture was heated to reflux (30 minutes). The solution was then allowed to cool and the solvents were removed in vacuo. The residue was partitioned between ethyl acetate and saturated aqueous NaHCO₃. The layers were separated and the organic layer was washed once with saturated aqueous NaHCO₃, dried with MgSO₄, filtered and concentrated. The resulting yellow foam was chromatographed over silica gel (500 g) with a step gradient of chloroform through 9:1 chloroform/methanol. The product containing fractions as judged by TLC were combined and concentrated in vacuo to give 7.8 g (52%) of a tan foam.

¹H NMR
FD-MS m/e 496 (M⁺)

C) Preparation of Cbz-D-hPro-Pro(4-cis-(4-AcNH-phenoxy))-OEt.

To a stirring solution of Cbz-D-hPro-Pro(4-cis-(4-NH₂-phenoxy))-OEt (3.5 g, 7.1 mmol) and N,N-diisopropyl ethylamine (2.5 mL, 14.1 mmol) in dichloromethane (50 mL) was added acetic anhydride (0.73 mL, 7.8 mmol). After 16 hours, the solvent was removed in vacuo and the residue was dissolved in ethyl acetate (100 mL). The organic phase was then washed twice with 1N citric acid (50 mL), twice with saturated aqueous NaHCO₃, and twice with brine. The combined ethyl acetate extracts were dried with MgSO₄, filtered, and concentrated in vacuo to give 2.6 g (70%) of a light pink foam.

¹H NMR
FD-MS m/e 537 (M⁺)
Analysis for $C_{29}H_{35}N_3O_7$: Calc: C, 64.79; H, 6.56; N, 7.82; Found: C, 65.00; H, 6.54; N, 7.58.

D) Preparation of Cbz-D-hPro-Pro(4-cis-(4-AcNH-phenoxy))-OH.

By a method substantially equivalent to that described in Example 1-G, 2.2 g (93%) of Cbz-D-hPro-Pro(4-cis-(4-AcNH-phenoxy))-OH were prepared.

¹H NMR
FD-MS m/e 509 (M⁺)
Analysis for $C_{27}H_{31}N_3O_7$: Calc: C, 63.64; H, 6.13; N, 8.25; Found: C, 63.15; H, 6.16; N, 7.64.

E) Preparation of Cbz-D-hPro-Pro(4-cis-(4-AcNH-phenoxy))-Arg(Cbz)lactam.

By a method substantially equivalent to that described in Example 1-K, 2.2 g (70%) of Cbz-D-hPro-Pro(4-cis-(4-AcNH-phenoxy))-Arg(Cbz)lactam were prepared from Cbz-D-hPro-Pro(4-cis-(4-AcNH-phenoxy))-OH and Arg(Cbz)lactam.2 HCl.

¹H NMR
FD-MS m/e 781 (M⁺)
Analysis for $C_{41}H_{47}N_7O_9$: Calc: C, 62.98; H, 6.06; N, 12.54; Found: C, 61.76; H, 5.94; N, 11.35.

F) Preparation of D-hPro-Pro(4-cis-(4-AcNH-phenoxy))-ArgH.2 HCl.

By a method substantially equivalent to that described in Example 6-F, 0.66 g (47%) of crude D-hPro-Pro(4-cis-(4-AcNH-phenoxy))-ArgH.2 HCl were prepared from Cbz-D-hPro-Pro(4-cis-(4-AcNH-phenoxy))-Arg(Cbz)lactam. RPHPLC method B was used to purify 0.5 g of this material and 0.1 g (20%) of pure D-hPro-Pro-(4-cis-(4-AcNH-phenoxy))-ArgH.2 HCl were isolated.

¹H NMR
FAB-MS m/e 516 (MH⁺)
Analysis for $C_{25}H_{37}N_6O_5$.2.5 HCl: Calc: C, 49.49; H, 6.56; N, 16.16; Found: C, 49.82; H, 6.34; N, 16.13.

EXAMPLE 11

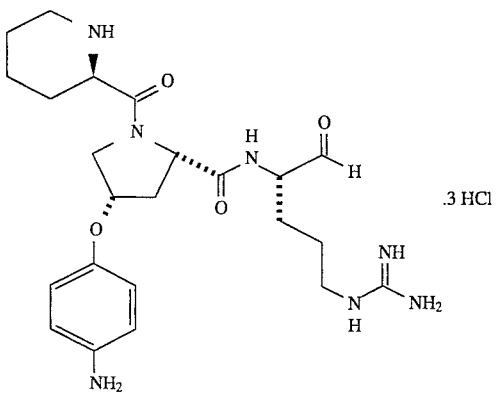

Synthesis of
D-hPro-Pro(4-cis-(4-NH$_2$-phenoxy))-ArgH.3 HCl

A) Preparation of Cbz-D-hPro-Pro(4-cis-(4-CbzNH-phenoxy))-OEt.

To a stirring solution of Cbz-D-hPro-Pro(4-cis-(4-NH$_2$-phenoxy))-OEt (3.5 g, 7.1 mmol) in dichloromethane (50 mL) was added N,N-diisopropylethylamine (2.5 mL, 14.1 mmol) followed by benzyl chloroformate (1.17 mL, 7.8 mmol). After stirring for 16 hours, the solvent was removed in vacuo and the residue was dissolved in ethyl acetate (100 mL), washed twice with 1N citric acid (50 mL), twice with saturated aqueous NaHCO$_3$, and twice with brine. The organic phase was then dried with MgSO$_4$, filtered, and concentrated in vacuo to give a brown syrup which was chromatographed over silica gel, eluting with a step gradient of hexanes through 60% ethyl acetate/hexanes. The fractions containing product as judged by TLC were combined and concentrated in vacuo to give 3 g (67%) of a colorless foam.

$^1$H NMR

FD-MS m/e 629 (M$^+$)

Analysis for C$_{35}$H$_{39}$N$_3$O$_8$: Calc: C, 66.76; H, 6.24; N, 6.67; Found: C, 66.79; H, 6.29; N, 6.66.

B) Preparation of Cbz-D-hPro-Pro(4-cis-(4-CbzNH-phenoxy))-OH.

By a method substantially equivalent to that described in Example 1-G, 2.4 g (88%) of Cbz-D-hPro-Pro(4-cis-(4-CbzNH-phenoxy))-OH were prepared.

$^1$H NMR

FD-MS m/e 601 (M$^+$)

Analysis for C$_{33}$H$_{35}$N$_3$O$_8$: Calc: C, 65.88; H, 5.86; N, 6.98; Found: C, 65.45; H, 6.30; N, 6.36.

C) Preparation of Cbz-D-hPro-Pro(4-cis-(4-CbzNH-phenoxy))-Arg(Cbz)lactam.

By a method substantially equivalent to that described in Example 1-K, 2.3 g (79%) of Cbz-D-hPro-Pro(4-cis-(4-CbzNH-phenoxy))-Arg(Cbz)lactam were prepared from Cbz-D-hPro-Pro(4-cis-(4-CbzNH-phenoxy))-OH and Arg(Cbz)lactam.2 HCl.

$^1$H NMR

FD-MS m/e 875 (MH$^+$)

Analysis for C$_{47}$H$_{51}$N$_7$O$_{10}$: Calc: C, 64.59; H, 5.88; N, 11.22; Found: C, 62.43; H, 5.69; N, 10.86.

D) Preparation of D-hPro-Pro(4-cis-(4-NH$_2$-phenoxy))-ArgH.3 HCl.

By a method substantially equivalent to that described in Example 6-F, 1.06 g (85%) of crude D-hPro-Pro(4-cis-(4-NH$_2$-phenoxy))-ArgH.3 HCl were prepared from Cbz-D-hPro-Pro(4-cis-(4-CbzNH-phenoxy))-Arg(Cbz)lactam.

RPHPLC method B was used to purify 0.8 g of this material and 0.6 g (75%) of pure D-hPro-Pro(4-cis-(4-NH$_2$-phenoxy))-ArgH.3 HCl were isolated.

$^1$H NMR

FAB-MS m/e 474 (MH$^+$)

Analysis for C$_{23}$H$_{35}$N$_7$O$_4$.3 HCl.2 H$_2$O: Calc: C, 44.63; H, 6.84; N, 15.83; Found: C, 44.82; H, 6.85; N, 15.91.

EXAMPLE 12

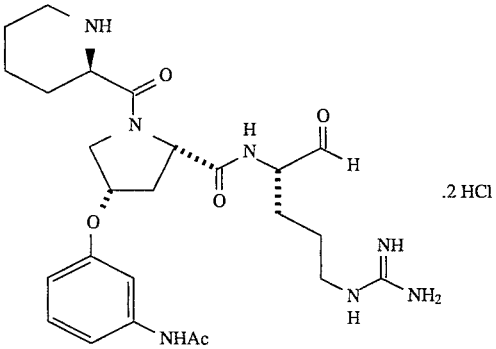

Synthesis of
D-hPro-Pro(4-cis-(3-AcNH-phenoxy))-ArgH.2 HCl

A) Preparation of Cbz-D-hPro-Pro(4-cis-(3-NO$_2$-phenoxy))-OEt.

By a method substantially equivalent to that described in Example 8-A, 63 g (97%) of Cbz-D-hPro-Pro(4-cis-(3-NO$_2$-phenoxy))-OEt were prepared from Cbz-D-hPro-Pro(4-trans-OH)-OEt.

$^1$H NMR

FD-MS m/e 525 (M$^+$)

B) Preparation of Cbz-D-hPro-Pro(4-trans-(3-NH$_2$-phenoxy))-OEt.

By a method substantially equivalent to that described in Example 10-B, 31.4 g (56%) of Cbz-D-hPro-Pro(4-cis-(3-NH$_2$-phenoxy))-OEt were prepared from Cbz-D-hPro-Pro(4-cis-(3-NO$_2$-phenoxy))-OEt.

$^1$H NMR

FD-MS m/e 495 (M$^+$)

C) Preparation of Cbz-D-hPro-Pro(4-cis-(3-AcNH-phenoxy))-OEt.

By a method substantially equivalent to that described in Example 10-C, 7 g (65%) of Cbz-D-hPro-Pro(4-cis-(3-AcNH-phenoxy))-OEt were prepared from Cbz-D-hPro-Pro(4-cis-(3-NH$_2$-phenoxy))-OEt.

$^1$H NMR

FD-MS m/e 538 (MH$^+$)

Analysis for C$_{29}$H$_{35}$N$_3$O$_7$: Calc: C, 64.79; H, 6.56; N, 7.82; Found: C, 65.05; H, 6.57; N, 8.08.

D) Preparation of Cbz-D-hPro-Pro(4-cis-(3-AcNH-phenoxy))-OH.

By a method substantially equivalent to that described in Example 1-G, 5.9 g (97%) of Cbz-D-hPro-Pro(4-cis-(3-AcNH-phenoxy))-OH were prepared.

$^1$H NMR

FD-MS m/e 511 (MH$^+$)

E) Preparation of Cbz-D-hPro-Pro(4-cis-(3-AcNH-phenoxy))-Arg(Cbz)lactam.

By a method substantially equivalent to that described in Example 1-K, 2.8 g (44%) of Cbz-D-hPro-Pro(4-cis-(3-AcNH-phenoxy))-Arg(Cbz)lactam were prepared from Cbz- D-hPro-Pro(4-cis-(3-AcNH-phenoxy))-OH and Arg(Cbz)lactam.2 HCl.

¹H NMR

FD-MS m/e 782 (M⁺)

Analysis for $C_{41}H_{47}N_7O_9$: Calc: C, 62.98; H, 6.06; N, 12.54; Found: C, 62.84; H, 6.19; N, 12.82.

F) Preparation of D-hPro-Pro(4-cis-(3-AcNH-phenoxy))-ArgH.2 HCl.

By a method substantially equivalent to that described in Example 6-F, 0.62 g (33%) of crude D-hPro-Pro(4-cis-(3-AcNH-phenoxy))-ArgH.2 HCl were prepared from Cbz-D-hPro-Pro(4-cis-(3-AcNH-phenoxy))-Arg(Cbz)lactam. RPHPLC method B was used to purify 0.5 g of this material and 0.15 g (30%) of pure D-hPro-Pro(4-cis-(3-AcNH-phenoxy))-ArgH.2 HCl were isolated.

¹H NMR

FAB-MS, m/e 516 (MH⁺)

Analysis for $C_{25}H_{37}N_7O_5$.2 HCl.1.5 $H_2O$: Calc: C, 48.78; H, 6.88; N, 15.93; Found: C, 48.75; H, 6.76; N, 15.58.

EXAMPLE 13

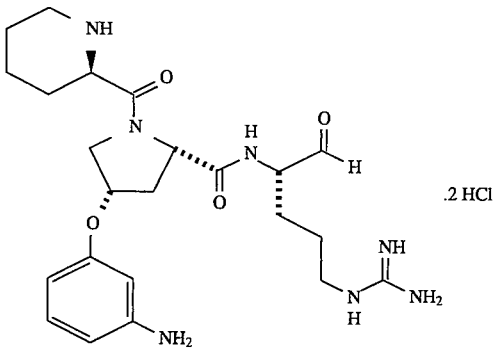

Synthesis of D-hPro-Pro(4-cis-(3-$NH_2$-phenoxy))-ArgH.2 HCl

A) Preparation of Cbz-D-hPro-Pro(4-cis-(3-CbzNH-phenoxy))-OEt.

By a method substantially equivalent to that described in Example 11-A, 9.7 g (76%) of Cbz-D-hPro-Pro(4-cis-(3-CbzNH-phenoxy))-OEt were prepared from Cbz-D-hPro-pro(4-cis-(3-$NH_2$-phenoxy))-OEt.

B) Preparation of Cbz-D-hPro-Pro(4-cis-(3-CbzNH-phenoxy))-OH.

By a method substantially equivalent to that described in Example 1-G, 7.2 g (84%) of Cbz-D-hPro-Pro(4-cis-(3-CbzNH-phenoxy))-OH were prepared.

¹H NMR

FD-MS m/e 602 (MH⁺)

Analysis for $C_{33}H_{35}N_3O_8$: Calc: C, 65.88; H, 5.86; N, 6.98; Found: C, 65.58; H, 5.84; N, 6.99.

C) Preparation of Cbz-D-hPro-Pro(4-cis-(3-CbzNH-phenoxy))-Arg(Cbz)lactam.

By a method substantially equivalent to that described in Example 1-K, 4.8 g (68%) of Cbz-D-hPro-Pro(4-cis-(3-CbzNH-phenoxy))-Arg(Cbz)lactam were prepared from Cbz-D-hPro-Pro(4-cis-(3-CbzNH-phenoxy))-OH and Arg(Cbz)lactam.2 HCl.

¹H NMR

FD-MS m/e 874 (M⁺)

Analysis for $C_{47}H_{51}N_7O_{10}$: Calc: C, 64.59; H, 5.88; N, 11.22; Found: C, 64.77; H, 5.90; N, 11.16.

D) Preparation of D-hPro-Pro(4-cis-(3-$NH_2$-phenoxy))-ArgH.2 HCl.

By a method substantially equivalent to that described in Example 6-F, 1.7 g (89%) of crude D-hPro-Pro(4-cis-(3-$NH_2$-phenoxy))-ArgH.2 HCl were prepared from Cbz-D-hPro-Pro(4-cis-(3-CbzNH-phenoxy))-Arg(Cbz)lactam. RPHPLC method B was used to purify 1.1 g of this material and 0.49 g (45%) of pure D-hPro-Pro(4-cis-(3-$NH_2$-phenoxy))-ArgH.2 HCl were isolated.

¹H NMR

FAB-MS m/e 474 (MH⁺)

Analysis for $C_{23}H_{35}N_7O_4$.2.5 HCl.0.5 $H_2O$: Calc: C, 48.15; H, 6.76; N, 17.09; Found: C, 48.30; H, 6.38; N, 17.08.

EXAMPLE 14

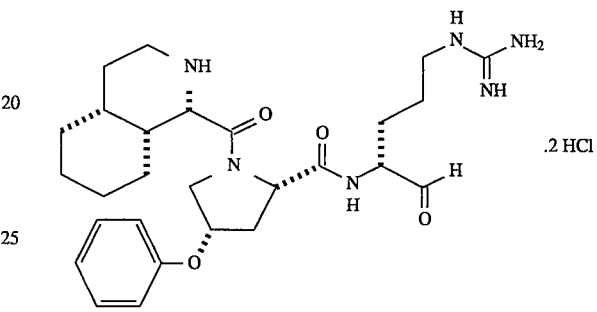

Synthesis of L-1-Piq-Pro(4-cis-phenoxy)-ArgH.2 HCl

A) Preparation of D,L-1-cis-Piq-OH.

A solution of 1-isoquinolinecarboxylic acid (50 g, 0.288 mol) in EtOH (150 mL) and 60 mL of 5N HCl was reacted with 5% Rh/$Al_2O_3$ (14 g) at 750 psi (52 bar) of hydrogen in a high pressure apparatus at 50° C. for 17 hours. The reaction mixture was filtered through a diatomaceous earth pad, and the filtrate was concentrated in vacuo. The solid was triturated with water, filtered and dried to give DL-perhydro-1-isoquinolinecarboxylic acid (DL-1-Piq-OH) (30 g, 48%) FD-MS 184 (MH⁺).

B) Preparation of Cbz-D,L-1-cis-Piq-OH.

DL-1-Piq-OH (30.2 g, 137 mmol) was dissolved in tetrahydrofuran (150 mL) and water (150 mL). The pH of the solution was adjusted to 9.8 with 5N NaOH and benzyl chloroformate (21.6 mL, 151 mmol) was added dropwise and the pH maintained at 9.5 with 2N NaOH. The reaction was stirred for an additional 2 hours at room temperature. The organic solvent was evaporated in vacuo, and diethyl ether (150 mL) and water (50 mL) were added to the residue. The aqueous layer was separated, the pH of the solution was adjusted to 2.5 with 5N HCl, and ethyl acetate (200 mL) was added. The organic layer was separated and dried ($MgSO_4$) and the filtrate was concentrated in vacuo to give a clear oil. The oil was dissolved in diethyl ether (150 mL) and the solution allowed to stand at room temperature (24 hours). The precipitate was filtered and dried to give Cbz-DL-perhydro-1-isoquinolinecarboxylic acid (Cbz-DL-1-Piq-OH) (32 g, 75%) FD-MS 318 (MH⁺).

C) Preparation of Cbz-L-1-cis-Piq-Pro(4-cis-hydroxy)-OMe.

By a method substantially equivalent to that described in Example 1-F, Cbz-D,L-1-cis-Piq-Pro(4-cis-hydroxy)-OMe were prepared from Cbz-D,L-1-cis-Piq-OH and Pro(4-trans-hydroxy)-OMe.HCl. Diasteromeric separation was achieved by silica gel chromatography using a gradient of chloroform to 10% methanol/chloroform. Fractions containing the leading diastereomer ($R_f$=0.35; 10% methanol/chloroform) were combined and concentrated in vacuo to give 4.7 g (39%) of a white foam.

$^1$H NMR

FD-MS m/e 444 (M$^+$)

Analysis for $C_{24}H_{32}N_2O_6$: Calc: C, 64.85; H, 7.26; N, 6.30; Found: C, 64.69; H, 7.13; N, 6.32.

D) Preparation of Cbz-L-1-cis-Piq-Pro(4-cis-phenoxy)-OMe.

By a method substantially equivalent to that described in Example 8-A, 2.8 g (43%) of Cbz-L-1-cis-Piq-Pro(4-cis-phenoxy)-OMe were prepared from Cbz-L-1-cis-Piq-Pro(4-trans-hydroxy)-OMe.

$^1$H NMR

FD-MS m/e 520 (M$^+$)

E) Preparation of Cbz-L-1-cis-Piq-Pro(4-cis-phenoxy)-OH.

By a method substantially equivalent to that described in Example 1-G, 2.4 g (95%) of Cbz-L-1-cis-Piq-Pro(4-cis-phenoxy)-OH were prepared.

$^1$H NMR

FD-MS m/e 507 (M$^+$)

F) Preparation of Cbz-L-1-cis-Piq-Pro(4-cis-phenoxy)-Arg(Cbz)lactam.

By a method substantially equivalent to that described in Example 1-K, 1.9 g (58%) of Cbz-L-1-cis-Piq-Pro(4-cis-phenoxy)-Arg(Cbz)lactam were prepared from Cbz-L-1-cis-Piq-Pro(4-cis-phenoxy)-OH and Arg(Cbz)lactam.2 HCl.

$^1$H NMR

FD-MS m/e 779 (M$^+$)

G) Preparation of L-1-cis-Piq-Pro(4-cis-phenoxy)-ArgH.2 HCl.

By a method substantially equivalent to that described in Example 6-F, 1.24 g (78%) of L-1-cis-Piq-Pro(4-cis-phenoxy)ArgH.2 HCl were prepared from Cbz-L-1-cis-Piq-Pro(4-cis-phenoxy)-Arg(Cbz)lactam. Purification by HPLC was unnecessary.

$^1$H NMR

FAB-MS m/e 513 (MH$^+$)

Analysis for $C_{27}H_{40}N_6O_4$.3 HCl.H$_2$O: Calc: C, 50.67; H, 7.09; N, 13.13; Found: C, 50.35; H, 6.91; N, 12.85.

Analysis for $C_{24}H_{32}N_2O_6$: Calc: C, 64.85; H, 7.26; N, 6.30; Found: C, 65.11; H, 7.27; N, 6.25.

B) Preparation of Cbz-D-1-cis-Piq-Pro(4-cis-phenoxy)-OMe.

By a method substantially equivalent to that described in Example 8-A, 3.55 g (91%) of Cbz-D-1-cis-Piq-Pro(4-cis-phenoxy)-OMe were prepared from Cbz-D-1-cis-Piq-Pro(4-trans-hydroxy)-OMe.

$^1$H NMR

FD-MS m/e 520 (M$^+$)

C) Preparation of Cbz-D-1-cis-Piq-Pro(4-cis-phenoxy)-OH.

By a method substantially equivalent to that described in Example 1-G, 2.1 g (70%) of Cbz-D-1-cis-Piq-Pro(4-cis-phenoxy)-OH were prepared.

$^1$H NMR

FD-MS m/e 507 (M$^+$)

D) Preparation of Cbz-D-1-cis-Piq-Pro(4-cis-phenoxy)-Arg(Cbz)lactam.

By a method substantially equivalent to that described in Example 1-K, 3.8 g (72%) of Cbz-D-1-cis-Piq-Pro(4-cis-phenoxy)-Arg(Cbz)lactam were prepared from Cbz-D-1-cis-Piq-Pro(4-cis-phenoxy)-OH and Arg(Cbz)lactam.2 HCl.

$^1$H NMR

FD-MS m/e 779 (M$^+$)

E) Preparation of D-1-cis-Piq-Pro(4-cis-phenoxy)-ArgH.2 HCl.

By a method substantially equivalent to that described in Example 6-F, 1.1 g (86%) of crude Cbz-D-1-cis-Piq-Pro(4-cis-phenoxy)-ArgH.2 HCl were prepared from Cbz-D-1-cis-Piq-Pro(4-cis-phenoxy)-Arg(Cbz)lactam. One gram was purified using RPHPLC Method A to give 0.3 g (30%) of pure D-1-cis-Piq-Pro(4-cis-phenoxy)-ArgH.2 HCl.

$^1$H NMR

FAB-MS m/e 513 (MH$^+$)

Analysis for $C_{27}H_{40}N_6O_4$.2 HCl.0.5 H$_2$O: Calc: C, 54.54; H, 7.29; N, 14.13; Found: C, 54.94; H, 7.00; N, 14.12.

EXAMPLE 16

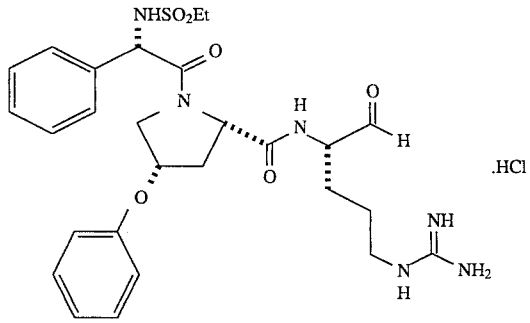

Synthesis of EtSO$_2$-L-Phg-Pro(4-cis-phenoxy)-ArgH.HCl

A) Preparation of Boc-D,L-Phg-Pro(4-cis-phenoxy)-OEt.

By a method substantially equivalent to that described in Example 1-F, 6.6 g (80%) of Boc-D,L-Phg-Pro(4-cis-phenoxy)-OEt were prepared from Boc-D-Phg-OH and Pro(4-cis-phenoxy)OEt.HCl. Significant racemization of the N-terminal residue occurred in this step as judged by TLC and $^1$H NMR.

$^1$H NMR

FD-MS m/e 468 (M$^+$)

Analysis for $C_{26}H_{32}N_2O_6$: Calc: C, 66.65; H, 6.88; N, 5.98; Found: C, 66.43; H, 6.67; N, 5.97.

EXAMPLE 15

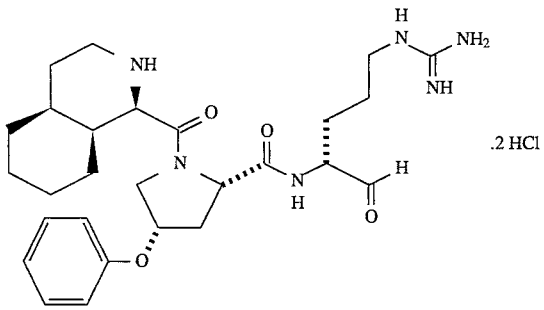

Synthesis of D-1-Piq-Pro(4-cis-phenoxy)-ArgH.2 HCl

A) Preparation of Cbz-D-1-cis-Piq-Pro(4-cis-hydroxy)-OMe.

Following the chromatography of Example 14-C, fractions containing the trailing diastereomer ($R_f$=0.25; 10% methanol/chloroform) were combined and concentrated in vacuo to give 2.4 g (20%) of a white foam.

$^1$H NMR

FD-MS m/e 444 (M$^+$)

39

B) Preparation of D,L-Phg-Pro(4-cis-phenoxy)-OEt.HCl.

By a method substantially equivalent to that described in Example 1-J, 4.2 g (97%) of D,L-Phg-Pro(4-cis-phenoxy)-OEt.HCl were prepared.

$^1$H NMR

FD-MS m/e 368 (MH$^+$)

Analysis for $C_{21}H_{24}N_2O_4$.HCl: Calc: C, 62.30; H, 6.22; N, 6.92; Found: C, 62.58; H, 6.24; N, 7.09.

C) Preparation of EtSO$_2$-D,L-Phg-Pro(4-cis-phenoxy)-OEt.

To a solution of D,L-Phg-Pro(4-cis-phenoxy)-OEt.HCl (4 g, 10 mmol) and diisopropylethylamine (3.9 mL, 23 mmol) in THF (60 mL) at −78° C., was added dropwise via an addition funnel a solution of ethanesulfonyl chloride (1.4 g, 11 mmol) in THF (10 mL). The cold bath was then left unattended and the solution warmed slowly to room temperature. After about 18 hours, the solution was concentrated in vacuo. The residue was dissolved in ethyl acetate (150 mL), washed twice with each 1N citric acid (100 mL), saturated aqueous NaHCO$_3$ (100 mL) and brine (100 mL). The organic phase was then dried with MgSO$_4$, filtered, and concentrated in vacuo to give 4.5 g (90%) of a yellow foam.

$^1$H NMR

FD-MS m/e 460 (M$^+$)

Analysis for $C_{23}H_{28}N_2O_6S$: Calc: C, 59.98; H, 6.13; N, 6.08; Found: C, 59.76; H, 6.18; N, 5.81.

D) Preparation of EtSO$_2$-D,L-Phg-Pro(4-cis-phenoxy)-OH.

By a method substantially equivalent to that described in Example 1-G, 3.4 g (94%) of EtSO$_2$-D,L-Phg-Pro(4-cis-phenoxy)-OH were prepared.

$^1$H NMR

FD-MS m/e 432 (M$^+$)

Analysis for $C_{21}H_{24}N_2O_6S$: Calc: C, 58.32; H, 5.59; N, 6.48; Found: C, 58.07; H, 5.62; N, 6.27.

E) Preparation of EtSO$_2$-D,L-Phg-Pro(4-cis-phenoxy)-Arg(Cbz)lactam.

By a method substantially equivalent to that described in Example 1-K, 3.8 g (72%) of EtSO$_2$-D,L-Phg-Pro(4-cis-phenoxy)-Arg(Cbz)lactam were prepared from EtSO$_2$-D,L-Phg-Pro(4-cis-phenoxy)-OH and Arg(Cbz)lactam.2 HCl.

$^1$H NMR

FD-MS m/e 706 (MH$^+$)

Analysis for $C_{35}H_{40}N_6O_8S$: Calc: C, 59.65; H, 5.72; N, 11.92; Found: C, 59.56; H, 5.78; N, 11.91.

F) Preparation of EtSO$_2$-L-Phg-Pro(4-cis-phenoxy)-ArgH.HCl.

By a method substantially equivalent to that described in Example 6-F, 1.9 g (62%) of crude EtSO$_2$-D,L-Phg-pro(4-cis-phenoxy)-ArgH.HCl were prepared from EtSO$_2$-D,L-Phg-pro(4-cis-phenoxy)-Arg(Cbz)lactam. Diastereomeric separation was achieved upon RPHPLC purification using RPHPLC Method A. A load of 1 g of EtSO$_2$-D,L-Phg-Pro(4-cis-phenoxy)-ArgH.HCl yielded 0.1 g (10%) of EtSO$_2$-L-Phg-Pro(4-cis-phenoxy)-ArgH.HCl.

$^1$H NMR

FAB-MS m/e 573 (MH$^+$)

Analysis for $C_{27}H_{36}N_6O_6S$.1.5 HCl.0.5 H$_2$O: Calc: C, 50.96; H, 6.10; N, 13.21; Found: C, 50.90; H, 6.15; N, 12.81.

40
EXAMPLE 17

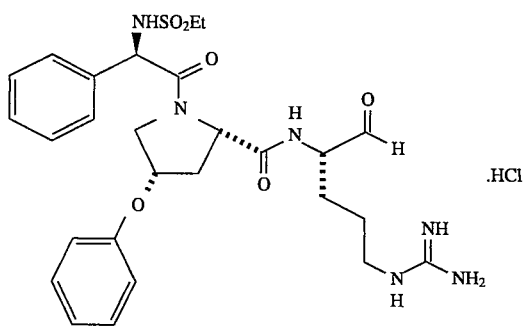

Synthesis of
EtSO$_2$-D-Phg-Pro(4-cis-phenoxy)-ArgH.HCl

From the HPLC separation described in Example 16-G, 0.06 g (6%) of EtSO$_2$-D-Phg-Pro(4-cis-phenoxy)-ArgH.HCl were isolated.

$^1$H NMR

FAB-MS m/e 573 (MH$^+$)

Analysis for $C_{27}H_{36}N_6O_6S$.HCl: Calc: C, 53.24; H, 6.12; N, 13.80; Found: C, 53.14; H, 5.88; N, 13.60.

EXAMPLE 18

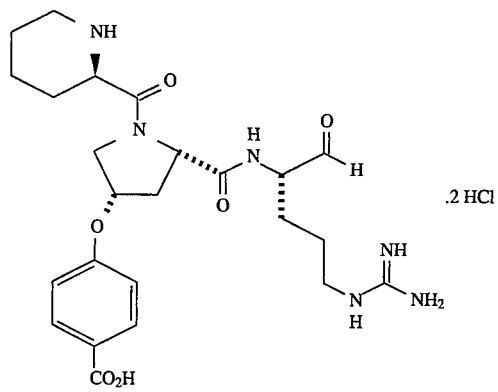

Synthesis of
D-hPro-Pro(4-cis-(4-COOH-phenoxy))-ArgH.2 HCl

A) Preparation of Cbz-D-hPro-Pro(4-trans-hydroxy)-OH.

By a method substantially equivalent to that described in Example 1-G, 54.5 g (67%) of Cbz-D-hPro-Pro(4-trans-hydroxy)-OH were prepared from Cbz-D-hPro-Pro(4-trans-hydroxy)-OEt.

$^1$H NMR

FD-MS m/e 377 (MH$^+$)

Analysis for $C_{19}H_{24}N_2O_6$: Calc: C, 60.63; H, 6.43; N, 7.44; Found: C, 60.65; H, 6.48; N, 7.44.

B) Preparation of Cbz-D-hPro-Pro(4-trans-hydroxy)-OCHPh$_2$.

To a solution of Cbz-D-hPro-Pro(4-trans-hydroxy)-OH (50 g, 133 mmol) in THF (1 L) was added diphenyl diazomethane (40 g, 200 mmol). The mixture was allowed to stir for 16 hours and the solvents were removed in vacuo. The residue was partitioned between ethyl acetate and saturated aqueous NaHCO$_3$. The layers were separated and the organic layer was washed once with saturated aqueous NaHCO$_3$, dried with MgSO$_4$, filtered and concentrated. The

41 resulting yellow residue was chromatographed over silica gel (1 kg) with a step gradient of 1:1 ethyl acetate/hexanes through ethyl acetate. The product containing fractions as judged by TLC were combined and concentrated in vacuo to give 70 g (97%) of a foam.

$^1$H NMR

FD-MS m/e 543 (M$^+$)

Analysis for $C_{32}H_{34}N_2O_6$: Calc: C, 70.83; H, 6.32; N, 5.16; Found: C, 70.99; H, 6.43; N, 5.22.

C) Preparation of Cbz-D-hPro-Pro(4-cis-(4-COOBn-phenoxy))-OCHPh$_2$.

By a method substantially equivalent to that described in Example 8-A, 28.5 g (95%) of Cbz-D-hPro-Pro(4-cis-(4-COOBn-phenoxy))-OCHPh$_2$ were prepared from Cbz-D-hPro-Pro(4-trans-hydroxy)-OCHPh$_2$. Product was contaminated with 1,2-carbethoxyhydrazine as it coeluted with the product during silica gel chromatography.

$^1$H NMR

FD-MS m/e 754 (MH$^+$)

D) Preparation of Cbz-D-hPro-Pro(4-cis-(4-COOBn-phenoxy))-OH.

To a solution of Cbz-D-hPro-Pro(4-cis-(4-COOBn-phenoxy))-OCHPh$_2$ (28 g, 37 mmol) in dichloromethane (150 mL) was added anisole (15 mL) and trifluoroacetic acid (150 mL). The mixture was allowed to stir for several hours at room temperature. The solvents were removed in vacuo and the resulting oil was partitioned between saturated aqueous NaHCO$_3$ and diethyl ether. The layers were separated and the organic phase was extracted once with saturated aqueous NaHCO$_3$. The combined aqueous phase was adjusted to pH 2 with 5N aqueous HCl and extracted three times with ethyl acetate (600 mL). The combined ethyl acetate extracts were dried with MgSO$_4$, filtered, and concentrated to give a colorless oil (21 g, 97%).

$^1$H NMR

FD-MS m/e 587 (M$^+$)

E) Preparation of Cbz-D-hPro-Pro(4-cis-(4-COOBn-phenoxy))-Arg(Cbz)lactam.

By a method substantially equivalent to that described in Example 1-K, 4.2 g (20%) of Cbz-D-hPro-Pro(4-cis-(4-COOBn-phenoxy))-Arg(Cbz)lactam were prepared from Cbz-D-hPro-Pro(4-cis-(4-COOBn-phenoxy))-OH and Arg(Cbz)lactam.2 HCl.

$^1$H NMR

FD-MS m/e 858 (M$^+$)

F) Preparation of Cbz-D-hPro-Pro(4-cis-(4-COOH-phenoxy))-ArgH.2 HCl.

By a method substantially equivalent to that described in Example 6-F, 1.6 g (79%) of crude Cbz-D-hPro-Pro(4-cis-(4-COOH-phenoxy))-ArgH.2 HCl were prepared from Cbz-D-hPro-Pro(4-cis-(4-COOBn-phenoxy))-Arg(Cbz)lactam.

$^1$H NMR

FAB-MS m/e 503 (MH$^+$)

Analysis for $C_{24}H_{36}N_6O_6$.2 HCl.H$_2$O: Calc: C, 48.57; H, 6.45; N, 14.16; Found: C, 48.21; H, 6.13; N, 14.07.

42

EXAMPLE 19

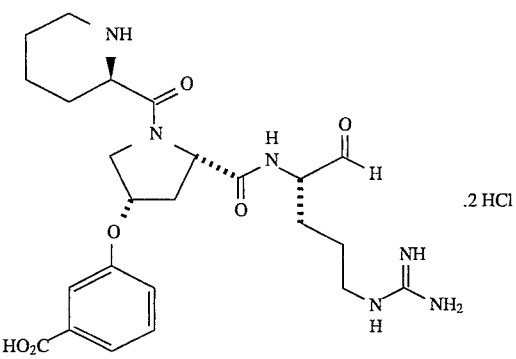

Synthesis of D-hPro-Pro(4-cis-(3-COOH-phenoxy))-ArgH.2 HCl

A) Preparation of benzyl 3-hydroxybenzoate.

To a solution of 3-hydroxybenzoic acid (27.6 g, 200 mmol) in DMF (500 mL) was added KHCO$_3$ (20 g, 200 mmol). An addition funnel was charged with benzyl bromide (21.7 mL, 200 mmol). This was added dropwise over a period of 10 minutes and the mixture was allowed to stir 16 hours at room temperature. The solvent was removed in vacuo and the residue was partitioned between EtOAc (750 mL) and water (500 mL) and the layers separated. The organic phase was washed once with 1N citric acid (500 mL), twice with saturated aqueous NaHCO$_3$ (500 mL), and twice with brine (500 mL). The organic solution was dried (MgSO$_4$), filtered and concentrated in vacuo to give 42 g (93%) of a straw colored syrup which crystallized upon standing.

$^1$H NMR

FD-MS m/e 228 (M$^+$)

B) Preparation of Cbz-D-hPro-Pro(4-cis-(3-COOBn-phenoxy))-OCHPh$_2$.

By a method substantially equivalent to that described in Example 8-A, 29.1 g (97%) of Cbz-D-hPro-Pro(4-cis-(3-COOBn-phenoxy))-OCHPh$_2$ were prepared from Cbz-D-hPro-Pro(4-trans-hydroxy)-OCHPh$_2$.

$^1$H NMR

FD-MS m/e 754 (MH$^+$)

C) Preparation of Cbz-D-hPro-Pro(4-cis-(3-COOBn-phenoxy))-OH.

By a method substantially equivalent to that described in Example 16-D, 22.4 g (97%) of Cbz-D-hPro-Pro(4-cis-(3-COOBn-phenoxy))-OH were prepared.

$^1$H NMR

FD-MS m/e 587 (M$^+$)

D) Preparation of Cbz-D-hPro-Pro(4-cis-(3-COOBn-phenoxy))-Arg(Cbz)lactam.

By a method substantially equivalent to that described in Example 1-K, 8.8 g (41%) of Cbz-D-hPro-Pro(4-cis-(3-COOBn-phenoxy))-Arg(Cbz)lactam were prepared from Cbz-D-hPro-Pro(4-cis-(3-COOBn-phenoxy))-OH and Arg(Cbz)lactam.2 HCl.

$^1$H NMR

FD-MS m/e 858 (M$^+$)

Analysis for $C_{47}H_{50}N_6O_{10}$: Calc: C, 65.72; H, 5.87; N, 9.78; Found: C, 65.43; H, 5.86; N, 9.73.

E) Preparation of Cbz-D-hPro-Pro(4-cis-(4-COOH-phenoxy))-ArgH.2 HCl.

By a method substantially equivalent to that described in Example 6-F, 1.6 g (80%) of crude Cbz-D-hPro-Pro(4-cis- (3-COOH-phenoxy))-ArgH.2 HCl were prepared from Cbz-D-hPro-Pro(4-cis-(4-COOBn-phenoxy))-Arg(Cbz)lactam.

¹H NMR

FAB-MS m/e 503 (MH⁺)

Analysis for $C_{24}H_{36}N_6O_6$.2 HCl.0.5 $H_2O$: Calc: C, 49.32; H, 6.38; N, 14.38; Found: C, 49.14; H, 6.30; N, 14.56.

EXAMPLE 20

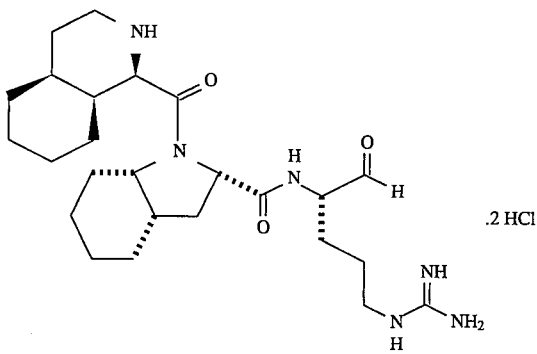

Synthesis of D-1-cis-Piq-cis-Ohi-ArgH.2 HCl

A) Preparation of Cbz-D-1-cis-Piq-cis-Ohi-OEt.

By a method substantially equivalent to that described in Example 1-F, a mixture of Cbz-D-1-cis-Piq-cis-Ohi-OEt and Cbz-L-1-cis-Piq-cis-Ohi-OEt was prepared from Cbz-D-1-cis-Piq-OH and (S)-cis-octahydroindole-2-carboxylic acid ethyl ester.HCl. These diastereomers were separated by silica gel chromatography using an ethyl acetate/hexanes gradient. Fractions containing the leading diastereomer ($R_f$= 0.35; 30% ethyl acetate/hexanes) were combined and concentrated to give 4.2 g (27%) of a white foam.

¹H NMR

FD-MS m/e 496 (M⁺)

Analysis for $C_{29}H_{40}N_2O_5$: Calc: C, 70.13; H, 8.12; N, 5.64; Found: C, 69.96; H, 8.23; N, 5.73.

B) Preparation of D-1-cis-Piq-cis-Ohi-ArgH.2 HCl.

By methods substantially equivalent to those described in Example 1-G, 1-K, and 1-L, 2.8 g (85%) of crude D-1-cis-Piq-cis-Ohi-ArgH.2 HCl were prepared from Cbz-D-1-cis-Piq-cis-Ohi-OEt. RPHPLC method A was used to purify 2.0 g of this material and 1.0 g (50%) of pure D-1-cis-Piq-cis-Ohi-ArgH.2 HCl was obtained.

¹H NMR

FAB-MS m/e 475 (MH⁺)

Analysis for $C_{25}H_{42}N_6O_3$.2 HCl: Calc: C, 54.84; H, 8.10; N, 15.35; Found: C, 54.62; H, 8.03; N, 15.31.

EXAMPLE 21

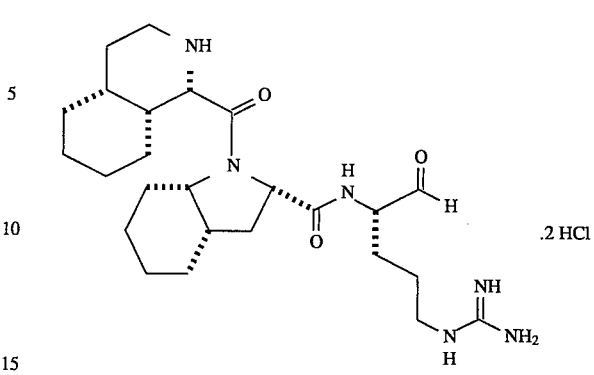

Synthesis of L-1-cis-Piq-cis-Ohi-ArgH.2 HCl

A) Preparation of Cbz-L-1-cis-Piq-cis-Ohi-OEt.

Following the chromatography of Example 20-A, fractions containing the trailing diastereomer ($R_f$=0.25; 30% ethyl acetate/hexanes) were combined and concentrated in vacuo to give 4.6 g (29%) of Cbz-L-1-cis-Piq-cis-Ohi-OEt as a white foam.

¹H NMR

FD-MS m/e 496 (M⁺)

Analysis for $C_{29}H_{40}N_2O_5$: Calc: C, 70.13; H, 8.12; N, 5.64; Found: C, 69.22; H, 7.98; N, 6.10.

B) Preparation of L-1-cis-Piq-cis-Ohi-ArgH.2 HCl.

By methods substantially equivalent to those described in Example 1-G, 1-K, and 1-L, 3.5 g (90%) of crude L-1-cis-Piq-cis-Ohi-ArgH.2 HCl were prepared from Cbz-L-1-cis-Piq-cis-Ohi-OEt. RPHPLC method A was used to purify 2.0 g of this material and 1.0 g (50%) of pure D-1-cis-Piq-cis-Ohi-ArgH.2 HCl was obtained.

¹H NMR

FAB-MS m/e 475 (MH⁺)

Analysis for $C_{25}H_{42}N_6O_3$.2 HCl: Calc: C, 54.84; H, 8.10; N, 15.35; Found: C, 54.69; H, 8.06; N, 15.30.

EXAMPLE 22

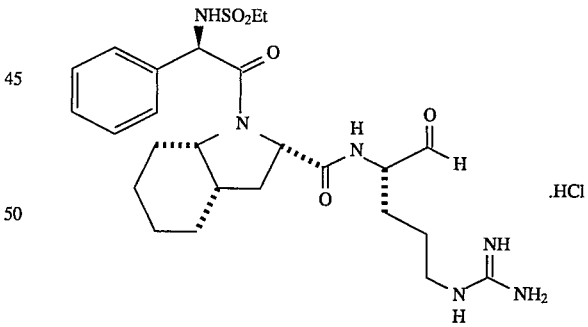

Synthesis of $EtSO_2$-D-Phg-cis-Ohi-ArgH.HCl

A) Preparation of Boc-D-Phg-cis-Ohi-OEt

By a method substantially equivalent to that described in Example 1-D, 14.9 g (58%) of Boc-D-Phg-cis-Ohi-OEt was prepared from Boc-D-Phg-OH and (S)-cis-octahydroindole-2-carboxylic acid ethyl ester-HCl.

¹H NMR
FD-MS m/e 430 (M⁺)
Analysis for C₂₄H₃₄N₂O₅: Calc: C, 66.95; H, 7.96; N, 6.51; Found: C, 66.69; H, 8.02; N, 6.40.

B) Preparation of D-Phg-cis-Ohi-OEt.HCl.

To a cold (0° C.), stirring solution of Boc-D-Phg-cis-Ohi-OEt in ethyl acetate was bubbled HCl gas for 10 minutes. After stirring for 2 hrs while warming to room temperature, the solvent was removed in vacuo. The resulting solid was suspended in diethyl ether and subsequently isolated by filtration to give 10.7 g (97%) of D-Phg-cis-Ohi-OEt.HCl.

¹NMR
FD-MS m/e 331 (M⁺)
Analysis for C₁₉H₂₇N₂O₃Cl: Calc: C, 62.20; H, 7.41; N, 7.64; Found: C, 62.42; H, 7.36; N, 7.85.

C) Preparation of EtSO₂-D-Phg-cis-Ohi-OEt.

To a solution of D-Phg-cis-Ohi-OEt.HCl (10 g, 27 mmol) and diisopropylethylamine (10.7 mL, 61 mmol) in THF (200 mL) at −78° C., was added dropwise via an addition funnel a solution of ethanesulfonyl chloride (3.9 g, 30 mmol) in THF (20 mL). The cold bath was then left unattended and the solution warmed slowly to room temperature. After about 18 h, the solution was concentrated in vacuo. The residue was dissolved in ethyl acetate (200 mL), washed twice with each 1N citric acid (200 mL), saturated aqueous NaHCO₃ (200 mL) and brine (200 mL). The organic phase was then dried with MgSO₄, filtered, and concentrated in vacuo to give 11.2 g (97%) of a yellow foam.

¹H NMR
FD-MS m/e 422 (M⁺)
Analysis for C₂₁H₃₀N₂O₅S: Calc: C, 59.69; H, 7.16; N, 6.63; Found: C, 59.94; H, 7.08; N, 6.78.

D) Preparation of EtSO₂-D-Phg-cis-Ohi-ArgH.HCl

By methods substantially equivalent to those described in Example 1-G, 1-K, and 1-L, 3.5 g (90%) of crude L-1-cis-Piq-cis-Ohi-ArgH.2 HCl were prepared from Cbz-L-1-cis-Piq-cis-Ohi-OEt. RPHPLC method A was used to purify 2.0 g of this material and 0.35 g (18%) of pure EtSO₂-D-Phg-cis-Ohi-ArgH.HCl was obtained.

¹H NMR
FAB-MS m/e 535 (MH⁺)
Analysis for C₂₅H₃₈N₆O₅S.HCl: Calc: C, 52.58; H, 6.88; N, 14.71; Found: C, 52.30; H, 6.72; N, 14.45.

EXAMPLE 23

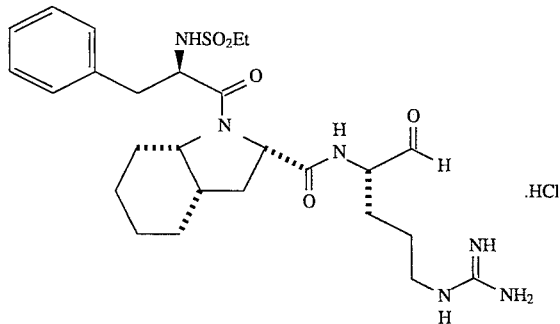

Synthesis of EtSO₂-D-Phe-cis-Ohi-ArgH.HCl

A) Preparation of EtSO₂-D-Phe-cis-Ohi-ArgH.HCl

By methods substantially equivalent to those described in Example 22, 2.35 g of crude EtSO₂-D-Phe-cis-Ohi-ArgH-.HCl was prepared from Boc-D-Phe-OH in place of Boc-D-Phg-OH. RPHPLC method A was used to purify 2.0 g of this material and 0.92 g (46%) of pure EtSO₂-D-Phe-cis-Ohi-ArgH.HCl was obtained.

¹H NMR
FAB-MS m/e 549.5 (MH⁺)
Analysis for C₂₆H₄₀N₆O₅S.HCl: Calc: C, 53.37; H, 7.06; N, 14.36; Found: C, 53.61; H, 6.90; N, 14.28.

EXAMPLE 24

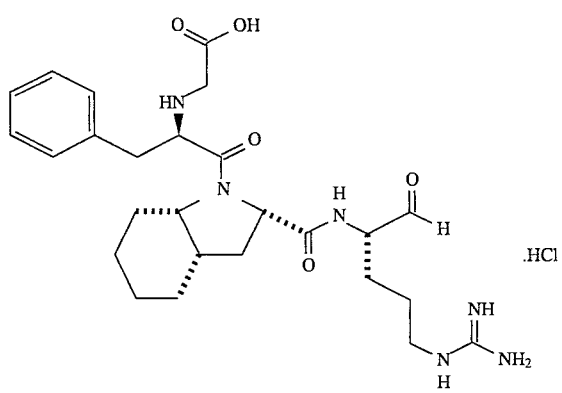

Synthesis of HOOCCH₂-D-Phe-cis-Ohi-ArgH.HCl

A) Preparation t-BuOOCCH₂-D-Phe-cis-Ohi-OEt.

To a solution of D-Phe-cis-Ohi-OEt.HCl (30 g, 79 mmol) in acetonitrile (400 mL) was added diisopropylethylamine (41 mL, 236 mmol) and t-butyl bromoacetate (14 mL, 87 mmol). This solution was brought to reflux and maintained there for 3 hrs. After cooling to room temp, the solution was concentrated in vacuo. The residue was dissolved in ethyl acetate (300 mL) and this solution was washed twice with saturated aqueous ammonium chloride (200 mL), twice with saturated aqueous sodium bicarbonate (200 mL), and twice with brine (200 mL). The organic layer was dried (MgSO₄), filtered, and concentrated in vacuo to give an orange oil which was purified by silica gel chromatography eluting with a gradient of hexanes to 1:1 hexanes/ethyl acetate. Fractions containing product (as judged by TLC) were combined and concentrated to give 33.2 g (92%) of a colorless oil.

¹H NMR
FD-MS m/e 458 (M⁺)
Analysis for C₂₆H₃₈N₂O₅: Calc: C, 68.10; H, 8.35; N, 6.11; Found: C, 68.37; H, 8.47; N, 5.90.

B) Preparation of Boc-t-BuOOCCH₂-D-Phe-cis-Ohi-OH.

To a solution of t-BuOOCCH₂-D-Phe-cis-Ohi-OEt (30 g, 65 mmol) in THF (200 mL) was added diisopropylethylamine (17 mL, 98 mmol) and di-t-butyl dicarbonate (15.7 g, 72 mmol). This solution was brought to gentle reflux and maintained for 16 hrs. Heating was discontinued, and once cool, the solution was concentrated in vacuo. The residue was dissolved in ethyl acetate (400 mL) and washed twice with 1.0M citric acid (200 mL), twice with saturated aqueous sodium bicarbonate (200 mL), and twice with brine (200 mL). The organic solution was dried (MgSO₄), filtered, and concentrated in vacuo to give a yellow oil. A portion of this oil (24.8 g, 44 mmol) was dissolved in 300 mL of dioxane. To this was added a solution consisting of 2.05 g LiOH.H₂O (49 mmol) in 150 mL water. This mixture was allowed to stir for 5 hrs at room temp at which time 100 mL of saturated aqueous ammonium chloride was added. Solvents were removed in vacuo and the residue was partitioned between saturated aqueous sodium bicarbonate and diethyl ether. The layers were separated and the aqueous layer was acidified to pH 3 with citric acid. The acidic aqueous solution was extracted 3 times with diethyl ether (200 mL) and these were combined, dried (MgSO$_4$), filtered and concentrated to give 24.3 g of Boc-t-BuOOCCH$_2$-D-Phe-cis-Ohi-OH as a white foam.

$^1$H NMR
FD-MS m/e 530 (M$^+$)
Analysis for C$_{29}$H$_{42}$N$_2$O$_7$: Calc: C, 65.64; H, 7.98; N, 5.28; Found: C, 65.39; H, 8.04; N, 5.39.

C) Preparation of Boc-t-BuOOCCH$_2$-D-Phe-cis-Ohi-Arg(Cbz)lactam.

By a method substantially equivalent to that described in Example 1-K, 4.7 g (39%) of Boc-t-BuOOCCH$_2$-D-Phe-cis-Ohi-Arg(Cbz)lactam were prepared.

$^1$H NMR
FD-MS m/e 802 (M$^+$)
Analysis for C$_{43}$H$_{58}$N$_6$O$_9$: Calc: C, 64.32; H, 7.28; N, 10.47; Found: C, 64.34; H, 7.53; N, 10.24.

D) Preparation of HOOCCH$_2$-D-Phe-cis-Ohi-ArgH.HCl.

By a method substantially equivalent to that described in Example 1-L, crude Boc-t-BuOOCCH$_2$-D-Phe-cis-Ohi-ArgH.HCl was prepared from Boc-t-BuOOCCH$_2$-D-Phe-cis-Ohi-Arg(Cbz)lactam. The residue was redissolved in 5% anisole/trifluoroacetic acid at 0° C. This was allowed to stir cold for 1 hour at which time the solvent was removed in vacuo. The residue was taken into 0.1N HCl and washed twice with diethyl ether. The aqueous layer was concentrated to a volume of 30 mL and the product was then purified by RPHPLC Method A to give 1.2 g (44%) of pure HOOCCH$_2$-D-Phe-cis-Ohi-ArgH.HCl.

$^1$H NMR
FAB-MS m/e 515.6 (MH$^+$)
Analysis for C$_{26}$H$_{38}$N$_6$O$_5$.3 HCl: Calc: C, 55.56; H, 7.05; N, 14.95; Found: C, 55.83; H, 6.67; N, 14.78.

EXAMPLE 25

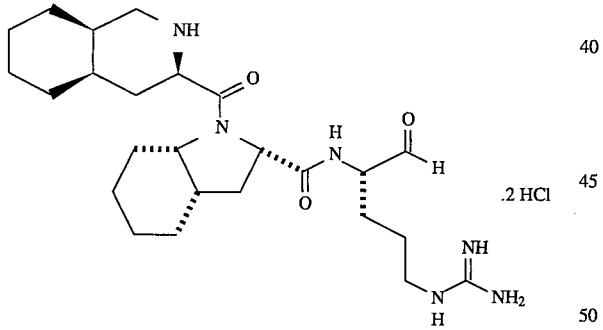

Synthesis of D-3-cis-Piq-cis-Ohi-ArgH.2 HCl

A) Preparation of Cbz-D-3-cis-Piq-OH.

D-Phenylalanine (50 g, 302 mmol) was reacted with a 37% solution of formaldehyde (120 mL) and concentrated HCl (380 mL) at reflux. After 30 minutes an additional 50 mL of formaldehyde was added and reaction continued for 3 hours. The reaction cooled to −10° C. and the precipitate was filtered. The solid was dried in vacuo to give D-1,2,3,4-tetrahydro-3isoquinolinecarboxylic acid (24.2 g, 45%) FD-MS 178 (MH$^+$).

A solution of D-1,2,3,4-tetrahydro-3-isoquinolinecarboxylic acid (17 g, 96 mmol) in water (200 mL) and 20 mL of 5N HCl was reacted with hydrogen over 5% Rh/Al$_2$O$_3$ (8.5 g) at 2000 psi (138 bar) in a high pressure apparatus at 120° C. for 16 hours. The reaction mixture was filtered through a diatomaceous earth pad, and the filtrate was freeze-dried to give D-perhydro-3-isoquinolinecarboxylic acid (D-3-Piq-OH) (21 g, 100%) FD-MS 184 (MH$^+$).

D-3-Piq-OH (21.0 g, 95.8 mmol) was dissolved in tetrahydrofuran (75 mL) and water (50 mL). The pH of the solution was adjusted to 10.0 with 5N NaOH and benzyl chloroformate (16.4 mL, 115 mmol) was added dropwise and the pH maintained at 9.5 with 2N NaOH. The reaction was stirred for an additional 1 hour at room temperature. The organic solvent was evaporated in vacuo, and diethyl ether (100 mL) and water (50 mL) were added to the residue. The aqueous layer was separated, the pH of the solution was adjusted to 3.0 with 3N HCl, and ethyl acetate (250 mL) was added. The organic layer was separated and dried (MgSO$_4$). The filtrate was concentrated in vacuo to give a clear oil of Cbz-D-perhydro-3-isoquinolinecarboxylic acid (Cbz-D-3-Piq-OH) (25.8 g, 85%).

$^1$H NMR
FD-MS m/e 318 (MH$^+$)

B) Preparation of D-3-cis-Piq-cis-Ohi-ArgH.2 HCl

By methods substantially equivalent to those described in Example 1-F, 1-G, 1-K, and 1-L, 3.5 g of crude D-3-cis-Piq-cis-Ohi-ArgH.2 HCl were prepared from Cbz-D-3-cis-Piq-OH and cis-Ohi-OEt.HCl. RPHPLC method A was used to purify 2.0 g of this material and 0.87 g (44%) of pure D-3-cis-Piq-cis-Ohi-ArgH.2 HCl was obtained.

$^1$H NMR
FAB-MS m/e 475.6 (MH$^+$)
Analysis for C$_{25}$H$_{42}$N$_6$O$_3$.2 HCl: Calc: C, 54.84; H, 8.10; N, 15.35; Found: C, 55.24; H, 8.34; N, 14.96.

EXAMPLE 26

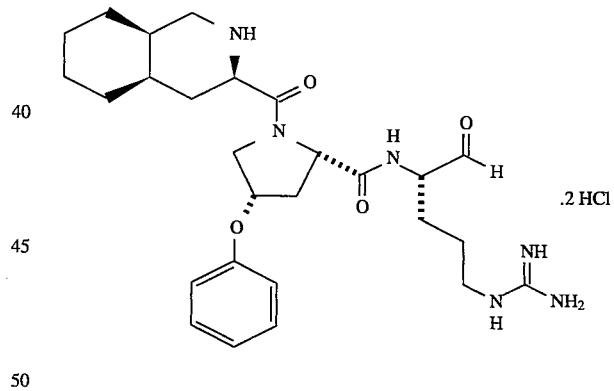

Synthesis of D-3-cis-Piq-Pro(4-cis-phenoxy)-ArgH.2 HCl

A) Preparation of D-3-cis-Piq-Pro(4-cis-phenoxy)-ArgH.2 HCl

By methods substantially equivalent to those described in Example 1-F, 1-G, 1-K, and 1-L, 3.36 g of crude D-3-cis-Piq-Pro(4-cis-phenoxy)-ArgH.2 HCl was prepared starting from Cbz-D-3-cis-Piq-OH and Pro(4-cis-phenoxy)-OMe-.HCl. RPHPLC method A was used to purify 2.0 g of this material and 1.2 g (60%) of pure D-3-cis-Piq-Pro(4-cis-phenoxy)-ArgH.2 HCl was obtained.

$^1$H NMR
FAB-MS m/e 513.6 (MH$^+$)
Analysis for C$_{27}$H$_{40}$N$_6$O$_4$.2 HCl.0.5 H$_2$O: Calc: C, 54.54; H, 7.29; N, 14.13; Found: C, 54.51; H, 7.22; N, 14.03.

EXAMPLE 27

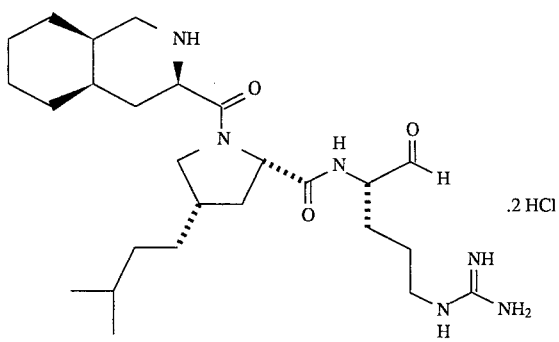

Synthesis of D-3-cis-Piq-Pro(4-cis-isoamyl)-ArgH.2 HCl

A) Preparation of D-3-cis-Piq-Pro(4-cis-isoamyl)ArgH.2 HCl.

By methods substantially equivalent to those described in Example 1-F, 1-G, 1-K, and 1-L, 2.9 g of crude D-3-cis-Piq-Pro(4-cis-isoamyl)-ArgH.2 HCl was prepared starting from Cbz-D-3-cis-Piq-OH and Pro(4-cis-isoamyl)-OEt.HCl. RPHPLC method A was used to purify 2.0 g of this material and 1.0 g (50%) of pure D-3-cis-Piq-Pro(4-cis-isoamyl)-ArgH.2 HCl was obtained.

$^1$H NMR

FAB-MS m/e 491.4 (MH$^+$)

Analysis for $C_{26}H_{46}N_6O_3$.2 HCl: Calc: C, 55.41; H, 8.58; N, 14.91; Found: C, 55.32; H, 8.35; N, 14.94.

EXAMPLE 28

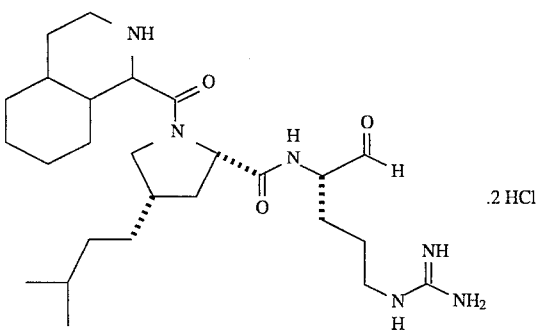

Synthesis of 1-Piq-Pro(4-cis-isoamyl)-ArgH.2 HCl

A) Preparation of 1-Piq-Pro(4-cis-isoamyl)-ArgH.2 HCl

By methods substantially equivalent to those described in Example 1-F, 1-G, 1-K, and 1-L, 2.9 g of crude 1-Piq-Pro(4-cis-isoamyl)-ArgH.2 HCl was prepared starting from Cbz-D,L-1-cis-Piq-OH and Pro(4-cis-isoamyl)-OEt.HCl. RPHPLC method A was used to purify 2.0 g of this material and 1.0 g (50%) of pure 1-Piq-Pro(4-cis-isoamyl)-ArgH.2 HCl was obtained.

$^1$H NMR

FAB-MS m/e 491.4 (MH$^+$)

Analysis for $C_{26}H_{46}N_6O_3$.2 HCl.0.5 $H_2O$: Calc: C, 54.54; H, 8.62; N, 14.68; Found: C, 54.77; H, 8.61; N, 14.29.

In the same way as described above can be prepared the following compounds:

EtSO$_2$-D-Phe-Pro(4-cis-isoamyl)-ArgH
EtSO$_2$-D-Phe-Pro(4-cis-PhO)-ArgH
EtSO$_2$-D-Phe-Pro(4-cis-methyl)-ArgH
EtSO$_2$-D-Phe-Pro(4-cis-ethyl)-ArgH
EtSO$_2$-D-Phe-Pro(4-cis-n-propyl)-ArgH
EtSO$_2$-D-Phe-Abo-ArgH
EtSO$_2$-D-Phe-Pro(4-cis-(4-COOH)PhO)-ArgH
EtSO$_2$-D-Phe-Pro(4-cis-(3-COOH)PhO)-ArgH
EtSO$_2$-D-Phe-Pro(4-cis-CH$_2$COOH)-ArgH
EtSO$_2$-D-Phg-Pro(4-cis-isoamyl)-ArgH
EtSO$_2$-D-Phg-Pro(4-cis-methyl)-ArgH
EtSO$_2$-D-Phg-Pro(4-cis-ethyl)-ArgH
EtSO$_2$-D-Phg-Pro(4-cis-n-propyl)-ArgH
EtSO$_2$-D-Phg-Abo-ArgH
EtSO$_2$-D-Phg-Pro(4-cis-(4-COOH)PhO)-ArgH
EtSO$_2$-D-Phg-Pro(4-cis-(3-COOH)PhO)-ArgH
EtSO$_2$-D-Phg-Pro(4-cis-CH$_2$COOH)-ArgH
EtSO$_2$-D-Cha-Ohi-ArgH
EtSO$_2$-D-Cha-Pro(4-cis-isoamyl)-ArgH
EtSO$_2$-D-Cha-Pro(4-cis-PhO)-ArgH
EtSO$_2$-D-Cha-Pro(4-cis-methyl)-ArgH
EtSO$_2$-D-Cha-Pro(4-cis-ethyl)-ArgH
EtSO$_2$-D-Cha-Pro(4-cis-n-propyl)-ArgH
EtSO$_2$-D-Cha-Abo-ArgH
EtSO$_2$-D-Cha-Pro(4-cis-(4-COOH)PhO)-ArgH
EtSO$_2$-D-Cha-Pro(4-cis-(3-COOH)PhO)-ArgH
EtSO$_2$-D-Cha Pro(4-cis-CH$_2$COOH)-ArgH
EtSO$_2$-D-Chg-Ohi-ArgH
EtSO$_2$-D-Chg-Pro(4-cis-isoamyl)-ArgH
EtSO$_2$-D-Chg-Pro(4-cis-PhO)-ArgH
EtSO$_2$-D-Chg-Pro(4-cis-methyl)-ArgH
EtSO$_2$-D-Chg-Pro(4-cis-ethyl)-ArgH
EtSO$_2$-D-Chg-Pro(4-cis-n-propyl)-ArgH
EtSO$_2$-D-Chg-Abo-ArgH
EtSO$_2$-D-Chg-Pro(4-cis-(4-COOH)PhO)-ArgH
EtSO$_2$-D-Chg-Pro(4-cis-(3-COOH)PhO)-ArgH
EtSO$_2$-D-Chg-Pro(4-cis-CH$_2$COOH)-ArgH
HO$_2$CCH$_2$SO$_2$-D-Phe-Ohi-ArgH
HO$_2$CCH$_2$SO$_2$-D-Phe-Pro(4-cis-isoamyl)-ArgH
HO$_2$CCH$_2$SO$_2$-D-Phe-Pro(4-cis-PhO)-ArgH
HO$_2$CCH$_2$SO$_2$-D-Phe-Pro(4-cis-methyl)-ArgH
HO$_2$CCH$_2$SO$_2$-D-Phe-Pro(4-cis-ethyl)-ArgH
HO$_2$CCH$_2$SO$_2$-D-Phe-Pro(4-cis-n-propyl)-ArgH
HO$_2$CCH$_2$SO$_2$-D-Phe-Abo-ArgH
HO$_2$CCH$_2$SO$_2$-D-Phe-Pro(4-cis-(4-COOH)PhO)-ArgH
HO$_2$CCH$_2$SO$_2$-D-Phe-Pro(4-cis-(3-COOH)PhO)-ArgH
HO$_2$CCH$_2$SO$_2$-D-Phe-Pro(4-cis-CH$_2$COOH)-ArgH
HO$_2$CCH$_2$SO$_2$-D-Phg-Pro(4-cis-isoamyl)-ArgH
HO$_2$CCH$_2$SO$_2$-D-Phg-Pro(4-cis-PhO-ArgH
HO$_2$CCH$_2$SO$_2$-D-Phg-Pro(4-cis-methyl)-ArgH
HO$_2$CCH$_2$SO$_2$-D-Phg-Pro(4-cis-ethyl)-ArgH
HO$_2$CCH$_2$SO$_2$-D-Phg-Pro(4-cis-n-propyl)-ArgH
HO$_2$CCH$_2$SO$_2$-D-Phg-Abo-ArgH
HO$_2$CCH$_2$SO$_2$-D-Phg-Pro(4-cis-(4-COOH)PhO)-ArgH
HO$_2$CCH$_2$SO$_2$-D-Phg-Pro(4-cis-(3-COOH)PhO)-ArgH
HO$_2$CCH$_2$SO$_2$-D-Phg-Pro(4-cis-CH$_2$COOH)-ArgH
HO$_2$CCH$_2$SO$_2$-D-Cha-Ohi-ArgH
HO$_2$CCH$_2$SO$_2$-D-Cha-Pro(4-cis-isoamyl)-ArgH
HO$_2$CCH$_2$SO$_2$-D-Cha-Pro(4-cis-PhO)-ArgH
HO$_2$CCH$_2$SO$_2$-D-Cha-Pro(4-cis-methyl)-ArgH
HO$_2$CCH$_2$SO$_2$-D-Cha-Pro(4-cis-ethyl)-ArgH
HO$_2$CCH$_2$SO$_2$-D-Cha-Pro(4-cis-n-propyl)-ArgH
HO$_2$CCH$_2$SO$_2$-D-Cha-Abo-ArgH
HO$_2$CCH$_2$SO$_2$-D-Cha-Pro(4-cis-(4-COOH)PhO)-ArgH
HO$_2$CCH$_2$SO$_2$-D-Cha-Pro(4-cis-(3-COOH)PhO)-ArgH
HO$_2$CCH$_2$SO$_2$-D-Cha-Pro(4-cis-CH$_2$COOH)-ArgH
HO$_2$CCH$_2$SO$_2$-D-Chg-Ohi-ArgH
HO$_2$CCH$_2$SO$_2$-D-Chg-Pro(4-cis-isoamyl)-ArgH
HO$_2$CCH$_2$SO$_2$-D-Chg-Pro(4-cis-PhO)-ArgH HO₂CCH₂SO₂-D-Chg-Pro(4-cis-methyl)-ArgH
HO₂CCH₂SO₂-D-Chg-Pro(4-cis-ethyl)-ArgH
HO₂CCH₂SO₂-D-Chg-Pro(4-cis-n-propyl)-ArgH
HO₂CCH₂SO₂-D-Chg-Abo-ArgH
HO₂CCH₂SO₂-D-Chg-Pro(4-cis-(4-COOH)PhO)-ArgH
HO₂CCH₂SO₂-D-Chg-Pro(4-cis-(3-COOH)PhO)-ArgH
HO₂CCH₂SO₂-D-Chg-Pro(4-cis-CH₂COOH)-ArgH
HO₂CCH₂-D-Phe-Pro(4-cis-isoamyl)-ArgH
HO₂CCH₂-D-Phe-Pro(4-cis-PhO)-ArgH
HO₂CCH₂-D-Phe-Pro(4-cis-methyl)-ArgH
HO₂CCH₂-D-Phe-Pro(4-cis-ethyl)-ArgH
HO₂CCH₂-D-Phe-Pro(4-cis-n-propyl)-ArgH
HO₂CCH₂-D-Phe-Abo-ArgH
HO₂CCH₂-D-Phe-Pro(4-cis-(4-COOH PhO)-ArgH
HO₂CCH₂-D-Phe-Pro(4-cis-(3-COOH)PhO)-ArgH
HO₂CCH₂-D-Phe-Pro(4-cis-CH₂COOH)-ArgH
HO₂CCH₂-D-Phg-Pro(4-cis-isoamyl)-ArgH
HO₂CCH₂-D-Phg-Pro(4-cis-PhO)-ArgH
HO₂CCH₂-D-Phg-Pro(4-cis-methyl)-ArgH
HO₂CCH₂-D-Phg-Pro(4-cis-ethyl)-ArgH
HO₂CCH₂-D-Phg-Pro(4-cis-n-propyl)-ArgH
HO₂CCH₂-D-Phg-Abo-ArgH
HO₂CCH₂-D-Phg-Pro(4-cis-(4-COOH)PhO)-ArgH
HO₂CCH₂-D-Phg-Pro(4-cis-(3-COOH)PhO)-ArgH
HO₂CCH₂-D-Phg-Pro(4-cis-CH₂COOH)-ArgH
HO₂CCH₂-D-Cha-Ohi-ArgH
HO₂CCH₂-D-Cha-Pro(4-cis-isoamyl)-ArgH
HO₂CCH₂-D-Cha-Pro(4-cis-PhO)-ArgH
HO₂CCH₂-D-Cha-Pro(4-cis-methyl)-ArgH
HO₂CCH₂-D-Cha-Pro(4-cis-ethyl)-ArgH
HO₂CCH₂-D-Cha-Pro(4-cis-n-propyl)-ArgH
HO₂CCH₂-D-Cha-Abo-ArgH
HO₂CCH₂-D-Cha-Pro(4-cis-(4-COOH)PhO)-ArgH
HO₂CCH₂-D-Cha-Pro(4-cis-(3-COOH)PhO)-ArgH
HO₂CCH₂-D-Cha-Pro(4-cis-CH₂COOH)-ArgH
HO₂CCH₂-D-Chg-Ohi-ArgH
HO₂CCH₂-D-Chg-Pro(4-cis-isoamyl)-ArgH
HO₂CCH₂-D-Chg-Pro(4-cis-PhO)-ArgH
HO₂CCH₂-D-Chg-Pro(4-cis-methyl)-ArgH
HO₂CCH₂-D-Chg-Pro(4-cis-ethyl)-ArgH
HO₂CCH₂-D-Chg-Pro(4-cis-n-propyl)-ArgH
HO₂CCH₂-D-Chg-Abo-ArgH
HO₂CCH₂-D-Chg-Pro(4-cis-(4-COOH)PhO)-ArgH
HO₂CCH₂-D-Chg-Pro(4-cis-(3-COOH)PhO)-ArgH
HO₂CCH₂-D-Chg-Pro(4-cis-CH₂COOH)-ArgH
1-Piq-Pro(4-cis-methyl)-ArgH
1-Piq-Pro(4-cis-ethyl)-ArgH
1-Piq-Pro(4-cis-n-propyl)-ArgH
1-Piq-Abo-ArgH
1-Piq-Pro(4-cis-(4-COOH)PhO)-ArgH
1-Piq-Pro(4-cis-(3-COOH)PhO)-ArgH
1-Piq-Pro(4-cis-CH₂COOH)-ArgH
3-Piq-Pro(4-cis-methyl)-ArgH
3-Piq-Pro(4-cis-ethyl)-ArgH
3-Piq-Pro(4-cis-n-propyl)-ArgH
3-Piq-Abo-ArgH
3-Piq-Pro(4-cis-(4-COOH)PhO)-ArgH
3-Piq-Pro(4-cis-(3-COOH)PhO)-ArgH
3-Piq-Pro(4-cis-CH₂COOH)-ArgH The compounds of the invention are believed to selectively inhibit thrombin over other fibrinolytic proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis. Further, the compounds of the present invention are believed to be orally active. The compounds may also have improved antithrombotic activity by virtue of their ability to inhibit other enzymes in the coagulation cascade, e.g., Factors IX, X, or XI.

The invention in one of its aspects provides a method of inhibiting thrombin in mammals comprising administering to a mammal in need of treatment an effective (thrombin inhibiting) dose of a compound of Formula I.

The thrombin inhibition contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disease states in which the compounds have a potential utility are in treatment or prophylaxis of thrombosis and hypercoagulability in blood and tissues. Disease states in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in prophylaxis of atherosclerotic diseases such as coronary arterial disease, cerebral arterial disease and peripheral arterial disease. Further, the compounds are expected to be useful together with thrombolytics in myocardial infarction. Further, the compounds have expected utility in the treatment or prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, and inflammatory diseases, including arthritis and diabetes. The anti-coagulant compound is administered orally, or parenterally, e.g., by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, and the condition being treated.

A typical daily dose for each of the above utilities is between about 0.01 mg/kg and about 1000 mg/kg. The dose regime may vary, e.g., for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent, e.g., tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use alone and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the reoccurrence of clot formation.

The method of this invention is also practiced in conjunction with aspirin. A compound of the invention can be administered prior to or along with aspirin or subsequent to its use to prevent the reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of Formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent, e.g., physiological saline (0.9%), 5% dextrose, Ringer's solution, and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Therefore, another embodiment of the present invention is a pharmaceutical formulation comprising an effective amount of a compound of Formula I or a pharmaceutically acceptable salt or solvate thereof in association with a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof. The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like. The compositions of this invention may be formulated so as to provide quick, sustained, or delayed release of the active ingredient after administration to the patient by employing procedures well known in the art.

The following formulation examples are illustrative only and are not intended to limit the scope of the invention in any way. "Active ingredient," of course, means a compound according to Formula I or a pharmaceutically acceptable salt or solvate thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Active ingredient | 0.25 |
| Ethanol | 25.75 |
| Propellant 22 Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The compounds provided by the invention (Formula I) are orally active and selectively inhibit the action of thrombin in mammals.

The ability of the compounds of the present invention to be effective and orally active thrombin inhibitors is evaluated in one or more of the following assays.

The inhibition of thrombin is demonstrated by in vitro inhibition of the amidase activity of thrombin as measured in an assay in which thrombin hydrolyzes the chromogenic substrate, N-benzoyl-phenylalanyl-L-valyl-L-arginyl-p-nitroanilide.

The assay is carried out by mixing 50 µL buffer (0.03M Tris, 0.15M NaCl, pH 7.4) with 25 µL of bovine thrombin or human thrombin solution (0.21 mg/mL of thrombostat bovine thrombin, Parke-Davis, or purified human thrombin, Enzyme Research Laboratories, South Bend, Ind., at about 8 NIH units/mL, in the same buffer) and 25 µL of test compound in a solvent (in 50% aqueous methanol, v:v). The 150 µL of an aqueous solution of the chromogenic substrate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

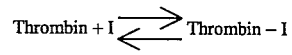

$$Kass = \frac{[Thrombin - I]}{[(Thrombin) \times (I)]}$$

Kass is calculated for a range of concentrations of test compounds and the mean value is reported in units of liter per mole.

By substantially following the procedures described above for human thrombin, and using other human blood coagulation system serine proteases and proteases of the fibrinolytic system with the appropriate chromogenic substrates, identified below, selectivity of the compounds of the present invention with respect to the coagulation factor serine proteases and with respect to the fibrinolytic system serine proteases are evaluated as well as their substantial lack of interference with serine proteases of the fibrinolytic system. Thrombin inhibitors preferably should spare fibrinolysis induced by urokinase, tissue plasminogen activator (t-PA) and streptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from KabiVitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Table 1 which follows lists the Kass values obtained with the indicated compound represented by the Formula I.

TABLE 1

| | Inhibition Properties Enzyme Kass (L/mol × $10^6$) | | | | |
|---|---|---|---|---|---|
| Example | Human Thrombin | Xa | Trypsin | Plasmin | t-PA |
| 1 | 220 | 1.4 | 390 | 0.86 | 0.077 |
| 2 | 230 | 1.7 | 520 | 1.0 | 0.097 |
| 3 | 27 | 1.7 | 260 | 0.66 | 0.14 |
| 4 | 8.2 | 7.9 | 77 | 2.0 | 0.19 |
| 5 | 110 | 5.8 | 150 | 2.1 | 0.057 |
| 6 | 2.9 | 5.7 | 240 | 5.3 | 0.065 |
| 7 | 340 | 1.6 | 150 | 1.8 | 0.053 |
| 8 | 50 | 3.0 | 270 | 2.9 | 0.069 |
| 9 | 37 | 1.6 | 130 | 1.7 | 0.055 |
| 10 | 3.0 | 0.59 | 63 | 3.4 | 0.027 |
| 11 | 28 | 0.66 | 74 | 1.4 | 0.086 |
| 12 | 6.1 | 1.2 | 56 | 1.1 | 0.015 |
| 13 | 2.1 | 0.58 | 22 | 0.65 | 0.033 |
| 14 | 8.7 | 0.48 | 6.2 | 0.34 | 0.002 |
| 15 | 230 | 2.6 | 140 | 5.1 | 0.045 |
| 16 | 43 | 6.8 | 180 | 4.8 | 0.26 |
| 17 | 2,200 | 32 | 910 | 26 | 1.5 |
| 18 | 4.5 | 0.58 | 52.2 | 0.37 | 0.013 |
| 19 | 2.8 | 1.30 | 49.3 | 0.50 | 0.022 |
| 20 | 1,630 | 0.75 | 119 | 3.67 | 0.013 |
| 21 | 3.1 | 0.03 | 3.6 | 0.20 | 0.001 |
| 22 | 6,170 | 11.8 | 312 | 27.6 | 0.085 |
| 23 | 957 | 4,37 | 312 | 28.2 | 2.07 |
| 24 | 1,160 | 1.70 | 424 | 16.3 | 0.075 |
| 25 | 82 | 0.67 | 1,040 | 12.4 | N.T. |
| 26 | 15.6 | 2.53 | 718 | 11.3 | N.T. |
| 27 | 5.4 | 11.6 | 633 | 14.0 | N.T. |
| 28 | 0.41 | 0.14 | 20.30 | 0.27 | N.T. |

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 µL thrombin (73 NIH unit/mL) to 100 µL human plasma which contains 0.0229 µCi 125-iodine labeled fibrinogen. Clot lysis is studied by overlaying the clots with 50 µL of urokinase or streptokinase (50, 100, or 1000 unit/mL) and incubating for 20 hours at room temperature. After incubation the tubes are centrifuged in a Beckman Microfuge. 25 µL of supernate is added into 1.0 mL volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/mL concentrations. Rough approximations of $IC_{50}$ values are estimated by linear extrapolations from data points to a value which would represent 50 percent of lysis for that particular concentration of fibrinolytic agent.

Anticoagulant Activity
Materials

Dog plasma and rat plasma is obtained from conscious mixed-breed hounds (either sex, Hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Ann Detroit, Mich.) is used for coagulation assays in plasma.

Methods
Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood circulated through the shunt for 15 minutes before the thread is carefully removed and weighed. The weight of a wet thread is subtracted from the total weight of the thread and thrombus (see J. R. Smith, *Br. J. PharmaCol.*, 77,29 (1982)).

$FeCl_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20%) is expressed in terms of the actual weight of $FeCl_3$ only. To injure the artery and induce thrombosis, 2.85 μl is pipetted into the cuff to bathe the artery above the thermocouple probe. Arterial occlusion is indicated by a rapid drop in temperature. The time to occlusion is reported in minutes and represented the elapsed time between application of $FeCl_3$ and the rapid drop in vessel temperature (see K. D. Kurz, *Thromb. Res.*, 60, 269 (1990)).

Spontaneous thrombolysis model

In vitro data suggested that the peptide thrombin inhibitors inhibit thrombin and other serine proteases, such as plasmin and tissue plasminogen activator. To assess if the compounds inhibited fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}I$ human fibrogen (5 μCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected } cpm - \text{lung } cpm)}{\text{injected } cpm} \times 100$$

The fibrinolytic dissolution of the implanted clot occurs time-dependently (see J. P. Clozel, *Cardiovas. Pharmacol.*, 12, 520 (1988)).

Coagulation parameters

Plasma thrombin time (TT) and activated partial thromboplastin time (APTT) are measured with a fibrometer. Blood is sampled from a jugular catheter and collected in syringe containing sodium citrate (3.8%, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.01 mL, 0.025M) is added to start coagulation. Assays are done in duplicate and averaged.

Index of Bioavailability

A measure of bioactivity, plasma thrombin time (TT), served as a substitute for the assay of parent compound on the assumption that increments in TT resulted from thrombin inhibition by parent only. The time course of the effect of the thrombin inhibitor upon TT is determined after i.v. bolus administration to anesthetized rats and after oral treatment of fasted conscious rats. Due to limitations of blood volume and the number of points required to determine the time course from time of treatment to the time when the response returned to pretreatment values, two populations of rats are used. Each sample population represented alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\, po}{AUC\, iv} \times \frac{\text{Dose } iv}{\text{Dose } po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl₃ model of arterial injury and in the spontaneous thombosis model. Bolus injection volume is 1 mL/kg for i.v., and 5 mL/kg for p.o. and infusion volume is 3 mL/hr.

Statistics

Results are expressed as means±SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months—2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°–74° F.; 45–50% relative humidity; and lighted from 0600–1800 hours.

Pharmacokinetic model.

Test compound is formulated immediately prior to dosing by dissolving in sterile 0.9% saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-C8 column) eluting with methanol/500 mM sodium acetate adjusted to pH 7 with phosphoric acid (60:40, v/v). Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound at Tmax, Cmax; plasma half-life, t0.5; area under the curve, A.U.C.; and fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon®-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50% inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-µA direct current (DC) to the anode. The current is maintained for 60 minutes and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/h is begun simultaneously with an infusion of thrombolytic agent (e.g. tissue plasminogen activator, streptokinase, APSAC). Reperfusion is followed for 3 hours after administration of test compound. Reocclusion of coronary arteries after successful thrombolysis is defined as zero CBF which persisted for $\geq 30$ minutes.

Hematology and template bleeding time determinations

Whole blood cell counts, hemoglobin, and hematocrit values are determined on a 40-µl sample of citrated (3.8%) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 minutes), 60 minutes into infusion, at conclusion of administration of the test compound (120 minutes), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, 21, 587–599 (1993).

TABLE 2

| Example | Human Plasma Anticoagulation 2x Clotting time (ng/mL) | | | |
|---|---|---|---|---|
| | TT | APTT | PT | % oral/i.v. activity (Rat) |
| 1 | 60 | 510 | 1,700 | 47 |
| 2 | 51 | 460 | 1,500 | 50 |
| 3 | 120 | 610 | 2,900 | 45 |
| 4 | 130 | 630 | 3,100 | NT |

TABLE 2-continued

| | Human Plasma Anticoagulation 2x Clotting time (ng/mL) | | | |
|---|---|---|---|---|
| Example | TT | APTT | PT | % oral/i.v. activity (Rat) |
| 5 | 80 | 510 | 1,600 | 20 |
| 6 | 340 | 840 | 4,100 | NT |
| 7 | 37 | 450 | 1,500 | 50 |
| 8 | 70 | 520 | 1,900 | 20 |
| 9 | 50 | 880 | 3,100 | 13 |
| 10 | 480 | 2,200 | 10,000 | NT |
| 11 | 96 | 1,400 | 5,900 | 9 |
| 12 | 210 | 1,300 | 4,100 | NT |
| 13 | 490 | 2,900 | 9,100 | NT |
| 14 | 460 | 9,000 | 18,000 | NT |
| 15 | 28 | 940 | 1,600 | 5 |
| 16 | 120 | 2,400 | 4,900 | NT |
| 17 | 16 | 380 | 1,200 | NT |
| 18 | 248 | 5,969 | 10,783 | NT |
| 19 | 345 | 3,497 | 8,822 | NT |
| 20 | 19 | 627 | 1,452 | 6 |
| 21 | 1,199 | 16,234 | 30,776 | NT |
| 22 | 9 | 332 | 1,208 | 30 |
| 23 | 19 | 312 | 746 | NT |
| 24 | 11 | 490 | 727 | NT |
| 25 | 25 | 548 | 1,232 | NT |
| 26 | 82 | 392 | 1,322 | NT |
| 27 | 116 | 395 | 1,232 | NT |
| 28 | 3,637 | 22,727 | 43,401 | NT |

We claim:

1. A compound having the Formula I $$X-Y-N-\underset{*}{\overset{\overset{H}{|}}{C}}-(CH_2)_3-N-\overset{\overset{NH}{\|}}{C}-NH_2 \quad I$$
$$\underset{\overset{|}{H}}{\overset{|}{C}=O}$$

wherein

X is prolinyl, homoprolinyl,

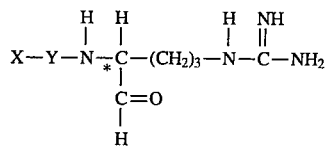

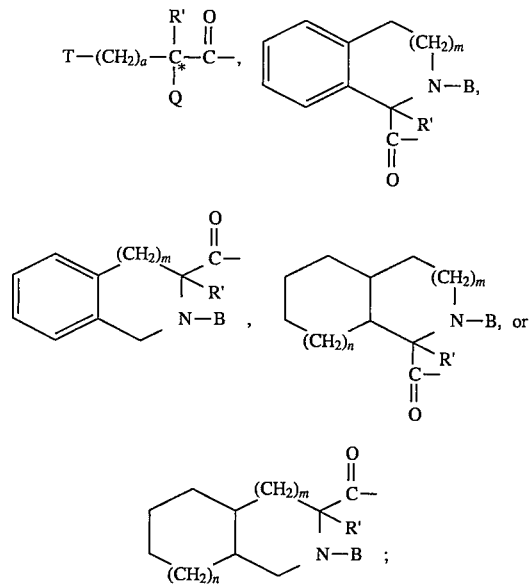

T is $C_3-C_8$ cycloalkyl, $C_1-C_8$ alkyl,

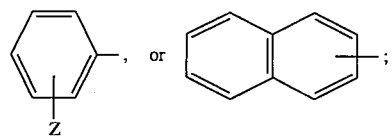

a is 0 or 1;

Q is —OH, $C_1-C_4$ alkoxy, or —NH—A;

A is $C_1-C_4$ alkyl, R"SO$_2$—, R"OC(O)—, R"C(O)—, HOOCSO$_2$—, HOOCC(O)—, or —(CH$_2$)$_g$—COOH;

g is 1, 2, or 3;

B is hydrogen or $C_1-C_4$ alkyl;

R' is hydrogen or $C_1-C_4$ alkyl;

R" is $C_1-C_4$ alkyl, $C_1-C_4$ perfluoroalkyl, —(CH$_2$)$_d$—COOH, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

d is 1, 2, or 3;

m is 0, 1, or 2;

n is 0, 1, or 2;

Y is

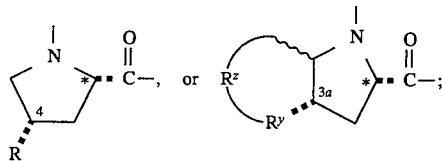

R is $C_1-C_6$ alkyl, $C_3-C_8$ cycloalkyl, or —(CH$_2$)$_p$—L—(CH$_2$)$_q$—T'; where p is 0, 1, 2, 3, or 4, L is a bond, —O—, —S—, or —NH—, q is 0, 1, 2 or 3, and T' is hydrogen, $C_1-C_4$ alkyl, $C_3-C_8$ cycloalkyl, —COOH, —CONH$_2$, or Ar, where Ar is unsubstituted or substituted aryl as defined above for R";

R$^y$ is —CH$_2$—, —O—, —S—, or —NH—;

R$^z$ is a bond or, when taken with R$^y$ and the three adjoining carbon atoms, forms a saturated carbocyclic ring of 5–8 atoms, one atom of which may be —O—, —S—, or —NH—; and Z is hydrogen, $C_1-C_4$ alkyl, $C_1-C_4$ alkoxy, hydroxy, halo, or R$_a$SO$_2$NH—, where R$_a$ is $C_1-C_4$ alkyl;

provided that when p and q are each 0 and L is a bond, T' is not hydrogen;

or a pharmaceutically acceptable salt thereof; or a pharmaceutically acceptable solvate of said compound or salt thereof.

2. The compound or salt or solvate thereof as claimed in claim 1 wherein alkyl by itself or as part of another substituent is methyl, ethyl, n-propyl, isopropyl, n-butyl, t-butyl, isobutyl or sec-butyl;

perfluoroalkyl by itself or as part of another substituent is trifluoromethyl, perfluoroethyl, perfluoro-n-propyl, perfluoroisopropyl, perfluoro-n-butyl, perfluoro-t-butyl, perfluoroisobutyl or perfluoro-sec-butyl;

$C_3$–$C_8$ cycloalkyl is cyclopropyl, methylcyclopropyl, cyclobutyl, cyclopentyl, cyclohexyl, 4-methylcyclohexyl, or cyclooctyl;

halo is chloro, fluoro, bromo or iodo;

a 5- or 6-membered heterocyclic ring is furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl or thiazinyl;

a 9- or 10-membered heterocyclic ring is indolyl, benzothienyl, benzofuryl, benzoxazolyl, benzoisoxazolyl, benzopyrazolyl, quinolinyl, isoquinolinyl, benzimidazolyl or benzothiazolyl;

and further wherein any of the aryl groups listed for the definition of R" or Ar independently is unsubstituted or substituted with one or two substituents that will afford a stable structure independently selected from halo, hydroxyl, $C_1$–$C_4$ alkyl, $C_1$–$C_4$ alkoxy, amino(—$NH_2$), mono($C_1$–$C_4$ alkyl)amino, —$(CH_2)_k COOH$, mercapto, —$S(O)_h(C_1$–$C_4$ alkyl), —$NHS(O)_h(C_1$–$C_4$ alkyl), —$NHC(O)(C_1$–$C_4$ alkyl), —$S(O)_h NH_2$, —$S(O)_h NH(C_1$–$C_4$ alkyl), or —$S(O)_h N(C_1$–$C_4$ alkyl)$_2$, h is 0, 1 or 2, and k is 0, 1, 2, 3, or 4.

3. The compound or salt or solvate thereof as claimed in claim 1 where X is

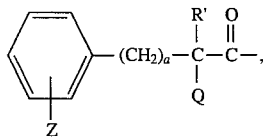

homoprolinyl, 1- or 3-Tiq, or 1- or 3-Piq, and Y is substituted prolinyl or Ohi.

4. The compound or salt or solvate thereof as claimed in claim 3 wherein Q is NHA and A is R"$SO_2$—, R' is hydrogen, and B is hydrogen.

5. The compound or salt or solvate thereof as claimed in claim 4 wherein R is $C_1$–$C_6$ alkyl or Ar—O—.

6. The compound or salt or solvate thereof as claimed in claim 1 where X is N-ethylsulfonyl-D-phenylglycyl, N-ethylsulfonyl-D-phenylalanyl, N-(carboxymethyl)-D-phenyalanyl, D-homoprolinyl, or D-cis[4aS,8aS]-perhydroisoquinoline-1-carbonyl.

7. The compound or salt or solvate thereof as claimed in claim 1 where Y is (S)-cis-octahydroindole-2-carbonyl.

8. The compound or salt or solvate thereof as claimed in claim 1 which compound is selected from a. D-homoprolyl-L-cis-4-methylprolyl-L-argininal, b. D-homoprolyl-L-cis-4-ethylprolyol-L-argininal, c. $N^\alpha$-[(1-D-homoprolyl-cis-octahydro-1H-indol-2(S)-yl)carbonyl]-L-arginal, d. D-cis-perhydro-isoquinoline-1-carbonyl-L-cis-4-phenyoxyprolyl-L-arginal, e. $N^\alpha$-ethylsulfonyl-D-phenylgycyl-L-cis-4-phenoxyprolyl-L-arginal, f. $N^\alpha$-[(1-[D-cis-perhydro-isoquinoline-1-carbonyl]-cis-octahydro-1H-indol-2(S)-yl)carbonyl]-L-arginal, g. $N^\alpha$-[(1-[$N^\alpha$-ethylsulfonyl-D-phenylglycyl]-cis-octahydro-1H-indol-2(S)-yl)carbonyl]-L-arginal, h. $N^\alpha$-[(1-[$N^\alpha$-ethylsulfonyl-D-phenylalanyl]-cis-octahydrro-1H-indol-2(S)-yl)carbonyl]-L-arginal, and i. $N^\alpha$-[(1-[$N^\alpha$-carboxymethyl-D-phenylalanyl]-cis-octahydro-1H-indol-2(S)-yl)carbonyl]-L-arginal.

9. A pharmaceutical formulation comprising in association with a pharmaceutically acceptable carrier, diluent, or excipient, the compound of Formula I, or a pharmaceutically acceptable salt or solvate thereof, as claimed in claim 1.

10. The formulation of claim 9 wherein alkyl by itself or as part of another substituent is methyl, ethyl, n-propyl, isopropyl, n-butyl, t-butyl, isobutyl or sec-butyl;

perfluoroalkyl by itself or as part of another substituent is trifluoromethyl, perfluoroethyl, perfluoro-n-propyl, perfluoroisopropyl, perfluoro-n-butyl, perfluoro-t-butyl, perfluoroisobutyl or perfluoro-sec-butyl;

$C_3$–$C_8$ cycloalkyl is cyclopropyl, methylcyclopropyl, cyclobutyl, cyclopentyl, cyclohexyl, 4-methylcyclohexyl, or cyclooctyl;

halo is chloro, fluoro, bromo or iodo;

a 5- or 6-membered heterocyclic ring is furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl or thiazinyl;

a 9- or 10-membered heterocyclic ring is indolyl, benzothienyl, benzofuryl, benzoxazolyl, benzoisoxazolyl, benzopyrazolyl, quinolinyl, isoquinolinyl, benzimidazolyl or benzothiazolyl;

and further wherein any of the aryl groups listed for the definition of R" or Ar independently is unsubstituted or substituted with one or two substituents that will afford a stable structure independently selected from halo, hydroxyl, $C_1$–$C_4$ alkyl, $C_1$–$C_4$ alkoxy, amino(—$NH_2$), mono($C_1$–$C_4$ alkyl)amino, —$(CH_2)_k COOH$, mercapto, —$S(O)_h(C_1$–$C_4$ alkyl), —$NHS(O)_h(C_1$–$C_4$ alkyl), —$NHC(O)(C_1$–$C_4$ alkyl), —$S(O)_h NH_2$, —$S(O)_h NH(C_1$–$C_4$ alkyl), or —$S(O)_h N(C_1$–$C_4$ alkyl)$_2$, h is 0, 1 or 2, and k is 0, 1, 2, 3, or 4.

11. The formulation of claim 9 where X

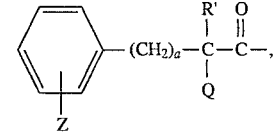

homoprolinyl, 1- or 3-Tiq, or 1- or 3-Piq, and Y is substituted prolinyl or Ohi.

12. The formulation of claim 11 wherein Q is NHA and A is R"$SO_2$—, R' is hydrogen, and B is hydrogen.

13. The A formulation of claim 12 wherein R is $C_1$–$C_6$ alkyl or Ar—O—.

14. The formulation of claim 9 where X is N-ethylsulfonyl-D-phenylglycyl, N-ethylsulfonyl-D-phenylalanyl, N-(carboxymethyl)-D-phenylalanyl, D-homoprolinyl, or D-cis[4aS,8aS]-perhydroisoquinoline-1-carbonyl.

15. The formulation of claim 9 where Y is (S)-cis-octahydroindole-2-carbonyl.

16. The formulation of claim 9 in which said compound is selected from a. D-homoprolyl-L-cis-4-methylprolyl-L-argininal, b. D-homoprolyl-L-cis-4-ethylprolyl-L-argininal, c. $N^\alpha$-[(1-D-homoprolyl-cis-octahydro-1H-indol-2(S)-yl)carbonyl]-L-arginal, d. D-cis-perhydro-isoquinoline-1-carbonyl-L-cis-4-phenoxyprolyl-L-arginal, e. $N^\alpha$-ethylsulfonyl-D-phenylgycyl-L-cis-4-phenoxyprolyl-L-arginal, f. $N^\alpha$-[(1-[D-cis-perhydro-isoquinoline-1-carbonyl]-cis-octahydro-1H-indol-2(S)-yl)carbonyl]-L-arginal, g. $N^\alpha$-[(1-[$N^\alpha$-ethylsulfonyl-D-phenylglycyl]-cis-octahydro-1H-indol-2(S)-yl)carbonyl]-L-arginal, h. $N^\alpha$-[(1-[$N^\alpha$-ethylsulfonyl-D-phenylalanyl]-cis-octahydro-1H-indol-2(S)-yl)carbonyl]-L-arginal, and i. $N^\alpha$-[(1-[$N^\alpha$-carboxymethyl-D-phenylalanyl]-cis-octahydro-1H-indol-2(S)-yl)carbonyl]-L-arginal.

17. A method of inhibiting thrombin in a mammal comprising administering an effective dose of the compound, or a pharmaceutically acceptable salt or solvate thereof, as claimed in claim 1 to a mammal requiring thrombin inhibition.

18. The method of claim 17 wherein alkyl by itself or as part of another substituent is methyl, ethyl, n-propyl, isopropyl, n-butyl, t-butyl, isobutyl or sec-butyl;

perfluoroalkyl by itself or as part of another substituent is trifluoromethyl, perfluoroethyl, perfluoro-n-propyl, perfluoroisopropyl, perfluoro-n-butyl, perfluoro-t-butyl, perfluoroisobutyl or perfluoro-sec-butyl;

$C_3$–$C_8$ cycloalkyl is cyclopropyl, methylcyclopropyl, cyclobutyl, cyclopentyl, cyclohexyl, 4-methylcyclohexyl, or cyclooctyl;

halo is chloro, fluoro, bromo or iodo;

a 5- or 6-membered heterocyclic ring is furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl or thiazinyl;

a 9- or 10-membered heterocyclic ring is indolyl, benzothienyl, benzofuryl, benzoxazolyl, benzoisoxazolyl, benzopyrazolyl, quinolinyl, isoquinolinyl, benzimidazolyl or benzothiazolyl;

and further wherein any of the aryl groups listed for the definition of R" or Ar independently is unsubstituted or substituted with one or two substituents that will afford a stable structure independently selected from halo, hydroxyl, $C_1$–$C_4$ alkyl, $C_1$–$C_4$ alkoxy, amino(—$NH_2$), mono($C_1$–$C_4$ alkyl)amino, —$(CH_2)_k$COOH, mercapto, —$S(O)_h(C_1$–$C_4$ alkyl), —$NHS(O)_h(C_1$–$C_4$ alkyl), —$NHC(O)(C_1$–$C_4$ alkyl), —$S(O)_hNH_2$, —$S(O)_hNH(C_1$–$C_4$ alkyl), or —$S(O)_hN(C_1$–$C_4$ alkyl)_2$, h is 0, 1 or 2, and k is 0, 1, 2, 3, or 4.

19. The method of claim 17 where X is

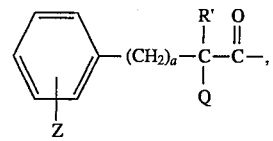

homoprolinyl, 1- or 3-Tiq, or 1- or 3-Piq, and Y is substituted prolinyl or Ohi.

20. The method of claim 19 wherein Q is NHA and A is R"$SO_2$—, R' is hydrogen, and B is hydrogen.

21. The method of claim 20 wherein R is $C_1$–$C_6$ alkyl or Ar—O—.

22. The method of claim 17 where X is N-ethylsulfonyl-D-phenylglycyl, N-ethylsulfonyl-D-phenylalanyl, N-(carboxymethyl)-D-phenylalanyl, D-homoprolinyl, or D-cis [4aS,8aS]-perhydroisoquinoline-1-carbonyl.

23. The method of claim 17 where Y is (S)-cis-octahydroindole-2-carbonyl.

24. The method of claim 17 in which said compound is selected from a. D-homoprolyl-L-cis-4-methylprolyl-L-argininal, b. D-homoprolyl-L-cis-4-ethylprolyl-L-argininal, c. $N^\alpha$-[(1-D-homoprolyl-cis-octahydro-1H-indol-2(S)-yl)carbonyl]-L-arginal, d. D-cis-perhydro-isoquinoline-1-carbonyl-L-cis-4-phenoxyprolyl-L-arginal, e. $N^\alpha$-ethylsulfonyl-D-phenylgycyl-L-cis-4-phenoxyprolyl-L-arginal, f. $N^\alpha$-[(1-[D-cis-perhydro-isoquinoline-1-carbonyl]cis-octahydro-1H-indol-2(S)-yl)carbonyl]-L-arginal, g. $N^\alpha$-[(1-[$N^\alpha$-ethylsulfonyl-D-phenylglycyl]-cis-octahydro-1H-indol-2(S)-yl)carbonyl]-L-arginal, h. $N^\alpha$-[(1-[$N^\alpha$-ethylsulfonyl-D-phenylalanyl]-cis-octahydro-1H-indol-2(S)-yl)carbonyl]-L-arginal, and i. $N^\alpha$-[(1-[$N^\alpha$-carboxymethyl-D-phenylalanyl]-cis-octahydro-1H-indol-2(S)-yl)carbonyl]-L-arginal.

* * * * *